United States Patent
Alderson et al.

(10) Patent No.: US 6,555,653 B2
(45) Date of Patent: Apr. 29, 2003

(54) COMPOUNDS FOR DIAGNOSIS OF TUBERCULOSIS AND METHODS FOR THEIR USE

(75) Inventors: Mark Raymond Alderson, Bainbridge Island, WA (US); Davin C. Dillon, Redmond, WA (US); Yasir A. W. Skeiky, Seattle, WA (US); Antonio Campos-Neto, Bainbridge Island, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/073,009

(22) Filed: May 5, 1998

(65) Prior Publication Data

US 2001/0012888 A1 Aug. 9, 2001

Related U.S. Application Data

(63) Continuation-in-part of application No. 08/858,998, filed on May 20, 1997, now abandoned.

(51) Int. Cl.$^7$ .......................... C07K 1/00; C07K 14/00; A61K 39/04; A61K 39/02; A61K 39/38
(52) U.S. Cl. ................. 530/350; 424/248.1; 424/184.1; 424/234.1; 424/192.1; 424/168.1; 536/23.1
(58) Field of Search ........................ 536/23.1; 530/350; 424/192.1, 234.1, 168.1, 184.1, 248.1

(56) References Cited

U.S. PATENT DOCUMENTS

| | | | |
|---|---|---|---|
| 4,689,397 A | | 8/1987 | Shinnick et al. |
| 4,879,213 A | | 11/1989 | Fox et al. |
| 4,952,395 A | | 8/1990 | Shinnick et al. |
| 5,330,754 A | | 7/1994 | Kapoor et al. |
| 5,478,726 A | | 12/1995 | Shinnick et al. |
| 5,985,287 A | * | 11/1999 | Tan et al. |
| 6,001,361 A | * | 12/1999 | Tan et al. |
| 6,034,218 A | * | 3/2000 | Reed et al. |
| 6,290,969 B1 | * | 9/2001 | Reed et al. ............... 424/168.1 |
| 6,338,852 B1 | * | 1/2002 | Reed et al. ............... 424/248.1 |
| 6,350,456 B1 | * | 2/2002 | Reed et al. ............... 424/168.1 |

FOREIGN PATENT DOCUMENTS

| | | |
|---|---|---|
| WO | WO 97/09428 A2 | 3/1997 |
| WO | WO 97/09429 A2 | 3/1997 |

OTHER PUBLICATIONS

Philipp et al, PNAS,USA; 93:3132–3137, 1996.*
Dillon et al, Infection & Immunity 67/6:2941–2950, 1999.*
Coler et al, J. Immunology 161:2356–2364, 1998.*
Skeiky et al, Infection & Immunity 67/8:3998–4007, 1999.*
Webb et al, Infection & Immunity 66/9:4208–4214, 1998.*
Alderson et al, J. Exp. Med. 191/3:551–559, 2000.*
Compugen Search Results Accession #P96363, 1997.*
Compugen Search Results Accession #Q10813, 1996.*
Compugen Search Results; Accession #P95242, 1997.*
Compugen Search Results; Accession #P96363, 1997.*
Compugen Search Results; Accession #P95243, 1997.*
Compugen Search Results; Accession #P96361, 1997.*
Compugen Search Results; Accession #P95012, 1997.*
Compugen Search Results; Accession #Q49722, 1996.*
Andersen, et al., "Identification of Immunodominant Antigens during Infection with *Mycobacterium tuberculosis*"; *Scand. J. Immunol.* 36:823–831 (1992).
Andersen and Heron "Specificity of a Protective Memory Immune Response against *Mycobacterium tuberculosis*" *Infection and Immunity* 61(3):844–851 (1993).
Burgess et al. "Possible Dissociation of the Heparin–binding and Mitogenic Activities of Heparin–Binding (Acidic Fibroblast) Growth Factor–1 from its Receptor–binding Activities by Site–Directed Mutagenesis of a Single Lysine Residue" *J. Cell. Biol.* 111:2129–2138 (1990.
Eiglmeier et al. "Use of an ordered cosmid library to deduce the genomic organization of *Mycobacteirum leprae*" *Mol. Microbiol.* 7(2):197–206 (1993).
Fifis et al. "Purification and Characterization of Major Antigens from a *Mycobacterium bovis* Culture Filtrate" *Infection and Immunity* 59(3):800–807 (1991).
Geysen et al. "Cognitive features of continuous antigenic determinants" *J. Mol. Recognition* 1:32–41 (1988).
Greenway et al. "Enhancement of protective immune response to Venezuelan equine encephalitis (VEE) virus with microencapsulated vaccine" *Vaccine* 13:1411–1420 (1995).
Kadival et al. "Radioimmunoassay of tuberculous antigen" *Indian J. Med. Res.* 75:765–770 (1982).
Lazar et al. "Transforming Growth Factor α: Mutation of Aspartic Acid 47 and Leucine 48 results in Different Biological Activities" *Mol. Cell. Biol.* 8(3):1247–1252 (1988.
Lee et al. "Characterization of the Major Membrane Protein of Virulent *Mycobacterium tuberculosis*" *Infection and Immunity* 60:2066–2074 (1992).
Mathur and Kolttukudy "Molecular cloning and sequencing of the gene for mycocerosic acid synthase, a novel fatty acid elongating multifunctional enzyme, from *Mycobacterium tuberculosis* var. *bovis* Bacillus Calmette–Guerin" *J. Biol. Chem.* 267:19388–19395 (1992).
Orme "Prospects for new vaccines against tuberculosis" *Trends in Microbiology* 3(10):401–404 (1995).

(List continued on next page.)

*Primary Examiner*—Nita M Minnifield
(74) *Attorney, Agent, or Firm*—Townsend and Townsend and Crew LLP

(57) ABSTRACT

Compounds and methods for diagnosing tuberculosis are disclosed. The compounds provided include polypeptides that contain at least one antigenic portion of one or more *M. tuberculosis* proteins, and DNA sequences encoding such polypeptides. Diagnostic kits containing such polypeptides or DNA sequences and a suitable detection reagent may be used for the detection of *M. tuberculosis* infection in patients and biological samples. Antibodies directed against such polypeptides are also provided.

13 Claims, 2 Drawing Sheets

OTHER PUBLICATIONS

Pancholi et al. "Dendritic cells efficiently immunoselect mycobacterial–reactive T cells in human blood, including clonable antigen–reactive precursors" *Immunology* 76(2):217–224 (1992).

Philipp et al. "An integrated map of the genome of the tubercle bacillus, *Mycobacterium tuberculosis* H37Rv, and comparison with *Mycobacterium leprae*" *Proc. Natl. Acad. Sci. USA* 93(7):3132–3137 (1996.

Rinke de Wit et al. "A *Mycobacterium leprae*–specific gene encoding an immunologically recognized 45 KDa protein" *Mol. Microbiol.* 10(4):829–838 (1993).

Rinke de Wit et al. "Mycobacterium contains two groEL genes: the second *Mycobacterium leprae* groEL gene is arranged in an operon with groES" *Mol. Microbiol.* 6(14):1995–2007 (1992).

Romain et al. "Identification of a *Mycobacterium bovis* BCG 45/47–Kilodalton Antigen Complex, an Immunodominant Target for Antibody Response after Immunization with Living Bacteria" *Infection and Immunity* 61(2):742–750 (1993).

Sanderson et al. "Identification of a CD4+ T Cell–stimulating Antigen of Pathogenic Bacteria by Expression Cloning" *J. Exp. Med.* 182(6):1751–1757 (1995).

Vega–Lopez et al. "Sequence and immunological characterization of a serine–rich antigen from *Mycobacterium leprae*" *Infection and Immunity* 61(5):2145–2153 (1993).

Wieles et al. "Characterization of a *Mycobacterium leprae* Antigen Related to the Secreted *Mycobacterium tuberculosis* Protein MPT32" *Infection and Immunity* 62(1):252–258 (1994).

Database EMBL Empro, Entry MTCY7H7B, Accession No. Z95557, May 20, 1997.

Database EMBL Empro, Entry MTCY24G1, Accession No. Z83858, Jan. 13, 1997.

Database EMBL Empro Entry MTCY19G5, Accession No. Z77826, Jul. 31, 1996.

Database EMBL Empro Entry MTCY261, Accession No. Z97559, Jul. 10, 1997.

* cited by examiner

US 6,555,653 B2

COMPOUNDS FOR DIAGNOSIS OF TUBERCULOSIS AND METHODS FOR THEIR USE

CROSS REFERENCE TO RELATED APPLICATIONS

This application is a continuation-in-part of U.S. patent application Ser. No. 08/858,998, filed May 20, 1997, now abandoned.

TECHNICAL FIELD

The present invention relates generally to the detection of *Mycobacterium tuberculosis* infection. The invention is more particularly related to polypeptides comprising a *Mycobacterium tuberculosis* antigen, or a portion or other variant thereof, and the use of such polypeptides for the serodiagnosis of *Mycobacterium tuberculosis* infection.

BACKGROUND OF THE INVENTION

Tuberculosis is a chronic, infectious disease, that is generally caused by infection with *Mycobacterium tuberculosis*. It is a major disease in developing countries, as well as an increasing problem in developed areas of the world, with about 8 million new cases and 3 million deaths each year. Although the infection may be asymptomatic for a considerable period of time, the disease is most commonly manifested as an acute inflammation of the lungs, resulting in fever and a nonproductive cough. If left untreated, serious complications and death typically result.

Although tuberculosis can generally be controlled using extended antibiotic therapy, such treatment is not sufficient to prevent the spread of the disease. Infected individuals may be asymptomatic, but contagious, for some time. In addition, although compliance with the treatment regimen is critical, patient behavior is difficult to monitor. Some patients do not complete the course of treatment, which can lead to ineffective treatment and the development of drug resistance.

Inhibiting the spread of tuberculosis will require effective vaccination and accurate, early diagnosis of the disease. Currently, vaccination with live bacteria is the most efficient method for inducing protective immunity. The most common Mycobacterium for this purpose is Bacillus Calmette-Guerin (BCG), an avirulent strain of *Mycobacterium bovis*. However, the safety and efficacy of BCG is a source of controversy and some countries, such as the United States, do not vaccinate the general public. Diagnosis is commonly achieved using a skin test, which involves intradermal exposure to tuberculin PPD (protein-purified derivative). Antigen-specific T cell responses result in measurable incubation at the injection site by 48–72 hours after injection, which indicates exposure to Mycobacterial antigens. Sensitivity and specificity have, however, been a problem with this test, and individuals vaccinated with BCG cannot be distinguished from infected individuals.

While macrophages have been shown to act as the principal effectors of *M. tuberculosis* immunity, T cells are the predominant inducers of such immunity. The essential role of T cells in protection against *M. tuberculosis* infection is illustrated by the frequent occurrence of *M. tuberculosis* in AIDS patients, due to the depletion of CD4 T cells associated with human immunodeficiency virus (HIV) infection. Mycobacterium-reactive CD4 T cells have been shown to be potent producers of gamma-interferon (IFN-γ), which, in turn, has been shown to trigger the anti-mycobacterial effects of macrophages in mice. While the role of IFN-γ in humans is less clear, studies have shown that 1,25-dihydroxy-vitamin D3, either alone or in combination with IFN-γ or tumor necrosis factor-alpha, activates human macrophages to inhibit *M. tuberculosis* infection. Furthermore, it is known that IFN-γ stimulates human macrophages to make 1,25-dihydroxy-vitamin D3. Similarly, IL-12 has been shown to play a role in stimulating resistance to *M. tuberculosis* infection. For a review of the immunology of *M. tuberculosis* infection see Chan and Kaufmann, in *Tuberculosis: Pathogenesis, Protection and Control*, Bloom (ed.), ASM Press, Washington, D.C., 1994.

Accordingly, there is a need in the art for improved diagnostic methods for detecting tuberculosis. The present invention fulfills this need and further provides other related advantages.

SUMMARY OF THE INVENTION

Briefly stated, the present invention provides compositions and methods for diagnosing tuberculosis.

In one embodiment, polypeptides are provided that comprise an antigenic portion of a *M. tuberculosis* antigen, or a variant of such an antigen that differs only in conservative substitutions and/or modifications, wherein the antigen comprises an amino acid sequence encoded by a DNA sequence selected from the group consisting of the sequences recited in SEQ ID NO: 1, 11, 12, 83, 103–108, 125, 127, 129–137, 139 and 140, the complements of said sequences, and DNA sequences that hybridize to a sequence recited in SEQ ID NO: 1, 11, 12, 83, 103–108, 125, 127, 129–137, 139 and 140, or a complement thereof, under moderately stringent conditions. In a second embodiment, the present invention provides polypeptides comprising an immunogenic portion of a *M. tuberculosis* antigen having an amino acid sequence selected from the group consisting of sequences provided in SEQ ID NO: 16–33, 109, 126, 138, 141, 142 and variants thereof In related aspects, DNA sequences encoding the above polypeptides, recombinant expression vectors comprising these DNA sequences and host cells transformed or transfected with such expression vectors are also provided.

In another aspect, the present invention provides fusion proteins comprising a first and a second inventive polypeptide or, alternatively, an inventive polypeptide and a known *M. tuberculosis* antigen.

In further aspects of the subject invention, methods and diagnostic kits are provided for detecting tuberculosis in a patient. The methods comprise: (a) contacting a biological sample with at least one of the above polypeptides; and (b) detecting in the sample the presence of antibodies that bind to the polypeptide or polypeptides, thereby detecting *M. tuberculosis* infection in the biological sample. Suitable biological samples include whole blood, sputum, serum, plasma, saliva, cerebrospinal fluid and urine. The diagnostic kits comprise one or more of the above polypeptides in combination with a detection reagent.

The present invention also provides methods for detecting *M. tuberculosis* infection comprising: (a) obtaining a biological sample from a patient; (b) contacting the sample with at least one oligonucleotide primer in a polymerase chain reaction, the oligonucleotide primer being specific for a DNA sequence encoding the above polypeptides; and (c) detecting in the sample a DNA sequence that amplifies in the presence of the first and second oligonucleotide primers. In one embodiment, the oligonucleotide primer comprises at least about 10 contiguous nucleotides of such a DNA sequence.

In a further aspect, the present invention provides a method for detecting *M. tuberculosis* infection in a patient comprising: (a) obtaining a biological sample from the patient; (b) contacting the sample with an oligonucleotide probe specific for a DNA sequence encoding the above polypeptides; and (c) detecting in the sample a DNA sequence that hybridizes to the oligonucleotide probe. In one embodiment, the oligonucleotide probe comprises at least about 15 contiguous nucleotides of such a DNA sequence.

In yet another aspect, methods are provided for detecting tuberculosis in a patient, such methods comprising contacting a biological sample with one or more polypeptides encoded by a DNA sequence selected from the group consisting of SEQ ID NO: 2–10, 102, 128, the complements of said sequences, and DNA sequences that hybridize to a sequence recited in SEQ ID NO: 2–10, 102, 128; and detecting in the sample the presence of antibodies that bind to the polypeptide, thereby detecting *M. tuberculosis* infection in the biological sample. Diagnostic kits for use in such methods are also provided.

In another aspect, the present invention provides antibodies, both polyclonal and monoclonal, that bind to the polypeptides described above, as well as methods for their use in the detection of *M. tuberculosis* infection.

These and other aspects of the present invention will become apparent upon reference to the following detailed description and attached drawings. All references disclosed herein are hereby incorporated by reference in their entirety as if each was incorporated individually.

DETAILED DESCRIPTION OF THE INVENTION

Figure 1A:
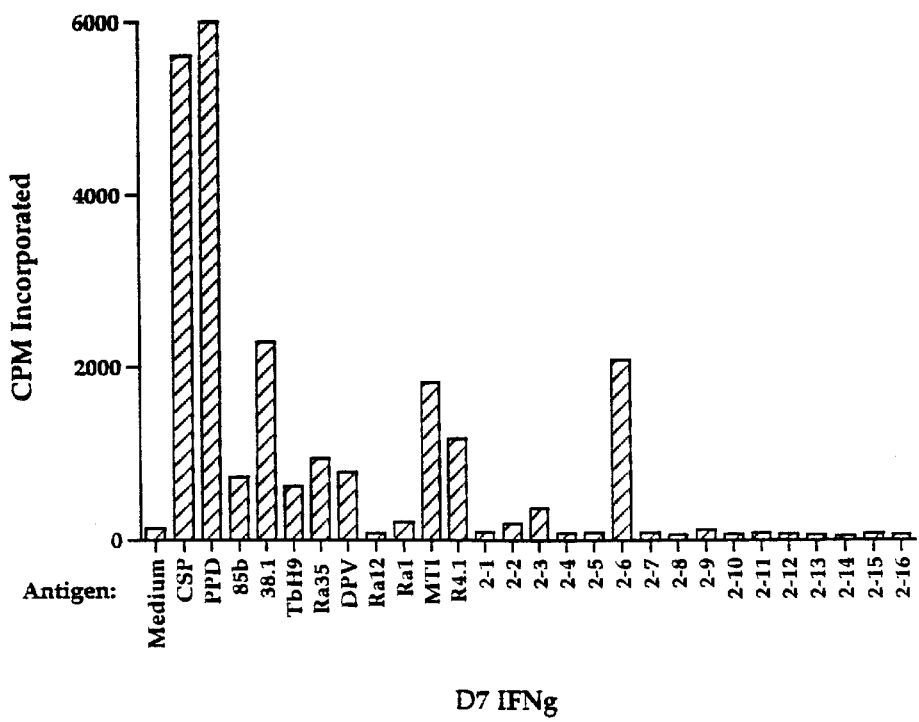
FIGS. 1 and 1B illustrate the stimulation of proliferation and interferon-γ production, respectively, in T cells derived from a first PPD-positive donor (referred to as D7) by recombinant ORF-2 and synthetic peptides to ORF-2.
Figure 1B:
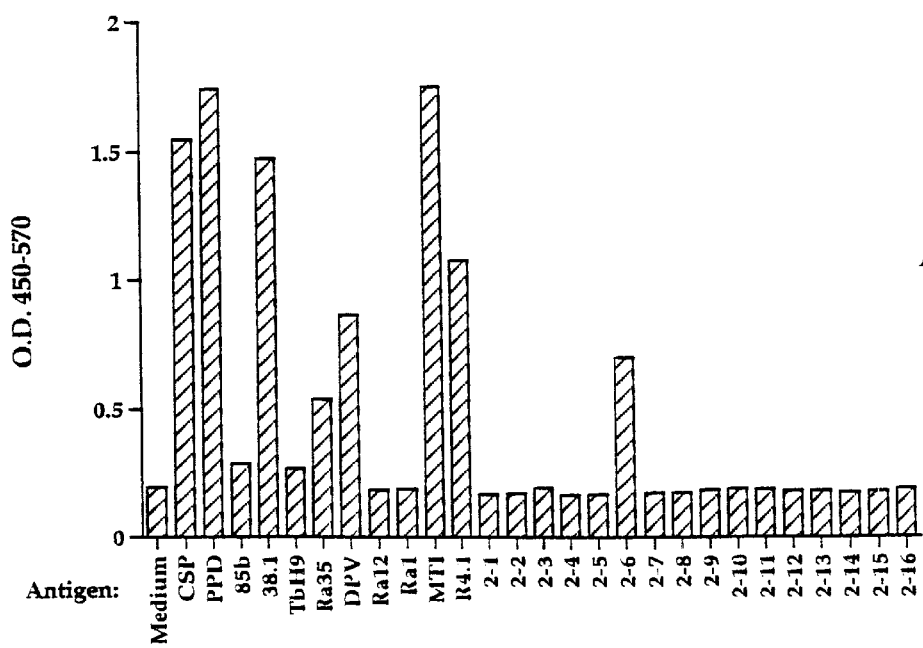
Figure 2A:
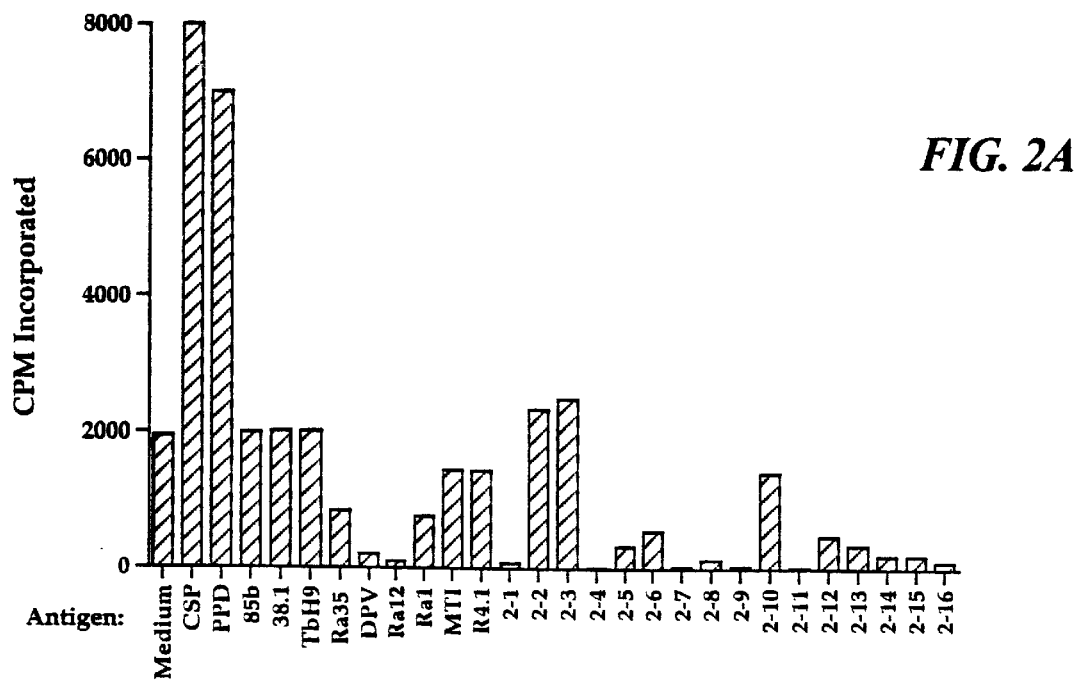
FIGS. 2A and 2B illustrate the stimulation of proliferation and interferon-γ production, respectively, in T cells derived from a second PPD-positive donor (referred to as D160) by recombinant ORF-2 and synthetic peptides to ORF-2.
Figure 2B:
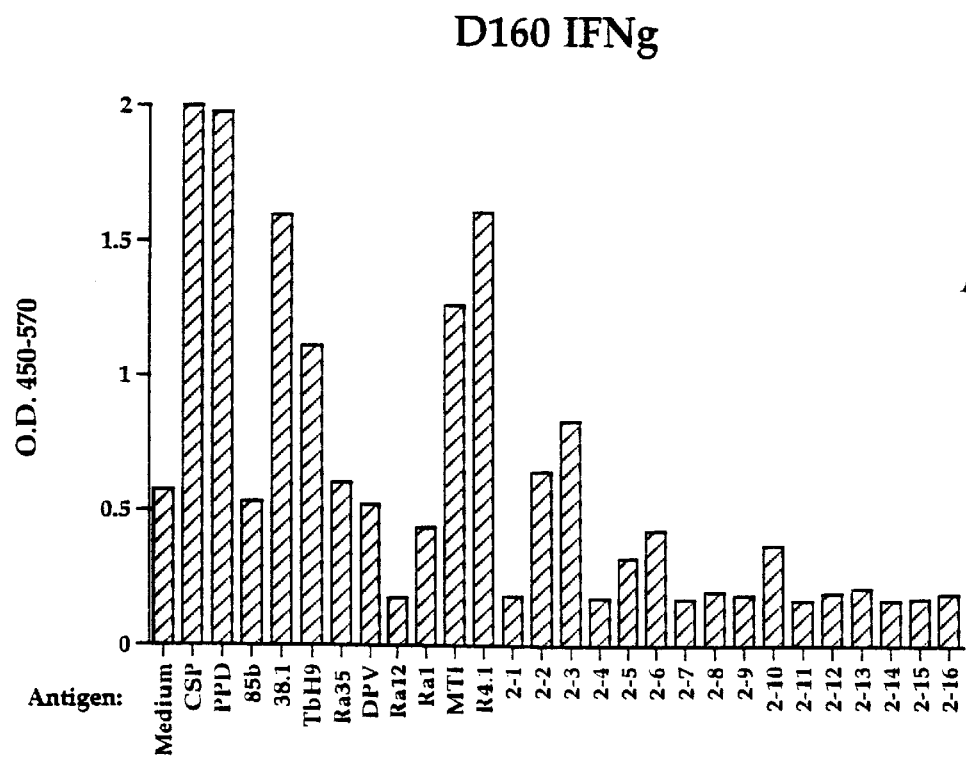

As noted above, the present invention is generally directed to compositions and methods for preventing, treating and diagnosing tuberculosis. The compositions of the subject invention include polypeptides that comprise at least one immunogenic portion of a *M. tuberculosis* antigen, or a variant of such an antigen that differs only in conservative substitutions and/or modifications. As used herein, the term "polypeptide" encompasses amino acid chains of any length, including full length proteins (i.e., antigens), wherein the amino acid residues are linked by covalent peptide bonds. Thus, a polypeptide comprising an immunogenic portion of one of the above antigens may consist entirely of the immunogenic portion, or may contain additional sequences. The additional sequences may be derived from the native *M. tuberculosis* antigen or may be heterologous, and such sequences may (but need not) be immunogenic.

"Immunogenic," as used herein, refers to the ability to elicit an immune response (e.g., cellular) in a patient, such as a human, and/or in a biological sample. In particular, antigens that are immunogenic (and immunogenic portions or other variants of such antigens) are capable of stimulating cell proliferation, interleukin-12 production and/or interferon-γ production in biological samples comprising one or more cells selected from the group of T cells, NK cells, B cells and macrophages, where the cells are derived from an *M. tuberculosis*-immune individual. Polypeptides comprising at least an immunogenic portion of one or more *M. tuberculosis* antigens may generally be used to detect tuberculosis or to induce protective immunity against tuberculosis in a patient.

The compositions and methods of this invention also encompass variants of the above polypeptides. A polypeptide "variant," as used herein, is a polypeptide that differs from the recited polypeptide only in conservative substitutions and/or modifications, such that the therapeutic, antigenic and/or immunogenic properties of the polypeptide are retained. Polypeptide variants preferably exhibit at least about 70%, more preferably at least about 90% and most preferably at least about 95% identity to the identified polypeptides. For polypeptides with immunoreactive properties, variants may, alternatively, be identified by modifying the amino acid sequence of one of the above polypeptides, and evaluating the immunoreactivity of the modified polypeptide. For polypeptides useful for the generation of diagnostic binding agents, a variant may be identified by evaluating a modified polypeptide for the ability to generate antibodies that detect the presence or absence of tuberculosis. Alternatively, variants of the claimed antigens that may be usefully employed in the inventive diagnostic methods may be identified by evaluating modified polypeptides for their ability to detect antibodies present in the sera of tuberculosis-infected patients. Such modified sequences may be prepared and tested using, for example, the representative procedures described herein.

A "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also (or alternatively) be modified by, for example, the deletion or addition of amino acids that have minimal influence on the immunogenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

In general, *M. tuberculosis* antigens, and DNA sequences encoding such antigens, may be prepared using any of a variety of procedures. For example, genomic or cDNA libraries derived from *M. tuberculosis* may be screened directly using peripheral blood mononuclear cells (PBMCs) or T cell lines or clones derived from one or more *M. tuberculosis*-immune individuals. Direct library screens may generally be performed by assaying pools of expressed recombinant proteins for the ability of induce proliferation and/or interferon-γ production in T cells derived from an *M. tuberculosis*-immune individual. Potential T cell antigens may be first selected based on antibody reactivity, as described above.

Alternatively, DNA sequences encoding antigens may be identified by screening an appropriate *M. tuberculosis* genomic or cDNA expression library with sera obtained from patients infected with *M. tuberculosis*. Such screens may generally be performed using techniques well known to those of ordinary skill in the art, such as those described in Sambrook et al., *Molecular Cloning: A Laboratory Manual,* Cold Spring Harbor Laboratories, Cold Spring Harbor, N.Y., 1989.

Purified antigens are then evaluated for their ability to elicit an appropriate immune response (e.g., cellular) using, for example, the representative methods described herein. Immunogenic antigens may then be partially sequenced using techniques such as traditional Edman chemistry. See Edman and Berg, *Eur. J. Biochem.* 80:116–132, 1967. Immunogenic antigens may also be produced recombinantly using a DNA sequence that encodes the antigen, which has been inserted into an expression vector and expressed in an appropriate host.

DNA sequences encoding the inventive antigens may also be obtained by screening an appropriate *M. tuberculosis* cDNA or genomic DNA library for DNA sequences that hybridize to degenerate oligonucleotides derived from partial amino acid sequences of isolated antigens. Degenerate oligonucleotide sequences for use in such a screen may be designed and synthesized, and the screen may be performed, as described (for example) in Sambrook et al., *Molecular Cloning: A Laboratory Manual,* Cold Spring Harbor Laboratories, Cold Spring Harbor, N.Y., 1989 (and references cited therein). Polymerase chain reaction (PCR) may also be employed, using the above oligonucleotides in methods well known in the art, to isolate a nucleic acid probe from a cDNA or genomic library. The library screen may then be performed using the isolated probe.

Regardless of the method of preparation, the antigens described herein are "antigenic." More specifically, the antigens have the ability to react with sera obtained from an *M. tuberculosis*-infected individual. Reactivity may be evaluated using, for example, the representative ELISA assays described herein, where an absorbance reading with sera from infected individuals that is at least three standard deviations above the absorbance obtained with sera from uninfected individuals is considered positive.

Antigenic portions of *M. tuberculosis* antigens may be prepared and identified using well known techniques, such as those summarized in Paul, *Fundamental Immunology,* 3d ed., Raven Press, 1993, pp. 243–247 and references cited therein. Such techniques include screening polypeptide portions of the native antigen for antigenic properties. The representative ELISAs described herein may generally be employed in these screens. An antigenic portion of a polypeptide is a portion that, within such representative assays, generates a signal in such assays that is substantially similar to that generated by the full length antigen. In other words, an antigenic portion of a *M. tuberculosis* antigen generates at least about 20%, and preferably about 100%, of the signal induced by the full length antigen in a model ELISA as described herein.

Portions and other variants of *M. tuberculosis* antigens may be generated by synthetic or recombinant means. Synthetic polypeptides having fewer than about 100 amino acids, and generally fewer than about 50 amino acids, may be generated using techniques well known in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963.

Equipment for automated synthesis of polypeptides is commercially available from suppliers such as Applied BioSystems, Inc., Foster City, Calif., and may be operated according to the manufacturer's instructions. Variants of a native antigen may generally be prepared using standard mutagenesis techniques, such as oligonucleotide-directed site-specific mutagenesis. Sections of the DNA sequence may also be removed using standard techniques to permit preparation of truncated polypeptides.

Recombinant polypeptides containing portions and/or variants of a native antigen may be readily prepared from a DNA sequence encoding the polypeptide using a variety of techniques well known to those of ordinary skill in the art. For example, supernatants from suitable host/vector systems which secrete recombinant protein into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant protein.

Any of a variety of expression vectors known to those of ordinary skill in the art may be employed to express recombinant polypeptides as described herein. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli,* yeast or a mammalian cell line, such as COS or CHO. The DNA sequences expressed in this manner may encode naturally occurring antigens, portions of naturally occurring antigens, or other variants thereof.

In general, regardless of the method of preparation, the polypeptides disclosed herein are prepared in substantially pure form. Preferably, the polypeptides are at least about 80% pure, more preferably at least about 90% pure and most preferably at least about 99% pure. For use in the methods described herein, however, such substantially pure polypeptides may be combined.

In one embodiment, the subject invention discloses polypeptides comprising at least an antigenic portion of a *M. tuberculosis* antigen (or a variant of such an antigen) that comprises one or more of the amino acid sequences encoded by (a) the DNA sequences of SEQ ID NO: 1–12, 83, 102–108, 125, 127–137, 139 and 140, (b) the complements of such DNA sequences or (c) DNA sequences substantially homologous to a sequence in (a) or (b). In a related embodiment, the present invention provides polypeptides comprising at least an immunogenic portion of an *M. tuberculosis* antigen having an amino acid sequence selected from the group consisting of sequences provided in SEQ ID NO: 16–33, 109, 126, 138, 141, 142 and variants thereof.

The *M. tuberculosis* antigens provided herein include variants that are encoded by DNA sequences which are substantially homologous to one or more of DNA sequences specifically recited herein. "Substantial homology," as used herein, refers to DNA sequences that are capable of hybridizing under moderately stringent conditions. Suitable moderately stringent conditions include prewashing in a solution of 5×SSC, 0.5% SDS, 1.0 mM EDTA (pH 8.0); hybridizing at 50° C.–65° C., 5×SSC, overnight or, in the event of cross-species homology, at 45° C. with 0.5×SSC; followed by washing twice at 65° C. for 20 minutes with each of 2×, 0.5× and 0.2×SSC containing 0.1% SDS). Such hybridizing DNA sequences are also within the scope of this invention, as are nucleotide sequences that, due to code degeneracy, encode an immunogenic polypeptide that is encoded by a hybridizing DNA sequence.

In a related aspect, the present invention provides fusion proteins comprising a first and a second inventive polypeptide or, alternatively, a polypeptide of the present invention and a known *M. tuberculosis* antigen, such as the 38 kD antigen described in Andersen and Hansen, *Infect. Immun.* 57:2481–2488, 1989, (Genbank Accession No. M30046), or ESAT-6 previously identified in *M. bovis* (Accession No. U34848) and in *M. tuberculosis* (Sorensen et al., *Infec. Immun.* 63:1710–1717, 1995). Variants of such fusion proteins are also provided. The fusion proteins of the present invention may include a linker peptide between the first and second polypeptides.

A DNA sequence encoding a fusion protein of the present invention is constructed using known recombinant DNA techniques to assemble separate DNA sequences encoding the first and second polypeptides into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8562, 1986; U.S. Pat. No. 4,935,233 and U.S. Pat. No. 4,751,180. The linker sequence may be from 1 to about 50 amino acids in length. Peptide linker sequences are not required when the first and second polypeptides have non-essential N-terminal amino acid regions that can be used to separate the functional domains and prevent steric hindrance.

In another aspect, the present invention provides methods for using the polypeptides described above to diagnose tuberculosis. In this aspect, methods are provided for detecting *M. tuberculosis* infection in a biological sample, using one or more of the above polypeptides, alone or in combination. In embodiments in which multiple polypeptides are employed, polypeptides other than those specifically described herein, such as the 38 kD antigen described above, may be included. As used herein, a "biological sample" is any antibody-containing sample obtained from a patient. Preferably, the sample is whole blood, sputum, serum, plasma, saliva, cerebrospinal fluid or urine. More preferably, the sample is a blood, serum or plasma sample obtained from a patient or a blood supply. The polypeptide(s) are used in an assay, as described below, to determine the presence or absence of antibodies to the polypeptide(s) in the sample, relative to a predetermined cut-off value. The presence of such antibodies indicates previous sensitization to mycobacterial antigens which may be indicative of tuberculosis.

In embodiments in which more than one polypeptide is employed, the polypeptides used are preferably complementary (i.e., one component polypeptide will tend to detect infection in samples where the infection would not be detected by another component polypeptide). Complementary polypeptides may generally be identified by using each polypeptide individually to evaluate serum samples obtained from a series of patients known to be infected with *M. tuberculosis*. After determining which samples test positive (as described below) with each polypeptide, combinations of two or more polypeptides may be formulated that are capable of detecting infection in most, or all, of the samples tested. Such polypeptides are complementary. For example, approximately 25–30% of sera from tuberculosis-infected individuals are negative for antibodies to any single protein, such as the 38 kD antigen mentioned above. Complementary polypeptides may, therefore, be used in combination with the 38 kD antigen to improve sensitivity of a diagnostic test.

There are a variety of assay formats known to those of ordinary skill in the art for using one or more polypeptides to detect antibodies in a sample. See, e.g., Harlow and Lane, *Antibodies: A Laboratory Manual,* Cold Spring Harbor Laboratory, 1988, which is incorporated herein by reference. In a preferred embodiment, the assay involves the use of polypeptide immobilized on a solid support to bind to and remove the antibody from the sample. The bound antibody may then be detected using a detection reagent that contains a reporter group. Suitable detection reagents include antibodies that bind to the antibody/polypeptide complex and free polypeptide labeled with a reporter group (e.g., in a semi-competitive assay). Alternatively, a competitive assay may be utilized, in which an antibody that binds to the polypeptide is labeled with a reporter group and allowed to bind to the immobilized antigen after incubation of the antigen with the sample. The extent to which components of the sample inhibit the binding of the labeled antibody to the polypeptide is indicative of the reactivity of the sample with the immobilized polypeptide.

The solid support may be any solid material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptides may be bound to the solid support using a variety of techniques known to those of ordinary skill in the art, which are amply described in the patent and scientific literature. In the context of the present invention, the term "bound" refers to both noncovalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide ranging from about 10 ng to about 1 $\mu$g, and preferably about 100 ng, is sufficient to bind an adequate amount of antigen.

Covalent attachment of polypeptide to a solid support may generally be achieved by first reacting the support with a bifunctional reagent that will react with both the support and a functional group, such as a hydroxyl or amino group, on the polypeptide. For example, the polypeptide may be bound to supports having an appropriate polymer coating using benzoquinone or by condensation of an aldehyde group on the support with an amine and an active hydrogen on the polypeptide (see, e.g., Pierce Immunotechnology Catalog and Handbook, 1991, at A12–A13).

In certain embodiments, the assay is an enzyme linked immunosorbent assay (ELISA). This assay may be performed by first contacting a polypeptide antigen that has been immobilized on a solid support, commonly the well of a microtiter plate, with the sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

More specifically, once the polypeptide is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.) may be employed. The immobilized polypeptide is then incubated with the sample, and antibody is allowed to bind to the antigen. The sample may be diluted with a suitable diluent, such as phosphate-buffered saline (PBS) prior to incubation. In general, an appropriate contact time (i.e., incubation time) is that period of time that is sufficient to detect the presence of antibody within a *M. tuberculosis*-infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. Detection reagent may then be added to the solid support. An appropriate detection reagent is any compound that binds to the immobilized antibody-polypeptide complex and that can be detected by any of a variety of means known to those in the art. Preferably, the detection reagent contains a binding agent (such as, for example, Protein A, Protein G, immunoglobulin, lectin or free antigen) conjugated to a reporter group. Preferred reporter groups include enzymes (such as horseradish peroxidase), substrates, cofactors, inhibitors, dyes, radionuclides, luminescent groups, fluorescent groups and biotin. The conjugation of binding agent to reporter group may be achieved using standard methods known to those of ordinary skill in the art. Common binding agents may also be purchased conjugated to a variety of reporter groups from many commercial sources (e.g., Zymed Laboratories, San Francisco, Calif., and Pierce, Rockford, Ill.).

The detection reagent is then incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of anti-*M. tuberculosis* antibodies in the sample, the signal detected from the reporter group that remains bound to the solid support is generally compared to a signal that corresponds to a predetermined cut-off value. In one preferred embodiment, the cut-off value is the average mean signal obtained when the immobilized antigen is incubated with samples from an uninfected patient. In general, a sample generating a signal that is three standard deviations above the predetermined cut-off value is considered positive for tuberculosis. In an alternate preferred embodiment, the cut-off value is determined using a Receiver Operator Curve, according to the method of Sackett et al., *Clinical Epidemiology: A Basic Science for Clinical Medicine,* Little Brown and Co., 1985, pp. 106–107. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for tuberculosis.

In a related embodiment, the assay is performed in a rapid flow-through or strip test format, wherein the antigen is immobilized on a membrane, such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide is bound is immersed in a solution containing the sample. The sample migrates along the membrane through a region containing detection reagent and to the area of immobilized polypeptide. Concentration of detection reagent at the polypeptide indicates the presence of anti-*M. tuberculosis* antibodies in the sample. Typically, the concentration of detection reagent at that site generates a pattern, such as a line, that can be read visually. The absence of such a pattern indicates a negative result. In general, the amount of polypeptide immobilized on the membrane is selected to generate a visually discernible pattern when the biological sample contains a level of antibodies that would be sufficient to generate a positive signal in an ELISA, as discussed above. Preferably, the amount of polypeptide immobilized on the membrane ranges from about 25 ng to about 1 μg, and more preferably from about 50 ng to about 500 ng. Such tests can typically be performed with a very small amount (e.g., one drop) of patient serum or blood.

Of course, numerous other assay protocols exist that are suitable for use with the polypeptides of the present invention. The above descriptions are intended to be exemplary only.

In yet another aspect, the present invention provides antibodies to the inventive polypeptides. Antibodies may be prepared by any of a variety of techniques known to those of ordinary skill in the art. See, e.g., Harlow and Lane, *Antibodies: A Laboratory Manual*, Cold Spring Harbor Laboratory, 1988. In one such technique, an immunogen comprising the antigenic polypeptide is initially injected into any of a wide variety of mammals (e.g., mice, rats, rabbits, sheep and goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Antibodies may be used in diagnostic tests to detect the presence of *M. tuberculosis* antigens using assays similar to those detailed above and other techniques well known to those of skill in the art, thereby providing a method for detecting *M. tuberculosis* infection in a patient.

Diagnostic reagents of the present invention may also comprise DNA sequences encoding one or more of the above polypeptides, or one or more portions thereof. For example, at least two oligonucleotide primers may be employed in a polymerase chain reaction (PCR) based assay to amplify *M. tuberculosis*-specific cDNA derived from a biological sample, wherein at least one of the oligonucleotide primers is specific for a DNA molecule encoding a polypeptide of the present invention. The presence of the amplified cDNA is then detected using techniques well known in the art, such as gel electrophoresis. Similarly, oligonucleotide probes specific for a DNA molecule encoding a polypeptide of the present invention may be used in a hybridization assay to detect the presence of an inventive polypeptide in a biological sample.

As used herein, the term "oligonucleotide primer/probe specific for a DNA molecule" means an oligonucleotide sequence that has at least about 80%, preferably at least about 90% and more preferably at least about 95%, identity to the DNA molecule in question. Oligonucleotide primers and/or probes which may be usefully employed in the inventive diagnostic methods preferably have at least about 10–40 nucleotides. In a preferred embodiment, the oligonucleotide primers comprise at least about 10 contiguous nucleotides of a DNA molecule encoding one of the polypeptides disclosed herein. Preferably, oligonucleotide probes for use in the inventive diagnostic methods comprise at least about 15 contiguous oligonucleotides of a DNA molecule encoding one of the polypeptides disclosed herein. Techniques for both PCR based assays and hybridization assays are well known in the art (see, for example, Mullis et al. Ibid; Ehrlich, Ibid). Primers or probes may thus be used to detect *M. tuberculosis*-specific sequences in biological samples. DNA probes or primers comprising oligonucleotide sequences described above may be used alone, in combination with each other, or with previously identified sequences, such as the 38 kD antigen discussed above.

The following Examples are offered by way of illustration and not by way of limitation.

EXAMPLES

Example 1

Purification and Characterization of *M. tuberculosis* Polypeptides Using CD4+ T Cell Lines Generated from Human PBMC

*M. tuberculosis* antigens of the present invention were isolated by expression cloning of cDNA libraries of *M. tuberculosis* strains H37Rv and Erdman essentially as described by Sanderson et al. (*J. Exp. Med.,* 1995, 182:1751–1757) and were shown to induce PBMC proliferation and IFN-γ in an immunoreactive T cell line.

Two CD4+ T cell lines, referred to as DC-4 and DC-5, were generated against dendritic cells infected with *M. tuberculosis.* Specifically, dendritic cells were prepared from adherent PBMC from a single donor and subsequently infected with tuberculosis. Lymphocytes from the same donor were cultured under limiting dilution conditions with the infected dendritic cells to generate the CD4+ T cell lines DC-4 and DC-5. These cell lines were shown to react with crude soluble proteins from *M. tuberculosis* but not with Tb38-1. Limiting dilution conditions were employed to obtain a third CD4+ T cell line, referred to as DC-6, which was shown to react with both crude soluble proteins and Tb38-1.

Genomic DNA was isolated from the M. tuberculosis strains H37Rv and Erdman and used to construct expression libraries in the vector pBSK(−) using the Lambda ZAP expression system (Stratagene, La Jolla, Calif.). These libraries were transformed into *E. coli*, pools of induced *E. coli* cultures were incubated with dendritic cells, and the ability of the resulting incubated dendritic cells to stimulate cell proliferation and IFN-γ production in the CD4+ T cell line DC-6 was examined as described below in Example 2. Positive pools were fractionated and re-tested until pure *M. tuberculosis* clones were obtained.

Nineteen clones were isolated, of which nine were found to contain the previously identified *M. tuberculosis* antigens TbH-9 and Tb38-1, disclosed in U.S. patent application Ser. No. 08/533,634. The determined cDNA sequences for the remaining ten clones (hereinafter referred to as Tb224, Tb636, Tb424, Tb436, Tb398, Tb508, Tb441, Tb475, Tb488 and Tb465) are provided in SEQ ID No: 1–10, respectively. The corresponding predicted amino acid sequences for Tb224 and Tb636 are provided in SEQ ID NO: 13 and 14, respectively. The open reading frames for these two antigens were found to show some homology to TbH-9. Tb224 and Tb636 were also found to be overlapping clones.

Tb424, Tb436, Tb398, Tb508, Tb441, Tb475, Tb488 and Tb465 were each found to contain two small open reading frames (referred to as ORF-1 and ORF-2) or truncated forms thereof, with minor variations in ORF-1 and ORF-2 being found for each clone. The predicted amino acid sequences of ORF-1 and ORF-2 for Tb424, Tb436, Tb398, Tb508, Tb441, Tb475, Tb488 and Tb465 are provided in SEQ ID NO: 16 and 17, 18 and 19, 20 and 21, 22 and 23, 24 and 25, 26 and 27, 28 and 29, and 30 and 31, respectively. In addition, clones Tb424 and Tb436 were found to contain a third apparent open reading frame, referred to as ORF-U. The predicted amino acid sequences of ORF-U for Tb424 and Tb436 are provided in SEQ ID NO: 32 and 33, respectively. Tb424 and Tb436 were found to be either overlapping clones or recently duplicated/transposed copies. Similarly Tb398, Tb508 and Tb465 were found to be either overlapping clones or recently duplicated/transposed copies, as were Tb475 and Tb488.

These sequences were compared with known sequences in the gene bank using the BLASTN system. No homologies to the antigens Tb224 and Tb431 were found. Tb636 was found to be 100% identical to a cosmid previously identified in *M. tuberculosis*. Similarly, Tb508, Tb488, Tb398, Tb424, Tb436, Tb441, Tb465 and Tb475 were found to show homology to known *M. tuberculosis* cosmids. In addition, Tb488 was found to have 100% homology to M. tuberculosis topoisomerase I.

Seventeen overlapping peptides to the open reading frames ORF-1 (referred to as 1-1–1-17; SEQ ID NO: 34–50, respectively) and thirty overlapping peptides to the open reading frame ORF-2 (referred to as 2-1–2-30, SEQ ID NO: 51–80) were synthesized using the procedure described below in Example 3.

The ability of the synthetic peptides, and of recombinant ORF-1 and ORF-2, to induce T cell proliferation and IFN-γ production in PBMC from PPD-positive donors was assayed as described below in Example 2. FIGS. 1A–B and 2A–B illustrate stimulation of T cell proliferation and IFN-γ by recombinant ORF-2 and the synthetic peptides 2-1–2-16 for two donors, referred to as D7 and D160, respectively. Recombinant ORF-2 (referred to as MTI) stimulated T cell proliferation and IFN-γ production in PBMC from both donors. The amount of PBMC stimulation seen with the individual synthetic peptides varied with each donor, indicating that each donor recognizes different epitopes on ORF2. The proteins encoded by ORF-1, ORF-2 and ORF-U were subsequently named MTS, MTI and MSF, respectively.

Eighteen overlapping peptides to the sequence of MSF (referred to as MSF-1–MSF-18; SEQ ID NO: 84–101, respectively) were synthesized and their ability to stimulate T cell proliferation and IFN-γ production in a CD4+ T cell line generated against *M. tuberculosis* culture filtrate was examined as described below. The peptides referred to as MSF-12 and MSF-13 (SEQ ID NO: 95 and 96, respectively) were found to show the highest levels of reactivity.

Two overlapping peptides (SEQ ID NO:81 and 82) to the open reading frame of Tb224 were synthesized and shown to induce T cell proliferation and IFN-γ production in PBMC from PPD-positive donors.

Two CD4+ T cell lines from different donors were generated against *M. tuberculosis* infected dendritic cells using the above methodology. Screening of the *M. tuberculosis* cDNA expression library described above using this cell line, resulted in the isolation of two clones referred to as Tb867 and Tb391. The determined cDNA sequence for Tb867 (SEQ ID NO: 102) was found to be identical to the previously isolated *M. tuberculosis* cosmid SCY22G10, with the candidate reactive open reading frame encoding a 750 amino acid *M. tuberculosis* protein kinase. Comparison of the determined cDNA sequence for Tb391 (SEQ ID NO: 103) with those in the gene bank revealed no significant homologies to known sequences.

In further studies, CD4+ T cell lines were generated against *M. tuberculosis* culture filtrate, essentially as outlined above, and used to screen the *M. tuberculosis* Erdman cDNA expression library described above. Five reactive clones, referred to as Tb431, Tb472, Tb470, Tb838 and Tb962 were isolated. The determined cDNA sequences for Tb431, Tb472, Tb470, and Tb838 are provided in SEQ ID NO: 11, 12, 104 and 105, respectively, with the determined cDNA sequences for Tb962 being provided in SEQ ID NO: 106 and 107. The corresponding predicted amino acid sequence for Tb431 is provided in SEQ ID NO: 15.

Subsequent studies led to the isolation of a full-length cDNA sequence for Tb472 (SEQ ID NO: 108). Overlapping peptides were synthesized and used to identify the reactive open reading frame. The predicted amino acid sequence for the protein encoded by Tb472 (referred to as MSL) is provided in SEQ ID NO: 109. Comparison of the sequences for Tb472 and MSL with those in the gene bank, as described above, revealed no homologies to known sequences. Fifteen overlapping peptides to the sequence of MSL (referred to as MSL-1–MSL-15; SEQ ID NO: 110–124, respectively) were synthesized and their ability to stimulate T cell proliferation and IFN-γ production in a CD4+ T cell line generated against *M. tuberculosis* culture filtrate was examined as described below. The peptides referred to as MSL-10 (SEQ ID NO: 119) and MSL-11 (SEQ ID NO: 120) were found to show the highest level of reactivity.

Comparison of the determined cDNA sequence for Tb838 with those in the gene bank revealed identity to the previously isolated *M. tuberculosis* cosmid SCY07H7. Comparison of the determined cDNA sequences for the clone Tb962 with those in the gene bank revealed some homology to two previously identified *M. tuberculosis* cosmids, one encoding a portion of bactoferritin. However, recombinant bactoferritin was not found to be reactive with the T cell line used to isolate Tb962.

The clone Tb470, described above, was used to recover a full-length open reading (SEQ ID NO: 125) that showed homology with TbH9 and was found to encode a 40 kDa antigen, referred to as Mtb40. The determined amino acid sequence for Mtb40 is provided in SEQ ID NO: 126. Similarly, subsequent studies led to the isolation of the full-length cDNA sequence for Tb431, provided in SEQ ID NO: 83, which was also determined to contain an open reading frame encoding Mtb40. Tb470 and Tb431 were also found to contain a potential open reading frame encoding a U-ORF-like antigen.

Screening of an M. tuberculosis Erdman cDNA expression library with multiple CD4+ T cell lines generated against M. tuberculosis culture filtrate, resulted in the isolation of three clones, referred to as Tb366, Tb433 and Tb439. The determined cDNA sequences for Tb366, Tb433 and Tb439 are provided in SEQ ID NO: 127, 128 and 129, respectively. Comparison of these sequences with those in the gene bank revealed no significant homologies to Tb366. Tb433 was found to show some homology to the previously identified M. tuberculosis antigen MPT83. Tb439 was found to show 100% identity to the previously isolated M. tuberculosis cosmid SCY02B10.

A CD4+ T cell line was generated against M. tuberculosis PPD, essentially described above, and used to screen the above M. tuberculosis Erdman cDNA expression library. One reactive clone (referred to as Tb372) was isolated, with the determined cDNA sequences being provided in SEQ ID NO: 130 and 131. Comparison of these sequences with those in the gene bank revealed no significnat homologies.

In further studies, screening of an M. tuberculosis cDNA expression library with a CD4+ T cell line generated against dendritic cells that had been infected with tuberculosis for 8 days, as described above, led to the isolation of two clones referred to as Tb390R5C6 and Tb390R2C11. The determined cDNA sequence for Tb390R5C6 is provided in SEQ ID NO: 132, with the determined cDNA sequences for Tb390R2C11 being provided in SEQ ID NO: 133 and 134. Tb390R5C6 was found to show 100% identity to a previously identified M. tuberculosis cosmid.

In subsequent studies, the methodology described above was used to screen an M. tuberculosis genomic DNA library prepared as follows. Genomic DNA from M. tuberculosis Erdman strain was randomly sheared to an average size of 2 kb, and blunt ended with Klenow polymerase, followed by the addition of EcoRI adaptors. The insert was subsequently ligated into the Screen phage vector (Novagen, Madison, Wis.) and packaged in vitro using the PhageMaker extract (Novagen). The phage library (referred to as the Erd λScreen library) was amplified and a portion was converted into a plasmid expression library by an autosubcloning mechanism using the E. coli strain BM25.8 (Novagen). Plasmid DNA was purified from BM25.8 cultures containing the pSCREEN recombinants and used to transform competent cells of the expressing host strain BL21(DE3)pLysS. Transformed cells were aliquoted into 96 well microtiter plates with each well containing a pool size of approximately 50 colonies. Replica plates of the 96 well plasmid library format were induced with IPTG to allow recombinant protein expression. Following induction, the plates were centrifuged to pellet the E. coli which was used directly in T cell expression cloning of a CD4+ T cell line prepared from a PPD-positive donor (donor 160) as described above. Pools containing E. coli expressing M. tuberculosis T cell antigens were subsequently broken down into individual colonies and reassayed in a similar fashion to identify positive hits.

Screening of the T cell line from donor 160 with one 96 well plate of the Erd λScreen library provided a total of nine positive hits. Previous experiments on the screening of the pBSK library described above with T cells from donor 160 suggested that most or all of the positive clones would be TbH-9, Tb38-1 or MTI (disclosed in U.S. patent application Ser. No. 08/533,634) or variants thereof. However, Southern analysis revealed that only three wells hybridized with a mixed probe of TbH-9, Tb38-1 and MTI. Of the remaining six positive wells, two were found to be identical. The determined 5' cDNA sequences for two of the isolated clones (referred to as Y1-26C1 and Y1-86C11) are provided in SEQ ID NO: 135 and 136, respectively. The full length cDNA sequence for the isolated clone referred to as hTcc#1 is provided in SEQ ID NO: 137, with the corresponding predicted amino acid sequence being provided in SEQ ID NO: 138. Comparison of the sequences of hTcc#1 to those in the gene bank as described above, revealed some homology to the previously isolated M. tuberculosis cosmid MTCY07H7B.06

Example 2

Induction of T Cell Proliferation and Interferon-γ Production by M. tuberculosis Antigens The ability of recombinant M. tuberculosis antigens to induce T cell proliferation and interferon-γ production may be determined as follows.

Proteins may be induced by IPTG and purified by gel elution, as described in Skeiky et al. J. Exp. Med., 1995, 181:1527–1537. The purified polypeptides are then screened for the ability to induce T-cell proliferation in PBMC preparations. The PBMCs from donors known to be PPD skin test positive and whose T-cells are known to proliferate in response to PPD, are cultured in medium comprising RPMI 1640 supplemented with 10% pooled human serum and 50 μg/ml gentamicin. Purified polypeptides are added in duplicate at concentrations of 0.5 to 10 μg/mL. After six days of culture in 96-well round-bottom plates in a volume of 200 μl, 50 μl of medium is removed from each well for determination of IFN-γ levels, as described below. The plates are then pulsed with 1 μCi/well of tritiated thymidine for a further 18 hours, harvested and tritium uptake determined using a gas scintillation counter. Fractions that result in proliferation in both replicates three fold greater than the proliferation observed in cells cultured in medium alone are considered positive.

IFN-γ is measured using an enzyme-linked immunosorbent assay (ELISA). ELISA plates are coated with a mouse monoclonal antibody directed to human IFN-γ (PharMingen, San Diego, Calif.) in PBS for four hours at room temperature. Wells are then blocked with PBS containing 5% (W/V) non-fat dried milk for 1 hour at room temperature. The plates are washed six times in PBS/0.2% TWEEN-20 and samples diluted 1:2 in culture medium in the ELISA plates are incubated overnight at room temperature. The plates are again washed and a polyclonal rabbit anti-human IFN-γ serum diluted 1:3000 in PBS/10% normal goat serum is added to each well. The plates are then incubated for two hours at room temperature, washed and horseradish peroxidase-coupled anti-rabbit IgG (Sigma Chemical So., St. Louis, Mo.) is added at a 1:2000 dilution in PBS/5% non-fat dried milk. After a further two hour incubation at room temperature, the plates are washed and TMB substrate added. The reaction is stopped after 20 min with 1 N sulfuric acid. Optical density is determined at 450 nm using 570 nm as a reference wavelength. Fractions that result in both replicates giving an OD two fold greater than the mean OD from cells cultured in medium alone, plus 3 standard deviations, are considered positive.

Example 3

Purification and Characterization of *M. tuberculosis* Polypeptides Using CD4+ T Cell Lines Generated from a Mouse *M. tuberculosis* Model Infection of C57BL/6 mice with *M. tuberculosis* results in the development of a progressive disease for approximately 2–3 weeks. The disease progression is then halted as a consequence of the emergence of a strong protective T cell-mediated immune response. This infection model was used to generate T cell lines capable of recognizing protective *M. tuberculosis* antigens.

Specifically, spleen cells were obtained from C57BL/6 mice infected with *M. tuberculosis* for 28 days and used to raise specific anti-*M. tuberculosis* T cell lines as described above. The resulting CD4+ T cell lines, in conjunction with normal antigen presenting (spleen) cells from C57BL/6 mice were used to screen the *M. tuberculosis* Erd γscreen library described above. One of the reactive library pools, which was found to be highly stimulatory of the T cells, was selected and the corresponding active clone (referred to as Y288C 10) was isolated.

Sequencing of the clone Y288C10 revealed that it contains two potential genes, in tandem. The determined cDNA sequences for these two genes (referred to as mTCC#1 and mTCC#2) are provided in SEQ ID NO: 139 and 140, respectively, with the corresponding predicted amino acid sequences being provided in SEQ ID NO: 141 and 142, respectively. Comparison of these sequences with those in the gene bank revealed identity to unknown sequences previously found within the *M. tuberculosis* cosmid MTY21C12. The predicted amino acid sequences of mTCC#1 and mTCC#2 were found to show some homology to previously identified members of the TbH9 protein family, discussed above.

Example 4

Synthesis of Synthetic Polypeptides

Polypeptides may be synthesized on a Millipore 9050 peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0–60% acetonitrile (containing 0.1% TFA) in water (containing 0.1% TFA) may be used to elute the peptides. Following lyophilization of the pure fractions, the peptides may be characterized using electrospray mass spectrometry and by amino acid analysis.

Example 5

Use of Representative Antigens for Serodiagnosis of Tuberculosis

The diagnostic properties of representative *M. tuberculosis* antigens may be determined by examining the reactivity of antigens with sera from tuberculosis-infected patients and from normal donors as described below.

Assays are performed in 96-well plates coated with 200 ng antigen diluted to 50 μL in carbonate coating buffer, pH 9.6. The wells are coated overnight at 4° C. (or 2 hours at 37° C.). The plate contents are then removed and the wells are blocked for 2 hours with 200 μL of PBS/1% BSA. After the blocking step, the wells are washed five times with PBS/0.1% Tween 20™. 50 μL sera, diluted 1:100 in PBS/0.1% Tween 20™/0.1% BSA, is then added to each well and incubated for 30 minutes at room temperature. The plates are washed again five times with PBS/0.1% Tween 20™.

The enzyme conjugate (horseradish peroxidase—Protein A, Zymed, San Francisco, Calif.) is then 1:10,000 in PBS/0.1% Tween 20™/0.1% BSA, and 50 μL of the diluted conjugate is added to each well and incubated for 30 minutes at room temperature. Following incubation, the wells are washed five times with PBS/0.1% Tween 20™. 100 μL of tetramethylbenzidine peroxidase (TMB) substrate (Kirkegaard and Perry Laboratories, Gaithersburg, Md.) is added, undiluted, and incubated for about 15 minutes. The reaction is stopped with the addition of 100 μL of 1 N $H_2SO_4$ to each well, and the plates are read at 450 nm.

From the foregoing, it will be appreciated that, although specific embodiments of the invention have been described herein for the purpose of illustration, various modifications may be made without deviating from the spirit and scope of the invention.

What is claimed is:

1. An isolated polypeptide comprising the amino acid sequence as set forth in SEQ ID NOs:126 or 142.

2. The polypeptide of claim 1, which is a soluble peptide.

3. The polypeptide of claim 1, which is produced by a recombinant DNA method.

4. The polypeptide of claim 1, which is produced by a chemical synthetic method.

5. The polypeptide of claim 1, which is purified from a cell source or culture supernatant.

6. The polypeptide of claim 1, which reacts with an antibody-containing biological sample.

7. The polypeptide of claim 1, which is a Mycobacterium tuberculosis antigen.

8. The polypeptide of claim 1, which is fused with a second heterologous polypeptide.

9. An isolated polypeptide from *Mycobacterium tuberculosis* encoded by a polynucleotide that hybridizes under moderately stringent conditions to a second polynucleotide that is complementary to the nucleotide sequence of SEQ ID NOs:125 or 140, wherein said moderately stringent conditions comprise prewashing in a solution of 5×SSC, 0.5% SDS, 1.0 mM EDTA (pH 8.0); hybridizing at 50–65° C. overnight in a solution comprising 5×SSC; and washing twice at 65° C. for 20 minutes with each of 2×, 0.5×, and 0.2×SSC containing 0.1% SDS.

10. The polypeptide of claim 9, encoded by a nucleic acid comprising nucleotide sequence of SEQ ID NOs:125 or 140.

11. The polypeptide of claim 9, comprising the amino acid sequence of SEQ ID NOs:126 or 142.

12. A composition comprising:

(a) an isolated polypeptide of claim 9, and (b) a physiologically acceptable carrier.

13. The composition of claim 12, further comprising an adjuvant.

* * * * *

SEQUENCE LISTING

```
(1) GENERAL INFORMATION:

(iii) NUMBER OF SEQUENCES: 144

(2) INFORMATION FOR SEQ ID NO:1:

(i) SEQUENCE CHARACTERISTICS:
          (A) LENGTH: 1886 base pairs
          (B) TYPE: nucleic acid
          (C) STRANDEDNESS: double
          (D) TOPOLOGY: linear (ii) MOLECULE TYPE: DNA (genomic)

(vi) ORIGINAL SOURCE:
```

(A) ORGANISM: Mycobacterium tuberculosis (xi) SEQUENCE DESCRIPTION: SEQ ID NO:1:

```
CGCTCTGGTG ACCACCAACT TCTTCGGTGT CAACACCATC CCGATCGCCC TCAACGAGGC     60
CGACTACCTG CGCATGTGGA TCCAGGCCGC CACCGTCATG AGCCACTATC AAGCCGTCGC    120
GCACGAAATC TGGTGTCTCC ATGAATANGC CAGTTCGGGA AAGCCGTGGG CCAGTATCAC    180
CACGGGTGCG CCGGGCTCAC CGGCCTCGAC CACTCGCAGT CGCACGCCGT TGGTATCAAC    240
TAACCGTNCN GTANGTGCGC CCATCGTCTC ACCAAATCAC ACCGGGCACC GGCCTGAGAA    300
GGGCTTGGGG AGCANCCAGA GGCGATTGTC GCGGGTGCTG CCGCGCATCA TTGATCGGCC    360
GGCCGGACCA NTCGGGCCTC CCTTGACGTC CGGATCNCAC TTCCTGTGCA GCTGGCATGG    420
CTACAGCTCA CAGTGACTGC CCCACGATTG CCGGCCAGGT CCAGTTCAAA TTCCGGTGAA    480
TTCGCGGACA AAAGCAGCAG GTCAACCAAC CGCAGTCAGT CGAGGGTCCC AAACGTGAGC    540
CAATCGGTGA AATGGCTTGC TGCAGTGACA CCGGTCACAG GCTTAGCCGA CAGCACCGGA    600
ATAGCTCAGG CGGGCTATAG AGTCCTATAG AAACATTTGC TGATAGAATT AACCGCTGTC    660
TTGGCGTGAT CTTGATACGG CTCGCCGTGC GACCGGTTGG CTCAGTAGCT GACCACCATG    720
TAACCCATCC TCGGCAGGTG TCTACTAAGG CGAGACACCG CATTGGTGGG GCTGCATCGC    780
AAATCGGTCC GAGCATGTAG CACTGCCGTT ATCCCGGGAT AGCAAACCAC CCGGAACCAG    840
GGCTATCCCA GTCGCTCTCC GACGGAGGCC GTTTCGCTTT CCGTTGCCCG ATAACTCCCG    900
AGTGGATATC GGCGTTATCA NATTCAGGCT TTTCTTCGCA AGGTACCGGT GTTCGCTATA    960
TTCGGATATC TCGGACGGAT AATTACTAAA ACTTCAGTGG TTTAGATAAG GCCGCCGCAA   1020
TACTTCGCCG ATCTTGCCGA GCGCAACGGA TTTCCATCGT CGGTTTTCGT CGCCTTATCA   1080
AACATGATCG GAGATAATGA CAGATCGGCC TAGCTAGGTG TTTAGCGGAC GCGATTTAGG   1140
ACAACCGAGA TTTGCTTTGC CTCGCAACCA TGAGAGCGCC CCGCTTCGAC GCCGAATCGG   1200
GTGAGTGATG GTGGGTTAGC ACAGCCCTGA TTGCGCCACC GGCGAGGTGA TTGTGCCCGC   1260
CACGAGGCCG CCGCCGGCTA GCCCCATGAG CACGNTATAT AGACTCTCCT GCAACAGATC   1320
TCATACCGAT CGAAGGCGAA GCGCAGGCAT CGACGTCGGA GACACTGCCT TGGGATCGCG   1380
CCGCCTACAC GGCGGTTGGC GCATTGTCGC AGCGCAGTTG CAGGAGGGCA AATGTGCGCA   1440
GACGATGTAG TCGACAACAA GTGNACATGC CGTCTTCACG AACTCAAAAC TGACGATCTG   1500
CTTAGCATGA AAAAACTGT TGACATCGGC CAAGCATGAC AGCCGACTG TAGGCCTACG   1560
CGTGCAATGC AGAACCAAGG NTATGCATGG AATCGACGAC CGTTGAGATA GGCGGCAGGC   1620
ATGAGCAGAG CGTTCATCAT CGATCCAACG ATCAGTGCCA TTGACGGCTT GTACGACCTT   1680
CTGGGGATTG GAATACCCAA CCAAGGGGGT ATCCTTTACT CCTCACTAGA GTACTTCGAA   1740
AAAGCCCTGG AGGAGCTGGC AGCAGCGTTT CCGGGTGATG GCTGGTTAGG TTCGGCCGCG   1800
GACAAATACG CCGGCAAAAA CCGCAACCAC GTGAATTTTT TCCAGGAACT GGCAGACCTC   1860
GATCGTCAGC TCATCAGCCT GATCCA                                        1886
```

(2) INFORMATION FOR SEQ ID NO:2:

(i) SEQUENCE CHARACTERISTICS:
        (A) LENGTH: 2305 base pairs
        (B) TYPE: nucleic acid
        (C) STRANDEDNESS: double
        (D) TOPOLOGY: linear (ii) MOLECULE TYPE: DNA (genomic)

-continued (vi) ORIGINAL SOURCE:
(A) ORGANISM: Mycobacterium tuberculosis (xi) SEQUENCE DESCRIPTION: SEQ ID NO:2:

GGCACGCGCT GGCCGCGCAA TACACCGAAA TTGCAACGGA ACTCGCAAGC GTGCTCGCTG 60

CGGTGCAGGC AAGCTCGTGG CAGGGGCCCA GCGCCGACCG GTTCGTCGTC GCCCATCAAC 120

CGTTCCGGTA TTGGCTAACC CACGCTGCCA CGGTGGCCAC CGCAGCAGCC GCCGCGCACN 180

AAACGGCCGC CGCCGGGTAT ACGTCCGCAT TGGGGGGCAT GCCTACGCTA GCCGAGTTGG 240

CGGCCAACCA TGCCATGCAC GGCGCTCTGG TGACCACCAA CTTCTTCGGT GTCAACACCA 300

TCCCGATCGC CCTCAACGAG GCCGACTACC TGCGCATGTG GATCCAGGCC GCCACCGTCA 360

TGAGCCACTA TCAAGCCGTC GCGCACGAAA GCGTGGCGGC GACCCCCAGC ACGCCGCCGG 420

CGCCGCAGAT AGTGACCAGT GCGGCCAGCT CGGCGGCTAG CAGCAGCTTC CCCGACCCGA 480

CCAAATTGAT CCTGCAGCTA CTCAAGGATT TCCTGGAGCT GCTGCGCTAT CTGGCTGTTG 540

AGCTGCTGCC GGGGCCGCTC GGCGACCTCA TCGCCCAGGT GTTGGACTGG TTCATCTCGT 600

TCGTGTCCGG TCCAGTCTTC ACGTTTCTCG CCTACCTGGT GCTGGACCCA CTGATCTATT 660

TCGGACCGTT CGCCCCGCTG ACGAGTCCGG TCCTGTTGCC TGCTGTGGAG TTACGCAACC 720

GCCTCAAAAC CGCCACCGGA CTGACGCTGC CACCTACCGT GATTTTCGAT CATCCCACTC 780

CCACTGCGGT CGCCGAGTAT GTCGCCCAGC AAATGTCTGG CAGCCGCCCA ACGGAATCCG 840

GTGATCCGAC GTCGCAGGTT GTCGAACCCG CTCGTGCCGA ATTCGGCACG AGTGCTGTTC 900

ATCAAATCCC CCCGAGACCT GCGGACACCC GGCGCGCTTG CCGACATCGA GATGATGTCC 960

CGCGAGATAG CAGAATTGCC CAACATCGTG ATGGTGCGGG GCTTGACCCG ACCGAACGGG 1020

GAACCTCTGA AGGAGACCAA GGTCTCGTTT CAGGCTGGTG AAGTGGGCGG CAAGCTCGAC 1080

GAAGCGACCA CCCTGCTCGA AGAGCACGGA GGCGAGCTGG ACCAGCTGAC CGGCGGTGCG 1140

CACCAGTTGG CCGACGCCCT CGCCCAAATA CGCAACGAAA TCAATGGGGC CGTGGCCAGC 1200

TCGAGCGGGA TAGTCAACAC CCTGCAGGCC ATGATGGACC TGATGGGCGG TGACAAGACC 1260

ATCCGACAAC TGGAAAATGC GTCCCAATAT GTCGGGCGCA TGCGGGCTCT GGGGGACAAT 1320

CTGAGCGGGA CCGTCACCGA TGCCGAACAA ATCGCCACTT GGGCCAGCCC TATGGTCAAC 1380

GCCCTCAACT CCAGCCCGGT GTGTAACAGC GATCCCGCCT GTCGGACGTC GCGCGCACAG 1440

TTGGCGGCGA TTGTCCAGGC GCAGGACGAC GGCCTGCTCA GGTCCATCAG AGCGCTAGCC 1500

GTCACCCTGC AACAGACGCA GGAATACCAG ACACTCGCCC GGACGGTGAG CACACTGGAC 1560

GGGCAACTGA AGCAAGTCGT CAGCACCCTC AAAGCGGTCG ACGGCCTACC CACCAAATTG 1620

GCTCAAATGC AGCAAGGAGC CAACGCTCTC GCCGACGGCA GCGCAGCGCT GGCGGCAGGC 1680

GTGCAGGAAT TGGTCGATCA GGTCAAAAAG ATGGGCTCAG GGCTCAACGA GGCCGCCGAC 1740

TTCCTGTTGG GGATCAAGCG GGATGCGGAC AAGCCGTCAA TGGCGGGCTT CAACATTCCA 1800

CCGCAGATTT TTTCGAGGGA CGAGTTCAAG AAGGGCGCCC AGATTTTCCT GTCGGCCGAT 1860

GGTCATGCGG CGCGGTACTT CGTGCAGAGC GCGCTGAATC CGGCCACCAC CGAGGCGATG 1920

GATCAGGTCA ACGATATCCT CCGTGTTGCG GATTCCGCGC GACCGAATAC CGAACTCGAG 1980

GATGCCACGA TAGGTCTGGC GGGGGTTCCG ACTGCGCTGC GGGATATCCG CGACTACTAC 2040

AACAGCGATA TGAAATTCAT CGTCATTGCG ACGATCGTTA TCGTATTCTT GATTCTCGTC 2100

ATTCTGNTGC GCGCACTTGT GGNTCCGATA TATCTGATAG GCTCGGTGCT GATTTCTTAC 2160

TTGTCGGCCC TAGGCATAGG AACTTTCGTT TTCCAATTGA TACTGGGCCA GGAAATGCAT 2220

| TGGAGCCTGC CGGGACTGTC CTTCATATTA TTGGTTGCCA TCGGCGCTGA CTACAACATG | 2280 |
| CTGCTCATTT CACGCATCCG CGACG | 2305 |

(2) INFORMATION FOR SEQ ID NO:3:

(i) SEQUENCE CHARACTERISTICS:
        (A) LENGTH: 1742 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Mycobacterium tuberculosis (xi) SEQUENCE DESCRIPTION: SEQ ID NO:3:

| CCGCTCTCTT TCAACGTCAT AAGTTCGGTG GGCCAGTCGG CCGCGCGTGC ATATGGCACC | 60 |
| AATAACGCGT GTCCCATGGA TACCCGGACC GCACGACGGT AGAGCGGATC AGCGCAGCCG | 120 |
| GTGCCGAACA CTACCGCGTC CACGCTCAGC CCTGCCGCGT TGCGGAAGAT CGAGCCCAGG | 180 |
| TTCTCATGGT CGTTAACGCC TTCCAACACT GCGACGGTGC GCGCCCCGGC GACCACCTGA | 240 |
| GCAACGCTCG GCTCCGGCAC CCGGCGCGCG GCTGCCAACA CCCCACGATT GAGATGGAAG | 300 |
| CCGATCACCC GTGCCATGAC ATCAGCCGAC GCTCGATAGT ACGGCGCGCC GACACCGGCC | 360 |
| AGATCATCCT TGAGCTCGGC CAGCCGGCGG TCGGTGCCGA ACAGCGCCAG CGGCGTGAAC | 420 |
| CGTGAGGCCA GCATGCGCTG CACCACCAGC ACACCCTCGG CGATCACCAA CGCCTTGCCG | 480 |
| GTCGGCAGAT CGGGACNACN GTCGATGCTG TTCAGGTCAC GGAAATCGTC GAGCCGTGGG | 540 |
| TCGTCGGGAT CGCAGACGTC CTGAACATCG AGGCCGTCGG GGTGCTGGGC ACAACGGCCT | 600 |
| TCGGTCACGG GCTTTCGTCG ACCAGAGCCA GCATCAGATC GGCGGCGCTG CGCAGGATGT | 660 |
| CACGCTCGCT GCGGTTCAGC GTCGCGAGCC GCTCAGCCAG CCACTCTTGC AGAGAGCCGT | 720 |
| TGCTGGGATT AATTGGGAGA GGAAGACAGC ATGTCGTTCG TGACCACACA GCCGGAAGCC | 780 |
| CTGGCAGCTG CGGCGGCGAA CCTACAGGGT ATTGGCACGA CAATGAACGC CCAGAACGCG | 840 |
| GCCGCGGCTG CTCCAACCAC CGGAGTAGTG CCCGCAGCCG CCGATGAAGT ATCAGCGCTG | 900 |
| ACCGCGGCTC AGTTTGCTGC GCACGCGCAG ATGTACCAAA CGGTCAGCGC CCAGGCCGCG | 960 |
| GCCATTCACG AAATGTTCGT GAACACGCTG GTGGCCAGTT CTGGCTCATA CGCGGCCACC | 1020 |
| GAGGCGGCCA ACGCAGCCGC TGCCGGCTGA ACGGGCTCGC ACGAACCTGC TGAAGGAGAG | 1080 |
| GGGGAACATC CGGAGTTCTC GGGTCAGGGG TTGCGCCAGC GCCCAGCCGA TTCAGNTATC | 1140 |
| GGCGTCCATA ACAGCAGACG ATCTAGGCAT TCAGTACTAA GGAGACAGGC AACATGGCCT | 1200 |
| CACGTTTTAT GACGGATCCG CATGCGATGC GGGACATGGC GGGCCGTTTT GAGGTGCACG | 1260 |
| CCCAGACGGT GGAGGACGAG GCTCGCCGGA TGTGGGCGTC CGCGCAAAAC ATTTCCGGTG | 1320 |
| CGGGCTGGAG TGGCATGGCC GAGGCGACCT CGCTAGACAC CATGACCTAG ATGAATCAGG | 1380 |
| CGTTTCGCAA CATCGTGAAC ATGCTGCACG GGTGCGTGA CGGGCTGGTT CGCGACGCCA | 1440 |
| ACAANTACGA ACAGCAAGAG CAGGCCTCCC AGCAGATCCT GAGCAGNTAG CGCCGAAAGC | 1500 |
| CACAGCTGNG TACGNTTTCT CACATTAGGA GAACACCAAT ATGACGATTA ATTACCAGTT | 1560 |
| CGGGGACGTC GACGCTCATG GCGCCATGAT CCGCGCTCAG GCGGCGTCGC TTGAGGCGGA | 1620 |
| GCATCAGGCC ATCGTTCGTG ATGTGTTGGC CGCGGGTGAC TTTTGGGGCG CGCCGGTTC | 1680 |
| GGTGGCTTGC CAGGAGTTCA TTACCCAGTT GGGCCGTAAC TTCAGGTGA TCTACAGCA | 1740 |
| GG | 1742 |

(2) INFORMATION FOR SEQ ID NO:4:

(i) SEQUENCE CHARACTERISTICS:
        (A) LENGTH: 2836 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Mycobacterium tuberculosis (xi) SEQUENCE DESCRIPTION: SEQ ID NO:4:

```
GTTGATTCCG TTCGCGGCGC CGCCGAAGAC CACCAACTCC GCTGGGGTGG TCGCACAGGC      60
GGTTGCGTCG GTCAGCTGGC CGAATCCCAA TGATTGGTGG CTCNGTGCGG TTGCTGGGCT     120
CGATTACCCC CACGGAAAGG ACGACGATCG TTCGTTTGCT CGGTCAGTCG TACTTGGCGA     180
CGGGCATGGC GCGGTTTCTT ACCTCGATCG CACAGCAGCT GACCTTCGGC CCAGGGGGCA     240
CAACGGCTGG CTCCGGCGGA GCCTGGTACC CAACGCCACA ATTCGCCGGC CTGGGTGCAG     300
GCCCGGCGGT GTCGGCGAGT TTGGCGCGGG CGGAGCCGGT CGGGAGGTTG TCGGTGCCGC     360
CAAGTTGGGC CGTCGCGGCT CCGGCCTTCG CGGAGAAGCC TGAGGCGGGC ACGCCGATGT     420
CCGTCATCGG CGAAGCGTCC AGCTGCGGTC AGGGAGGCCT GCTTCGAGGC ATACCGCTGG     480
CGAGAGCGGG GCGGCGTACA GGCGCCTTCG CTCACCGATA CGGGTTCCGC CACAGCGTGA     540
TTACCCGGTC TCCGTCGGCG GGATAGCTTT CGATCCGGTC TGCGCGGCCG CCGGAAATGC     600
TGCAGATAGC GATCGACCGC GCCGGTCGGT AAACGCCGCA CACGGCACTA TCAATGCGCA     660
CGGCGGGCGT TGATGCCAAA TTGACCGTCC CGACGGGGCT TTATCTGCGG CAAGATTTCA     720
TCCCCAGCCC GGTCGGTGGG CCGATAAATA CGCTGGTCAG CGCGACTCTT CCGGCTGAAT     780
TCGATGCTCT GGGCGCCCGC TCGACGCCGA GTATCTCGAG TGGGCCGCAA ACCCGGTCAA     840
ACGCTGTTAC TGTGGCGTTA CCACAGGTGA ATTTGCGGTG CCAACTGGTG AACACTTGCG     900
AACGGGTGGC ATCGAAATCA ACTTGTTGCG TTGCAGTGAT CTACTCTCTT GCAGAGAGCC     960
GTTGCTGGGA TTAATTGGGA GAGGAAGACA GCATGTCGTT CGTGACCACA CAGCCGGAAG    1020
CCCTGGCAGC TGCGGCGGCG AACCTACAGG GTATTGGCAC GACAATGAAC GCCCAGAACG    1080
CGGCCGCGGC TGCTCCAACC ACCGGAGTAG TGCCCGCAGC CGCCGATGAA GTATCAGCGC    1140
TGACCGCGGC TCAGTTTGCT GCGCACGCGC AGATGTACCA AACGGTCAGC GCCCAGGCCG    1200
CGGCCATTCA CGAAATGTTC GTGAACACGC TGGTGGCCAG TTCTGGCTCA TACGCGGCCA    1260
CCGAGGCGGC CAACGCAGCC GCTGCCGGCT GAACGGGCTC GCACGAACCT GCTGAAGGAG    1320
AGGGGGAACA TCCGGAGTTC TCGGGTCAGG GGTTGCGCCA GCGCCCAGCC GATTCAGCTA    1380
TCGGCGTCCA TAACAGCAGA CGATCTAGGC ATTCAGTACT AAGGAGACAG GCAACATGGC    1440
CTCACGTTTT ATGACGGATC CGCATGCGAT GCGGGACATG GCGGGCCGTT TGAGGTGCA     1500
CGCCCAGACG GTGGAGGACG AGGCTCGCCG GATGTGGGCG TCCGCGCAAA ACATTTCCGG    1560
TGCGGGCTGG AGTGGCATGG CCGAGGCGAC CTCGCTAGAC ACCATGACCT AGATGAATCA    1620
GGCGTTTCGC AACATCGTGA ACATGCTGCA CGGGGTGCGT GACGGGCTGG TTCGCGACGC    1680
CAACAACTAC GAACAGCAAG AGCAGGCCTC CCAGCAGATC CTGAGCAGCT AGCGCCGAAA    1740
GCCACAGCTG CGTACGCTTT CTCACATTAG GAGAACACCA ATATGACGAT TAATTACCAG    1800
TTCGGGGACG TCGACGCTCA TGGCGCCATG ATCCGCGCTC AGGCGGCGTC GCTTGAGGCG    1860
```

-continued

```
GAGCATCAGG CCATCGTTCG TGATGTGTTG GCCGCGGGTG ACTTTTGGGG CGGCGCCGGT      1920

TCGGTGGCTT GCCAGGAGTT CATTACCCAG TTGGGCCGTA ACTTCCAGGT GATCTACGAG      1980

CAGGCCAACG CCCACGGGCA GAAGGTGCAG GCTGCCGGCA ACAACATGGC GCAAACCGAC      2040

AGCGCCGTCG GCTCCAGCTG GGCCTAAAAC TGAACTTCAG TCGCGGCAGC ACACCAACCA      2100

GCCGGTGTGC TGCTGTGTCC TGCAGTTAAC TAGCACTCGA CCGCTGAGGT AGCGATGGAT      2160

CAACAGAGTA CCCGCACCGA CATCACCGTC AACGTCGACG GCTTCTGGAT GCTTCAGGCG      2220

CTACTGGATA TCCGCCACGT TGCGCCTGAG TTACGTTGCC GGCCGTACGT CTCCACCGAT      2280

TCCAATGACT GGCTAAACGA GCACCCGGGG ATGGCGGTCA TGCGCGAGCA GGGCATTGTC      2340

GTCAACGACG CGGTCAACGA ACAGGTCGCT GCCCGGATGA AGGTGCTTGC CGCACCTGAT      2400

CTTGAAGTCG TCGCCCTGCT GTCACGCGGC AAGTTGCTGT ACGGGTCAT AGACGACGAG       2460

AACCAGCCGC CGGGTTCGCG TGACATCCCT GACAATGAGT TCCGGGTGGT GTTGGCCCGG      2520

CGAGGCCAGC ACTGGGTGTC GGCGGTACGG GTTGGCAATG ACATCACCGT CGATGACGTG      2580

ACGGTCTCGG ATAGCGCCTC GATCGCCGCA CTGGTAATGG ACGGTCTGGA GTCGATTCAC      2640

CACGCCGACC CAGCCGCGAT CAACGCGGTC AACGTGCCAA TGGAGGAGAT CTCGTGCCGA      2700

ATTCGGCACG AGGCACGAGG CGGTGTCGGT GACGACGGGA TCGATCACGA TCATCGACCG      2760

GCCGGGATCC TTGGCGATCT CGTTGAGCAC GACCCGGGCC CGCGGGAAGC TCTGCGACAT      2820

CCATGGGTTC TTCCCG                                                     2836
```

(2) INFORMATION FOR SEQ ID NO:5:

(i) SEQUENCE CHARACTERISTICS:
        (A) LENGTH: 900 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Mycobacterium tuberculosis (xi) SEQUENCE DESCRIPTION: SEQ ID NO:5:

```
AACATGCTGC ACGGGGTGCG TGACGGGCTG GTTCGCGACG CCAACAACTA CGAGCAGCAA       60

GAGCAGGCCT CCCAGCAGAT CCTCAGCAGC TAACGTCAGC CGCTGCAGCA CAATACTTTT      120

ACAAGCGAAG GAGAACAGGT TCGATGACCA TCAACTATCA GTTCGGTGAT GTCGACGCTC      180

ACGGCGCCAT GATCCGCGCT CAGGCCGGGT TGCTGGAGGC CGAACATCAG GCCATCATTC      240

GTGATGTGTT GACCGCGAGT GACTTTTGGG GCGGCGCCGG TTCGGCGGCC TGCCAGGGGT      300

TCATTACCCA ATTGGGCCGT AACTTCCAGG TGATCTACGA ACAGGCCAAC GCCCACGGGC      360

AGAAGGTGCA GGCTGCCGGC AACAACATGG CGCAAACCGA CAGCGCCGTC GGCTCCAGCT      420

GGGCCTGACA CCAGGCCAAG GCCAGGGACG TGGTGTACGA GTGAAGGTTC CTCGCGTGAT      480

CCTTCGGGTG GCAGTCTAGG TGGTCAGTGC TGGGGTGTTG GTGGTTTGCT GCTTGGCGGG      540

TTCTTCGGTG CTGGTCAGTG CTGCTCGGGC TCGGGTGAGG ACCTCGAGGC CCAGGTAGCG      600

CCGTCCTTCG ATCCATTCGT CGTGTTGTTC GGCGAGGACG GCTCCGACGA GGCGGATGAT      660

CGAGGCGCGG TCGGGAAGA TGCCCACGAC GTCGGTTCGG CGTCGTACCT CTCGGTTGAG       720

GCGTTCCTGG GGGTTGTTGG ACCAGATTTG GCGCCAGATC TTCTTGGGGA AGGCGGTGAA      780

CGCCAGCAGG TCGGTGCGGG CGGTGTCGAN GTGCTCGGCC ACCGCGGGGA GTTTGTCGGT      840

CAGAGCGTCG AGTACCCGAT CATATTGGGC AACAACTGAT TCGGCGTTGG GCTGGTCGTA      900
```

(2) INFORMATION FOR SEQ ID NO:6:

(i) SEQUENCE CHARACTERISTICS:
        (A) LENGTH: 1905 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Mycobacterium tuberculosis (xi) SEQUENCE DESCRIPTION: SEQ ID NO:6:

```
GCTCGCCGGA TGTGGGCGTC CGCGCAAAAC ATTTCCGGTG CGGGCTGGAG TGGCATGGCC    60

GAGGCGACCT CGCTAGACAC CATGGCCCAG ATGAATCAGG CGTTTCGCAA CATCGTGAAC   120

ATGCTGCACG GGGTGCGTGA CGGGCTGGTT CGCGACGCCA ACAACTACGA GCAGCAAGAG   180

CAGGCCTCCC AGCAGATCCT CAGCAGCTAA CGTCAGCCGC TGCAGCACAA TACTTTTACA   240

AGCGAAGGAG AACAGGTTCG ATGACCATCA ACTATCAGTT CGGTGATGTC GACGCTCACG   300

GCGCCATGAT CCGCGCTCAG GCCGGGTTGC TGGAGGCCGA GCATCAGGCC ATCATTCGTG   360

ATGTGTTGAC CGCGAGTGAC TTTTGGGGCG CGCCGGTTC GGCGGCCTGC CAGGGGTTCA    420

TTACCCAGTT GGGCCGTAAC TTCCAGGTGA TCTACGAACA AGCCAACACC CACGGGCAGA   480

AGGTGCAAGC TGCCGGCAAC AACATGGCGC AAACCGACAG CGCCGTCNGC TCCAGCTGGG   540

CCTGACACCA GGCCAAGGCC AGGGACGTGG TGTACNAGTG AAGGTTCCTC GCGTGATCCT   600

TCGGGTGGCA GTCTAGGTGG TCAGTGCTGG GGTGTTGGTG GTTTGCTGCT TGGCGGGTTC   660

TTCGGTGCTG GTCAGTGCTG CTCGGGCTCG GGTGAGGACC TCGAGGCCCA GGTAGCGCCG   720

TCCTTCGATC CATTCGTCGT GTTGTTCGGC GAGGACNGCT CCGACGANGC GGATGATCGA   780

GGCGCGGTCG GGGAAGATGC CCACGACGTC GGTTCGGCGT CGTACCTCTC GGTTGAAGCG   840

TTCCTGGGGG CCACCGCTTG GCGCCNANGC ACTCCACGCC AATTCGTCNC ACCTAACAGC   900

GGTGGCCAAC GACTATGACT ACGACACCGT TTTTGCCAGG GCCCTCNAAA GGATCTGCGC   960

GTCCCGGCGA CACGCTTTTT GCGATAAGTA CCTCCGGCAA TTCTATGAGT GTACTGCGGN  1020

CCGCGAAAAC CGCAAGGGAG TTGGGTGTGA CGGTTNTTGC AAATGACGGG CGAATCCGGC  1080

GGCCAGCTGG CAGAATTCGC AGATTTCTTG ATCAACGTCC CGTCACGCGA CACCGGGCGA  1140

ATCCAGGAAT CTCACATCGT TTTTATTCAT GCGATCTCCG AACATGTCGA ACACGCGCTT  1200

TTCGCGCCTC GCCAATAGGA AAGCCGATCC TTACGCGGCC ATTCGAAAGA TGGTCGCGGA  1260

ACGTGCGGGA CACCAATGGT GTCTCTTCCT CGATAGAGAC GGGGTCATCA ATCGACAAGT  1320

GGTCGGCGAC TACGTACGGA ACTGGCGGCA GTTTGAATGG TTGCCCGGGG CGGCGCGGGC  1380

GTTGAAGAAG CTACGGGCAT GGGCTCCGTA CATCGTTGTC GTGACAAACC AGCAGGGCGT  1440

GGGTGCCGGA TTGATGAGCG CCGTCGACGT GATGGTGATA CATCGGCACC TCCAAATGCA  1500

GCTTGCATCC GATGGCGTGC TGATAGATGG ATTTCAGGTT TGCCCGCACC ACCGTTCGCA  1560

GCGGTGTGGC TGCCGTAAGC CGAGACCGGG TCTGGTCCTC GACTGGCTCG ACGACACCC   1620

CGACAGTGAG CCATTGCTGA GCATCGTGGT TGGGACAGC CTCAGCGATC TTGACATTGG    1680

CACACAACGT CGCCGCTGCT GCCGGTGCAT GTGCCAGTGT CCAGATAGGG GGCGCCAGTT  1740

CTGGCGGTGT CGCTGACGCG TCATTTGACT CGCTCTGGGA GTTCGCTGTC GCAGTCGGAC  1800

ATGCGCGGGG GGAGCGGGGC TAATGGCGAT CTTGCGCGGG CGAGCGCCGT NGCGGNTCGG  1860
```

```
ACTNNGCGGT GGCGGGACAG ACGTGGAACC GTACTCGAGC CAGTT              1905
```

(2) INFORMATION FOR SEQ ID NO:7:

(i) SEQUENCE CHARACTERISTICS:
        (A) LENGTH: 2921 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Mycobacterium tuberculosis (xi) SEQUENCE DESCRIPTION: SEQ ID NO:7:

```
CGGGATGCCG TGGTGGTTGG TATTGCCCAA ACCCTGGCGC TGGTCCCCGG GGTATCCAGG    60
TCCGGGTCGA CCATCAGCGC TGGACTGTTT CTCGGACTCG ACCGTGAACT GGCCGCCCGA   120
TTCGGATTCC TGCTGGCCAT TCCAGCGGTG TTCGCCTCCG GGTTGTTCTC GTTGCCCGAC   180
GCATTCCACC CGGTAACCGA GGGCATGAGC GCTACTGGCC CGCAGTTGCT GGTGGCCACC   240
CTGATCGCGT TCGTCCTCGG TCTGACCGCG GTGGCCTGGC TGCTGCGGTT TCTGGTGCGA   300
CACAACATGT ACTGGTTCGT CGGCTACCGG GTGCTCGTCG GGACGGGCAT GCTCGTGCTG   360
CTGGCTACCG GGACGGTAGC CGCGACATGA CCGTCATCTT GCTACGCCAT GCCCGTTCCA   420
CCTCGAACAC CGCGGGCGTG CTGGCCGGCC GGTCCGGCGT CGACCTCGAC GAGAAGGGGC   480
GCGAGCAGGC CACCGGGTTG ATCGATCGAA TTGGTGACCT GCCGATCCGG GCGGTCGCGT   540
CTTCTCCAAT GCTGCGGTGT CAACGCACCG TCGAACCGCT GGCCGAGGCG CTGTGCCTGG   600
AGCCGCTCAT CGATGACCGG TTCTCCGAAG TCGACTACGG CGAATGGACT GGCAGAAAAA   660
TCGGTGACCT GGTCGACGAG CCGTTGTGGC GGGTAGTCCA GGCCCACCCC AGCGCGGCGG   720
TGTTTCCCGG CGGTGAGGGT TTGGCGCAGG TGCAGACGTG GTTGTCCTGA CGGATTTCCA   780
TGCCGGGGAA CACCAAGACC GGATCGGCAC TGGCGGTCGC CGGCGAAAAC CCGGCCGCCA   840
ATAGGGCGAC CGTCGCTGCG AATGCGCGTG GTACCAGGCG GACCACCTTG AACTCCCATC   900
CGTCGGGGCC AAGCGCATCG CCCGCCGCCG GTTACGGCTA AGGCGTACCA AAACCCGACG   960
GTAATACTTC GGCAATGTCG GGTCNCGACG TTACCGAGAC GTGACCAGNG AGGCNGCGGC  1020
ATTGGATTTA TCGATGGTGC GCGGTTCCCA NCCCGGCGGT CCGAANACGT AGCCCAGCCG  1080
ATCCCGCAGA CGTGTTGCCG ACCGCCAGTC ACGCACGATC GCCACGTACT CGCGGGTCTG  1140
CAGCTTCCAG ATGTTGAACG TGTCGACCCG CTTGGTCAGG CCATAATGCG GTCGGAATAG  1200
CTCCGGCTGA AAGCTACCGA ACAGGCGGTC CCAGATGATG AGGATGCCGC CATAGTTCTT  1260
GTCCANATAC ACCGGGTCCA TTCCGTGGTG GACCCGGTGG TGCGACGGGG TATTGAAGAC  1320
GAATTCGAAC CACCGCGGCA GCCTGTCGAT CCGCTCGGTG TGCACCCAGA ACTGGTAGAT  1380
CAAGTTCAGC GACCAATTGC AGAACACCAT CCAAGGGGGA AGCCCCATCA GTGGCAGCGG  1440
AACCCACATG AGAATCTCGC CGCTGTTGTT CCANTTTCTG GCGCAGCGCG GTGGCGAAGT  1500
TGAAGTATTC GCTGGAGTGA TGCGCCTGGT GGGTAGCCCA GATCAGCCGA ACTCGGTGGG  1560
CGATGCGGTG ATAGGAGTAG TACAGCAGAT CGACACCAAC GATCGCGATC ACCCAGGTGT  1620
ACCACCGGTG GGCGGACAGC TGCCAGGGGG CAAGGTAGGC ATAGATTGCG GCATAACCGA  1680
GCAGGGCAAG GGACTTCCAG CCGGCGGTGG TGGCTATCGA AACCAGCCCC ATCGAGATGC  1740
TGGCCACCGA GTCGCGGGTG AGGTAAGCGC CCGAGGCGGG CCGTGGCTGC CCGGTAGCAG  1800
CGGTCTCGAT GCTTTCCAGC TTGCGGGCCG CCGTCCATTC GAGAATCAGC AGCAATAGAA  1860
```

```
AACATGGAAT GGCGAACAGT ACCGGGTCCC GCATTTCCTC GGGCAGCGCT GAGAAGAATC    1920

CGGCGACGGC ATGGCCGAGG CGACCTCGNT AGACACCATG ACCCAGATGA ATCAGGCGTT    1980

TCGCAACATC GTGAACATGC TGCACGGGGT GCGTGACGGG CTGGTTCGCG ACGCCAACAA    2040

NTACGAACAG CAAGAGCAGG CCTCCCAGCA GATCCTCAGC AGCTGACCCG GCCCGACGAC    2100

TCAGGAGGAC ACATGACCAT CAACTATCAA TTCGGGGACG TCGACGCTCA CGGCGCCATG    2160

ATCCGCGCTC AGGCCGGGTC GCTGGAGGCC GAGCATCAGG CCATCATTTC TGATGTGTTG    2220

ACCGCGAGTG ACTTTTGGGG CGGCGCCGGT TCGGCGGCCT GCCAGGGGTT CATTACCCAG    2280

CTGGGCCGTA ACTTCCAGGT GATNTACGAG CAGGCCAACG CCCACGGGCA GAAGGTGCAG    2340

GCTGCCGGCA ACAACATGGC ACAAACCGAC AGCGCCGTCG GCTCCAGCTG GGCATAAAGN    2400

TGGCTTAAGG CCCGCGCCGT CAATTACAAC GTGGCCGCAC ACCGGTTGGT GTGTGGCCAC    2460

GTTGTTATCT GAACGACTAA CTACTTCGAC CTGCTAAAGT CGGCGCGTTG ATCCCCGGTC    2520

GGATGGTGCT GAACTGGGAA GATGGCCTCA ATGCCCTTGT TGCGGAAGGG ATTGAGGCCA    2580

TCGTGTTTCG TACTTTAGGC GATCAGTGCT GGTTGTGGGA GTCGCTGCTG CCCGACGAGG    2640

TGCGCCGACT GCCCGAGGAA CTGGCCCGGG TGGACGCATT GTTGGACGAT CCGGCGTTCT    2700

TCGCCCCGTT CGTGCCGTTC TTCGACCCGC GCAGGGGCCG GCCGTCGACG CCGATGGAGG    2760

TCTATCTGCA GTTGATGTTT GTGAAGTTCC GCTACCGGCT GGGCTATGAG TCGCTGTGCC    2820

GGGAGGTGGC TGATTCGATC ACCTGACGGC GGTTTTGCCG CATTGCGCTG GACGGGTCGG    2880

TGCCGCATCC GACCACATTG ATGAAGCTCA CCACGCGTTG C                         2921

(2) INFORMATION FOR SEQ ID NO:8:

(i) SEQUENCE CHARACTERISTICS:
          (A) LENGTH: 1704 base pairs
          (B) TYPE: nucleic acid
          (C) STRANDEDNESS: double
          (D) TOPOLOGY: linear (ii) MOLECULE TYPE: DNA (genomic)

(vi) ORIGINAL SOURCE:
          (A) ORGANISM: Mycobacterium tuberculosis (xi) SEQUENCE DESCRIPTION: SEQ ID NO:8:

CGCGATCGTC GTCAACGANG TCGACCGTCA CCACGGACTG ATCAACAAGT TCGCAGGCGA      60

CGCCGCCCTG GCCATCTTCG GAGCCCCGAA CCGCCTCGAC CGTCCCGAAG ACGCCGCGCT     120

GGCCGCCGCC CGGGCCATAN CCGANCGGCT GGCCNACGAG ATGCCCGAGG TCCAAGCCGG     180

CATCGGGGTG GCGGCAGGCC ANATCGTCGC CGGCAATGTC GGCGCCAAGC AAAGATTCNA     240

ATACACAGTG GTCGGCAAGC CGGTCAACCA NGCGGCCCGA TTGTGCGAAC TGGCCAAATC     300

ACACCCCGCG CGATTGGGTC TCGCCCGCTC GGCTCATGGT CACCCAATTC AAGGACTACT     360

TTGGCCTGGC GCACGACCTG CCGAAGTGGG CGAGTGAAGG CGCCAAAGCC GCCGGTGAGG     420

CCGCCAAGGC GTTGCCGGCC GCCGTTCCGG CCATTCCGAG TGCTGGCCTG AGCGGCGTTG     480

CGGGCGCCGT CGGTCAGGCG GCGTCGGTCG GGGGATTGAA GGTTCCGGCC GTTTGGACCG     540

CCACGACCCC GGCGGCGAGC CCCGCGGTGC TGGCGGCGTC CAACGGCCTC GGAGCCGCGG     600

CCGCCGCTGA AGGTTCGACA CACGCGTTTG GCGGGATGCC GCTCATGGGT ANCGGTGCCG     660

GACGTGCGTT TAACAACTTC GCTGCCCCTC GATACGGATT CAAGCCGACC GTGATCGCCC     720

AACCGCCGGC TGGCGGATGA CCAACTACGT TCGTTGATCG AGGATCGAAT TCNACGATTC     780
```

-continued

```
AAAGGGAGGA ATTCATATGA CCTCNCGTTT TATGACGGAT CCGCACGCNA TNCGGGACAT      840

GGCGGGCCGT TTTGAGGTGC ACGCCCAGAC GGTGGAGGAC GAGGCTNGCN GGATGTGGGC      900

GTCCGCGCAA AACATTTCCG GTGCGGGCTG GAGTGGCATG GCCGAGGCGA CCTCGNTAGA      960

CACCATGGCC CAGATGAATC AGGCGTTTCN CAACATCGTG AACATGCTGC ACGGGGTGNG     1020

TGACGGGCTG GTTCGCGACG CCAACAACTA CGAACAGCAA GAGCAGGCCT CCCAGCAGAT     1080

CCTCAGCAGC TGACCCGGCC CGACGACTCA GGAGGACACA TGACCATCAA CTATCAATTC     1140

GGGGACGTCG ACGCTCATGG CGCCATGATC CGCGCTNTGG CCGGGTTGCT GGAGGCCGAG     1200

CATCAGGCCA TCATTTCTGA TGTGTTGACC GCGAGTGACT TTTGGGGCGG CGCCGGTTCG     1260

GCGGCCTGCC AGGGGTTCAT TACCCAGTTG GGCCGTAACT TCCAGGTGAT TTACGAGCAG     1320

GCCAACGCCC ACGGGCAGAA GGTGCAGGCT GCCGGCAACA ACATGGCACA AACCGACAGC     1380

GCCGTNGGNT CCAGCTGGGC CTAACCCGGG TCNTAAGTTG GGTCCGCGCA GGGCGGGCCG     1440

ATCAGCGTNG ACTTTGGCGC CCGATACACG GGCATNTTNT NGTCGGGAAC ACTGCGCCCG     1500

CGTCAGNTGC CCGCTTCCCC TTGTTNGGCG ACGTGCTCGG TGATGGCTTT GACGACCGCT     1560

TCGCCGGCGC GGCCAATCAA TTGGTCGCGC TTGCCTNTAG CCCATTCGTG CGACGCCCGC     1620

GGCGCCGCGA GTTGTCCCTT GAAATAAGGA ATCACAGCAC GGGCGAACAG CTCATAGGAG     1680

TGAAAGGTTG CCGTGGCGGG GCCC                                           1704
```

(2) INFORMATION FOR SEQ ID NO:9:

(i) SEQUENCE CHARACTERISTICS:
        (A) LENGTH: 2286 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Mycobacterium tuberculosis (xi) SEQUENCE DESCRIPTION: SEQ ID NO:9:

```
CCGTCTTGGC GTCTGGGCGC ATTGTGATCT GGGCCANTTG CCCCTCCACC CAGACCGCGC       60

CCAGCTTGTC GATCCAGCCC GCGACCCGGA TTGCCACCGC GCGAACCGGG AACGGATTCT      120

CCGCTGAATT CTGGGTCACT TCGCAGTCGC GCGGGTGATC CTGTTGGCGA NCAGCGTCTG      180

GAACGGGCGT CNAACGCGTG CCGTAAGCCC AGCGTGTACG CCGTCAGCCC GACGCCGATG      240

CCGAATGCCT TGCCGCCCAA GCTGAGCCGC GCGGGCTCCA CCAAGAGCGT CACGGTGAGC      300

CAGCCAACCA GATGCAAGGC GACGATCACC GCGAAGTGCC GAATTCGGCA CGAGAGGTGC      360

TGGAAATCCA GCAATACGCC CGCGAGCCGA TCTCGTTGGA CCAGACCATC GGCGACGANG      420

GCGACAGNCA GCTTGGCGAT TTCATCGAAA ACAGCGAGGC GGTGGTGGNC GTCGACGCGG      480

TGTCCTTCAC TTTGCTGCAT GATCAACTGC ANTCGGTGCT GGACACGCTC TCCGAGCGTG      540

AGGCGGGCGT GGTGCGGCTA CGCTTCGGCC TTACCGACGG CCAGCCGCGC ACCCTTGACG      600

AGATCGGCCA GGTCTACGGC GTGACCCGGG AACGCATCCG CCAGATCGAA TCCAAGACTA      660

TGTCGAAGTT GCGCCATCCG AGCCGCTCAC AGGTCCTGCG CGACTATCGT GCCGAATTCG      720

GCACGAGCCG TTTTGAGGTG CACGCCCAGA CGGTGGAGGA CGAGGCTCGC GGATGTGGG      780

CGTCCGCGCA AAACATTTCC GGTGCGGGCT GGAGTGGCAT GGCCGANGCG ACCTCGCTAG      840

ACACCATGGC CCAGATGAAT CAGGCGTTTC GCAACATCGT GAACATGCTG CACGGGGTGC      900

GTGACGGGCT GGTTCGCGAC GCCAACAACT ACGAACAGCA AGAGCAGGCC TCCCAGCAGA      960
```

-continued

| | |
|---|---|
| TCCTCAGCAG CTGACCCGGC CCGACGACTC AGGAGGACAC ATGACCATCA ACTATCAATT | 1020 |
| CGGGGACGTC GACGCTCATG GCGCCATGAT CCGCGCTCTG GCCGGGTTGC TGGAGGCCGA | 1080 |
| GCATCAGGCC ATCATTTCTG ATGTGTTGAC CGCGAGTGAC TTTTGGGGCG GCGCCGGTTC | 1140 |
| GGCGGCCTGC CAGGGGTTCA TTACCCAGTT GGGCCGTAAC TTCCAGGTGA TCTACGAGCA | 1200 |
| GGCCAACGCC CACGGGCAGA AGGTGCAGGC TGCCGGCAAC AACATGGCAC AAACCGACAG | 1260 |
| CGCCGTCGGC TCCAGCTGGG CCTAACCCGG GTCCTAAGTT GGGTCCGCGC AGGGCGGGCC | 1320 |
| GATCAGCGTC GACTTTGGCG CCCGATACAC GGGCATGTNG TNGTCGGGAA CACTGCGCCC | 1380 |
| GCGTCAGCTG CCCGCTTCCC CTTGTTCGGC GACGTGCTCG GTGATGGCTT TGACGACCGC | 1440 |
| TTCGCCGGCG CGGCCAATCA ATTGGTCGCG CTTGCCTCTA GCCTCGTGCC GAATTCGGCA | 1500 |
| CGAGGGTGCT GGTGCCGCGC TATCGGCAGC ACGTGAGCTC CACGACGAAC TCATCCCAGT | 1560 |
| GCTGGGTTCC GCGGAGTTCG GCATCGGCGT GTCGGCCGGA AGGGCCATCG CCGGCCACAT | 1620 |
| CGGCGCTCAA GCCCGCTTCG AGTACACCGT CATCGGCGAC CCGGTCAACG AGGCCGCCCG | 1680 |
| GCTCACCGAA CTGGCCAAAG TCGAGGATGG CCACGTTCTG GCGTCGGCGA TCGCGGTCAG | 1740 |
| TGGCGCCCTG GACGCCGAAG CATTGTGTTG GGATGTTGGC GAGGTGGTTG AGCTCCGCGG | 1800 |
| ACGTGCTGCA CCCACCCAAC TAGCCAGGCC AATGAATNTG GCNGCACCCG AAGAGGTTTC | 1860 |
| CAGCGAAGTA CGCGGCTAGT CGCGCTTGGC TGCNTTCTTC GCCGGCACCT TCCGGGCAGC | 1920 |
| TTTCCTGGCT GGCCGTTTTG CCGGACCCCG GGCTCGGCGA TCGGCCAACA GCTCGGCGGC | 1980 |
| GCGCTCGTCG GTTATGGAAG CCACGTNGTC GCCCTTACGC AGGCTGGCAT TGGTCTCACC | 2040 |
| GTCGGTGACG TACGGCCCGA ATCGGCCGTC CTTGATGACC ATTGGCTTGC CAGACGCCGG | 2100 |
| ATNTGNTCCC AGCTCGCGCA GCGGCGGAGC CGAAGCGCTT TGCCGGCCAC GACNTTTCGG | 2160 |
| CTCTGNGTAG ATNTTCAGGG CTTCGTCGAG CGNGATGGTG AATATATGGT CTTCGGTGAC | 2220 |
| CAGTGATCGA GAATCGTTGC CGCGCTTTAG ATACGGTCNG TAGCGCCCGT TCTGCGCGGT | 2280 |
| GATNTC | 2286 |

(2) INFORMATION FOR SEQ ID NO:10:

(i) SEQUENCE CHARACTERISTICS:
        (A) LENGTH: 1136 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Mycobacterium tuberculosis (xi) SEQUENCE DESCRIPTION: SEQ ID NO:10:

| | |
|---|---|
| GGGCATCTTC CCCGACCGCG CCTCGATCAT CCGCCTCGTC GGAGCCGTCC TCGCCGAACA | 60 |
| ACACGACGAA TGGATCGAAG GACGGCGCTA CCTGGGCCTC GAGGTCCTCA CCCGAGCCCG | 120 |
| AGCAGCACTG ACCAGCACCG AAGAACCGCC AAGCAGCAAA CCACCAACAC CCCAGCACTG | 180 |
| ACCACCTAGA CTGCCACCCG AAGGATCACG CGAGGAACCT TCACTCGTAC ACCACGTCCC | 240 |
| TGGCCTTGGC CTGGTGTCAG GCCCAGCTGG AGCCGACGGC GCTGTCGGTT TGCGCCATGT | 300 |
| TGTTGCCGGC AGCCTGCACC TTCTGCCCGT GGGCGTTGGC CTGCTCGTAG ATCACCTGGA | 360 |
| AGTTACGGCC CAACTGGGTA ATGAACCCCT GGCAGGCCGC CGAACCGGCG CCGCCCCAAA | 420 |
| AGTCACTCGC GGTCAACACA TCACGAATGA TGGCCTGATG CTCGGCCTCC AGCAACCCGG | 480 |

```
CCTGAGCGCG GATCATGGCG CCGTGAGCGT CGACATCACC GAACTGATAG TTGATGGTCA      540

TCGAACCTGT TCTCCTTCGC TTGTAAAAGT ATTGTGCTGC AGCGGCTGAC GTTAGCTGCT      600

GAGGATCTGC TGGGAGGCCT GCTCTTGCCT CGTGCCGAAT TCGGCACGAG AGGCCGCCTT      660

CGAAGAAATC CTTTGAGAAT TCGCCAAGGC CGTCGACCCA GCATGGGGTC AGCTCGCCAG      720

CCGCGCCGGC TGGCAACCGT TCCCGCTCGA GAAAGACCTG GAGGAATACC AGTGACAAAC      780

GACCTCCCAG ACGTCCGAGA GCGTGACGGC GGTCCACGTC CCGCTCCTCC TGCTGGCGGG      840

CCACGCTTGT CAGACGTGTG GGTTTACAAC GGGCGGGCGT ACGACCTGAG TGAGTGGATT      900

TCCAAGCATC CCGGCGGCGC CTTNTTCATT GGGCGGACCA AGAACCGCGA CATCACCGCA      960

ATCGTCAAGT CCTACCATCG TGATCCGGCG ATTGTCGAGC GAATCCTGCA GCGGAGGTAC     1020

GCGTTGGGCC GCGACGCAAC CCCTAGGGAC ATCCACCCCA AGCACAATGC ACCGGCATTT     1080

CTGTTCAAAG ACGACTTCAA CAGCTGGCGG GACACCCCGA AGTATCGATT NGACGA         1136

(2) INFORMATION FOR SEQ ID NO:11:

(i) SEQUENCE CHARACTERISTICS:
          (A) LENGTH: 967 base pairs
          (B) TYPE: nucleic acid
          (C) STRANDEDNESS: double
          (D) TOPOLOGY: linear (ii) MOLECULE TYPE: DNA (genomic)

(vi) ORIGINAL SOURCE:
          (A) ORGANISM: Mycobacterium tuberculosis (xi) SEQUENCE DESCRIPTION: SEQ ID NO:11:

TGAGCGCCAA CCCTACCGTC GGTTCGTCAC ACGGACCGCA TGGCCTGCTC CGCGGACTGC       60

CGCTAGGGTC GCGGATCACT CGGCGTAGCG GCGCCTTTGC CCACCGATAT GGGTTCCGTC      120

ACAGTGTGGT TGCCCGCCCG CCATCGGCCG GATAACGCCA TGACCTCAGC TCGGCAGAAA      180

TGACAATGCT CCCAAAGGCG TGAGCACCCG AAGACAACTA AGCAGGAGAT CGCATGCCGT      240

TTGTGACTAC CCAACCAGAA GCACTGGCGG CGGCGGCCGG CAGTCTGCAG GGAATCGGCT      300

CCGCATTGAA CGCCCAGAAT GCGGCTGCGG CGACTCCCAC GACGGGGTG GTCCGGCGGC       360

CGCCGATGAA NTGTCGGCGC TGACGGCGGC TCAGTTCGCG GCACACGCCC AGATCTATCA      420

GGCCGTCAGC GCCCAGGCCG CGGCGATTCA CGAGATGTTC GTCAACACTC TACAGATGAG      480

CTCAGGGTCG TATGCTGCTA CCGAGGCCGC CAACGCGGCC GCGGCCGGNT AGAGGAGTCA      540

CTGCGATGGA TTTTGGGGCG TTGCCGCCGG AGGTCAATTC GGTGCGGATG TATGCCGTTC      600

CTGGCTCGGC ACCAATGGTC GCTGCGGCGT CGGCCTGGAA CGGGTTGGCC GCGGAGCTGA      660

GTTCGGCGGC CACCGGTTAT GAGACGGTGA TCACTCAGCT CAGCAGTGAG GGGTGGCTAG      720

GTCCGGCGTC AGCGGCGATG GCCGAGGCAG TTGCGCCGTA TGTGGCGTGG ATGAGTGCCG      780

CTGCGGCGCA AGCCGAGCAG GCGGCCACAC AGGCCAGGGC CGCCGCGGCC GCTTTTGAGG      840

CGGCGTTTGC CGCGACGGTG CCTCCGCCGT TGATCGCGGC CAACCGGGCT TCGTTGATGC      900

AGCTGATCTC GACGAATGTC TTTGGTCAGA ACACCTCGGC GATCGCGGCC GCCGAAGCTC      960

AGTACGG                                                                967

(2) INFORMATION FOR SEQ ID NO:12:

(i) SEQUENCE CHARACTERISTICS:
          (A) LENGTH: 585 base pairs
          (B) TYPE: nucleic acid
          (C) STRANDEDNESS: double
```

(D) TOPOLOGY: linear (ii) MOLECULE TYPE: DNA (genomic)

(vi) ORIGINAL SOURCE:
         (A) ORGANISM: Mycobacterium tuberculosis (xi) SEQUENCE DESCRIPTION: SEQ ID NO:12:

TGGATTCCGA TAGCGGTTTC GGCCCCTCGA CGGGCGACCA CGGCGCGCAG GCCTCCGAAC      60

GGGGGGCCGG GACGCTGGGA TTCGCCGGGA CCGCAACCAA AGAACGCCGG GTCCGGGCGG     120

TCGGGCTGAC CGCACTGGCC GGTGATGAGT TCGGCAACGG CCCCCGGATG CCGATGGTGC     180

CGGGGACCTG GGAGCAGGGC AGCAACGAGC CCGAGGCGCC CGACGGATCG GGGAGAGGGG     240

GAGGCGACGG CTTACCGCAC GACAGCAAGT AACCGAATTC CGAATCACGT GGACCCGTAC     300

GGGTCGAAAG GAGAGATGTT ATGAGCCTTT TGGATGCTCA TATCCCACAG TTGGTGGCCT     360

CCCAGTCGGC GTTTGCCGCC AAGGCGGGGC TGATGCGGCA CACGATCGGT CAGGCCGAGC     420

AGGCGGCGAT GTCGGCTCAG GCGTTTCACC AGGGGGAGTC GTCGGCGGCG TTTCAGGCCG     480

CCCATGCCCG GTTTGTGGCG GCGGCCGCCA AAGTCAACAC CTTGTTGGAT GTCGCGCAGG     540

CGAATCTGGG TGAGGCCGCC GGTACCTATG TGGCCGCCGA TGCTG                     585

(2) INFORMATION FOR SEQ ID NO:13:

(i) SEQUENCE CHARACTERISTICS:
         (A) LENGTH: 144 amino acids
         (B) TYPE: amino acid
         (C) STRANDEDNESS: single
         (D) TOPOLOGY: linear (ii) MOLECULE TYPE: peptide (vi) ORIGINAL SOURCE:
         (A) ORGANISM: Mycobacterium tuberculosis (xi) SEQUENCE DESCRIPTION: SEQ ID NO:13:

Ala Leu Val Thr Thr Asn Phe Phe Gly Val Asn Thr Ile Pro Ile Ala
1               5                   10                  15

Leu Asn Glu Ala Asp Tyr Leu Arg Met Trp Ile Gln Ala Ala Thr Val
            20                  25                  30

Met Ser His Tyr Gln Ala Val Ala His Glu Ile Trp Cys Leu His Glu
        35                  40                  45

Xaa Ala Ser Ser Gly Lys Pro Trp Ala Ser Ile Thr Thr Gly Ala Pro
    50                  55                  60

Gly Ser Pro Ala Ser Thr Thr Arg Ser Arg Thr Pro Leu Val Ser Thr
65                  70                  75                  80

Asn Arg Xaa Val Xaa Ala Pro Ile Val Ser Pro Asn His Thr Gly His
                85                  90                  95

Arg Pro Glu Lys Gly Leu Gly Ser Xaa Gln Arg Arg Leu Ser Arg Val
            100                 105                 110

Leu Pro Arg Ile Ile Asp Arg Pro Ala Gly Pro Xaa Gly Pro Pro Leu
        115                 120                 125

Thr Ser Gly Ser His Phe Leu Cys Ser Trp His Gly Tyr Ser Ser Gln
    130                 135                 140

(2) INFORMATION FOR SEQ ID NO:14:

(i) SEQUENCE CHARACTERISTICS:
         (A) LENGTH: 352 amino acids
         (B) TYPE: amino acid
         (C) STRANDEDNESS: single (D) TOPOLOGY: linear (ii) MOLECULE TYPE: peptide (vi) ORIGINAL SOURCE:
         (A) ORGANISM: Mycobacterium tuberculosis (xi) SEQUENCE DESCRIPTION: SEQ ID NO:14:

His Ala Leu Ala Ala Gln Tyr Thr Glu Ile Ala Thr Glu Leu Ala Ser
1               5                   10                  15

Val Leu Ala Ala Val Gln Ala Ser Ser Trp Gln Gly Pro Ser Ala Asp
            20                  25                  30

Arg Phe Val Val Ala His Gln Pro Phe Arg Tyr Trp Leu Thr His Ala
        35                  40                  45

Ala Thr Val Ala Thr Ala Ala Ala Ala His Xaa Thr Ala Ala Ala
    50                  55                  60

Gly Tyr Thr Ser Ala Leu Gly Gly Met Pro Thr Leu Ala Glu Leu Ala
65                  70                  75                  80

Ala Asn His Ala Met His Gly Ala Leu Val Thr Thr Asn Phe Phe Gly
                85                  90                  95

Val Asn Thr Ile Pro Ile Ala Leu Asn Glu Ala Asp Tyr Leu Arg Met
                100                 105                 110

Trp Ile Gln Ala Ala Thr Val Met Ser His Tyr Gln Ala Val Ala His
            115                 120                 125

Glu Ser Val Ala Ala Thr Pro Ser Thr Pro Pro Ala Pro Gln Ile Val
130                 135                 140

Thr Ser Ala Ala Ser Ser Ala Ala Ser Ser Phe Pro Asp Pro Thr
145                 150                 155                 160

Lys Leu Ile Leu Gln Leu Leu Lys Asp Phe Leu Glu Leu Leu Arg Tyr
                165                 170                 175

Leu Ala Val Glu Leu Leu Pro Gly Pro Leu Gly Asp Leu Ile Ala Gln
                180                 185                 190

Val Leu Asp Trp Phe Ile Ser Phe Val Ser Gly Pro Val Phe Thr Phe
            195                 200                 205

Leu Ala Tyr Leu Val Leu Asp Pro Leu Ile Tyr Phe Gly Pro Phe Ala
    210                 215                 220

Pro Leu Thr Ser Pro Val Leu Leu Pro Ala Val Glu Leu Arg Asn Arg
225                 230                 235                 240

Leu Lys Thr Ala Thr Gly Leu Thr Leu Pro Pro Thr Val Ile Phe Asp
                245                 250                 255

His Pro Thr Pro Thr Ala Val Ala Glu Tyr Val Ala Gln Gln Met Ser
                260                 265                 270

Gly Ser Arg Pro Thr Glu Ser Gly Asp Pro Thr Ser Gln Val Val Glu
            275                 280                 285

Pro Ala Arg Ala Glu Phe Gly Thr Ser Ala Val His Gln Ile Pro Pro
    290                 295                 300

Arg Pro Ala Asp Thr Arg Arg Ala Cys Arg His Arg Asp Asp Val Pro
305                 310                 315                 320

Arg Asp Ser Arg Ile Ala Gln His Arg Asp Gly Ala Gly Leu Asp Pro
                325                 330                 335

Thr Glu Arg Gly Thr Ser Glu Gly Asp Gln Gly Leu Val Ser Gly Trp
            340                 345                 350

(2) INFORMATION FOR SEQ ID NO:15:

(i) SEQUENCE CHARACTERISTICS:

(A) LENGTH: 141 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:15:

Met Asp Phe Gly Ala Leu Pro Pro Glu Val Asn Ser Val Arg Met Tyr
1               5                   10                  15

Ala Val Pro Gly Ser Ala Pro Met Val Ala Ala Ser Ala Trp Asn
            20                  25                  30

Gly Leu Ala Ala Glu Leu Ser Ser Ala Ala Thr Gly Tyr Glu Thr Val
        35                  40                  45

Ile Thr Gln Leu Ser Ser Glu Gly Trp Leu Gly Pro Ala Ser Ala Ala
    50                  55                  60

Met Ala Glu Ala Val Ala Pro Tyr Val Ala Trp Met Ser Ala Ala Ala
65                  70                  75                  80

Ala Gln Ala Glu Gln Ala Ala Thr Gln Ala Arg Ala Ala Ala Ala Ala
            85                  90                  95

Phe Glu Ala Ala Phe Ala Ala Thr Val Pro Pro Pro Leu Ile Ala Ala
            100                 105                 110

Asn Arg Ala Ser Leu Met Gln Leu Ile Ser Thr Asn Val Phe Gly Gln
            115                 120                 125

Asn Thr Ser Ala Ile Ala Ala Glu Ala Gln Tyr Gly
            130                 135                 140

(2) INFORMATION FOR SEQ ID NO:16:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:16:

Met Ala Ser Arg Phe Met Thr Asp Pro His Ala Met Arg Asp Met Ala
1               5                   10                  15

Gly Arg Phe Glu Val His Ala Gln Thr Val Glu Asp Glu Ala Arg Arg
            20                  25                  30

Met Trp Ala Ser Ala Gln Asn Ile Ser Gly Ala Gly Trp Ser Gly Met
        35                  40                  45

Ala Glu Ala Thr Ser Leu Asp Thr Met Thr
50                  55

(2) INFORMATION FOR SEQ ID NO:17:

(i) SEQUENCE CHARACTERISTICS:
        (A) LENGTH: 67 amino acids
        (B) TYPE: amino acid
        (C) STRANDEDNESS: single
        (D) TOPOLOGY: linear (ii) MOLECULE TYPE: peptide (vi) ORIGINAL SOURCE:

(A) ORGANISM: Mycobacterium tuberculosis (xi) SEQUENCE DESCRIPTION: SEQ ID NO:17:

```
Met Thr Ile Asn Tyr Gln Phe Gly Asp Val Asp Ala His Gly Ala Met
1               5                   10                  15

Ile Arg Ala Gln Ala Ala Ser Leu Glu Ala Glu His Gln Ala Ile Val
            20                  25                  30

Arg Asp Val Leu Ala Ala Gly Asp Phe Trp Gly Gly Ala Gly Ser Val
        35                  40                  45

Ala Cys Gln Glu Phe Ile Thr Gln Leu Gly Arg Asn Phe Gln Val Ile
    50                  55                  60

Tyr Glu Gln
65
```

(2) INFORMATION FOR SEQ ID NO:18:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:18:

```
Met Ala Ser Arg Phe Met Thr Asp Pro His Ala Met Arg Asp Met Ala
1               5                   10                  15

Gly Arg Phe Glu Val His Ala Gln Thr Val Glu Asp Glu Ala Arg Arg
            20                  25                  30

Met Trp Ala Ser Ala Gln Asn Ile Ser Gly Ala Gly Trp Ser Gly Met
        35                  40                  45

Ala Glu Ala Thr Ser Leu Asp Thr Met Thr
    50                  55
```

(2) INFORMATION FOR SEQ ID NO:19:

(i) SEQUENCE CHARACTERISTICS:
        (A) LENGTH: 94 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:19:

```
Met Thr Ile Asn Tyr Gln Phe Gly Asp Val Asp Ala His Gly Ala Met
1               5                   10                  15

Ile Arg Ala Gln Ala Ala Ser Leu Glu Ala Glu His Gln Ala Ile Val
            20                  25                  30

Arg Asp Val Leu Ala Ala Gly Asp Phe Trp Gly Gly Ala Gly Ser Val
        35                  40                  45

Ala Cys Gln Glu Phe Ile Thr Gln Leu Gly Arg Asn Phe Gln Val Ile
    50                  55                  60

Tyr Glu Gln Ala Asn Ala His Gly Gln Lys Val Gln Ala Ala Gly Asn
65                  70                  75                  80

Asn Met Ala Gln Thr Asp Ser Ala Val Gly Ser Ser Trp Ala
```

(2) INFORMATION FOR SEQ ID NO:20:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:20:

```
Asn Met Leu His Gly Val Arg Asp Gly Leu Val Arg Asp Ala Asn Asn
 1               5                  10                  15
Tyr Glu Gln Gln Glu Gln Ala Ser Gln Gln Ile Leu Ser Ser
            20                  25                  30
```

(2) INFORMATION FOR SEQ ID NO:21:

(i) SEQUENCE CHARACTERISTICS:
        (A) LENGTH: 94 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:21:

```
Met Thr Ile Asn Tyr Gln Phe Gly Asp Val Asp Ala His Gly Ala Met
 1               5                  10                  15
Ile Arg Ala Gln Ala Gly Leu Leu Glu Ala Glu His Gln Ala Ile Ile
            20                  25                  30
Arg Asp Val Leu Thr Ala Ser Asp Phe Trp Gly Gly Ala Gly Ser Ala
            35                  40                  45
Ala Cys Gln Gly Phe Ile Thr Gln Leu Gly Arg Asn Phe Gln Val Ile
        50                  55                  60
Tyr Glu Gln Ala Asn Ala His Gly Gln Lys Val Gln Ala Ala Gly Asn
65                  70                  75                  80
Asn Met Ala Gln Thr Asp Ser Ala Val Gly Ser Ser Trp Ala
            85                  90
```

(2) INFORMATION FOR SEQ ID NO:22:

(i) SEQUENCE CHARACTERISTICS:
        (A) LENGTH: 69 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:22:

```
Ala Arg Arg Met Trp Ala Ser Ala Gln Asn Ile Ser Gly Ala Gly Trp
 1               5                  10                  15
Ser Gly Met Ala Glu Ala Thr Ser Leu Asp Thr Met Ala Gln Met Asn
            20                  25                  30
```

-continued

```
Gln Ala Phe Arg Asn Ile Val Asn Met Leu His Gly Val Arg Asp Gly
        35                  40                  45
Leu Val Arg Asp Ala Asn Asn Tyr Glu Gln Gln Glu Gln Ala Ser Gln
 50                  55                  60
Gln Ile Leu Ser Ser
 65
```

(2) INFORMATION FOR SEQ ID NO:23:

(i) SEQUENCE CHARACTERISTICS:
        (A) LENGTH: 94 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:23:

```
Met Thr Ile Asn Tyr Gln Phe Gly Asp Val Asp Ala His Gly Ala Met
 1               5                  10                  15
Ile Arg Ala Gln Ala Gly Leu Leu Glu Ala Glu His Gln Ala Ile Ile
            20                  25                  30
Arg Asp Val Leu Thr Ala Ser Asp Phe Trp Gly Gly Ala Gly Ser Ala
        35                  40                  45
Ala Cys Gln Gly Phe Ile Thr Gln Leu Gly Arg Asn Phe Gln Val Ile
 50                  55                  60
Tyr Glu Gln Ala Asn Thr His Gly Gln Lys Val Gln Ala Ala Gly Asn
 65                  70                  75                  80
Asn Met Ala Gln Thr Asp Ser Ala Val Xaa Ser Ser Trp Ala
                85                  90
```

(2) INFORMATION FOR SEQ ID NO:24:

(i) SEQUENCE CHARACTERISTICS:
        (A) LENGTH: 52 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:24:

```
Gly Met Ala Glu Ala Thr Ser Xaa Asp Thr Met Thr Gln Met Asn Gln
 1               5                  10                  15
Ala Phe Arg Asn Ile Val Asn Met Leu His Gly Val Arg Asp Gly Leu
            20                  25                  30
Val Arg Asp Ala Asn Xaa Tyr Glu Gln Gln Glu Gln Ala Ser Gln Gln
        35                  40                  45
Ile Leu Ser Ser
 50
```

(2) INFORMATION FOR SEQ ID NO:25:

(i) SEQUENCE CHARACTERISTICS:
        (A) LENGTH: 94 amino acids
        (B) TYPE: amino acid
        (C) STRANDEDNESS: single (D) TOPOLOGY: linear (ii) MOLECULE TYPE: peptide (vi) ORIGINAL SOURCE:
            (A) ORGANISM: Mycobacterium tuberculosis (xi) SEQUENCE DESCRIPTION: SEQ ID NO:25:

Met Thr Ile Asn Tyr Gln Phe Gly Asp Val Asp Ala His Gly Ala Met
1               5                   10                  15

Ile Arg Ala Gln Ala Gly Ser Leu Glu Ala Glu His Gln Ala Ile Ile
                20                  25                  30

Ser Asp Val Leu Thr Ala Ser Asp Phe Trp Gly Gly Ala Gly Ser Ala
            35                  40                  45

Ala Cys Gln Gly Phe Ile Thr Gln Leu Gly Arg Asn Phe Gln Val Xaa
    50                  55                  60

Tyr Glu Gln Ala Asn Ala His Gly Gln Lys Val Gln Ala Ala Gly Asn
65                  70                  75                  80

Asn Met Ala Gln Thr Asp Ser Ala Val Gly Ser Ser Trp Ala
                85                  90

(2) INFORMATION FOR SEQ ID NO:26:

(i) SEQUENCE CHARACTERISTICS:
            (A) LENGTH: 98 amino acids
            (B) TYPE: amino acid
            (C) STRANDEDNESS: single
            (D) TOPOLOGY: linear (ii) MOLECULE TYPE: peptide (vi) ORIGINAL SOURCE:
            (A) ORGANISM: Mycobacterium tuberculosis (xi) SEQUENCE DESCRIPTION: SEQ ID NO:26:

Met Thr Ser Arg Phe Met Thr Asp Pro His Ala Met Arg Asp Met Ala
1               5                   10                  15

Gly Arg Phe Glu Val His Ala Gln Thr Val Glu Asp Glu Ala Arg Arg
                20                  25                  30

Met Trp Ala Ser Ala Gln Asn Ile Ser Gly Ala Gly Trp Ser Gly Met
            35                  40                  45

Ala Glu Ala Thr Ser Leu Asp Thr Met Ala Gln Met Asn Gln Ala Phe
    50                  55                  60

Arg Asn Ile Val Asn Met Leu His Gly Val Arg Asp Gly Leu Val Arg
65                  70                  75                  80

Asp Ala Asn Asn Tyr Glu Gln Gln Glu Gln Ala Ser Gln Gln Ile Leu
                85                  90                  95

Ser Ser (2) INFORMATION FOR SEQ ID NO:27:

(i) SEQUENCE CHARACTERISTICS:
            (A) LENGTH: 94 amino acids
            (B) TYPE: amino acid
            (C) STRANDEDNESS: single
            (D) TOPOLOGY: linear (ii) MOLECULE TYPE: peptide (vi) ORIGINAL SOURCE:
            (A) ORGANISM: Mycobacterium tuberculosis (xi) SEQUENCE DESCRIPTION: SEQ ID NO:27:

```
Met Thr Ile Asn Tyr Gln Phe Gly Asp Val Asp Ala His Gly Ala Met
1               5                   10                  15

Ile Arg Ala Xaa Ala Gly Leu Leu Glu Ala Glu His Gln Ala Ile Ile
                20                  25                  30

Ser Asp Val Leu Thr Ala Ser Asp Phe Trp Gly Gly Ala Gly Ser Ala
            35                  40                  45

Ala Cys Gln Gly Phe Ile Thr Gln Leu Gly Arg Asn Phe Gln Val Ile
50                      55                  60

Tyr Glu Gln Ala Asn Ala His Gly Gln Lys Val Gln Ala Ala Gly Asn
65                      70                  75                  80

Asn Met Ala Gln Thr Asp Ser Ala Val Gly Ser Ser Trp Ala
                85                  90
```

(2) INFORMATION FOR SEQ ID NO:28:

(i) SEQUENCE CHARACTERISTICS:
        (A) LENGTH: 81 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:28:

```
Arg Phe Glu Val His Ala Gln Thr Val Glu Asp Glu Ala Arg Arg Met
1               5                   10                  15

Trp Ala Ser Ala Gln Asn Ile Ser Gly Ala Gly Trp Ser Gly Met Ala
                20                  25                  30

Xaa Ala Thr Ser Leu Asp Thr Met Ala Gln Met Asn Gln Ala Phe Arg
            35                  40                  45

Asn Ile Val Asn Met Leu His Gly Val Arg Asp Gly Leu Val Arg Asp
50                      55                  60

Ala Asn Asn Tyr Glu Gln Gln Glu Gln Ala Ser Gln Gln Ile Leu Ser
65                      70                  75                  80

Ser
```

(2) INFORMATION FOR SEQ ID NO:29:

(i) SEQUENCE CHARACTERISTICS:
        (A) LENGTH: 94 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:29:

```
Met Thr Ile Asn Tyr Gln Phe Gly Asp Val Asp Ala His Gly Ala Met
1               5                   10                  15

Ile Arg Ala Leu Ala Gly Leu Leu Glu Ala Glu His Gln Ala Ile Ile
                20                  25                  30

Ser Asp Val Leu Thr Ala Ser Asp Phe Trp Gly Gly Ala Gly Ser Ala
            35                  40                  45

Ala Cys Gln Gly Phe Ile Thr Gln Leu Gly Arg Asn Phe Gln Val Ile
50                      55                  60
```

```
Tyr Glu Gln Ala Asn Ala His Gly Gln Lys Val Gln Ala Ala Gly Asn
65                  70                  75                  80

Asn Met Ala Gln Thr Asp Ser Ala Val Gly Ser Ser Trp Ala
                85                  90
```

(2) INFORMATION FOR SEQ ID NO:30:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:30:

```
Gln Glu Gln Ala Ser Gln Gln Ile Leu Ser Ser
1               5                   10
```

(2) INFORMATION FOR SEQ ID NO:31:

(i) SEQUENCE CHARACTERISTICS:
        (A) LENGTH: 94 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:31:

```
Met Thr Ile Asn Tyr Gln Phe Gly Asp Val Asp Ala His Gly Ala Met
1                   5                   10                  15

Ile Arg Ala Gln Ala Gly Leu Leu Glu Ala Glu His Gln Ala Ile Ile
                20                  25                  30

Arg Asp Val Leu Thr Ala Ser Asp Phe Trp Gly Gly Ala Gly Ser Ala
            35                  40                  45

Ala Cys Gln Gly Phe Ile Thr Gln Leu Gly Arg Asn Phe Gln Val Ile
50                  55                  60

Tyr Glu Gln Ala Asn Ala His Gly Gln Lys Val Gln Ala Ala Gly Asn
65                  70                  75                  80

Asn Met Ala Gln Thr Asp Ser Ala Val Gly Ser Ser Trp Ala
                85                  90
```

(2) INFORMATION FOR SEQ ID NO:32:

(i) SEQUENCE CHARACTERISTICS:
        (A) LENGTH: 99 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:32:

```
Met Ser Phe Val Thr Thr Gln Pro Glu Ala Leu Ala Ala Ala Ala
1               5                   10                  15

Asn Leu Gln Gly Ile Gly Thr Thr Met Asn Ala Gln Asn Ala Ala Ala
```

```
                20                  25                  30
Ala Ala Pro Thr Thr Gly Val Val Pro Ala Ala Asp Glu Val Ser
            35                  40                  45

Ala Leu Thr Ala Ala Gln Phe Ala Ala His Ala Gln Met Tyr Gln Thr
        50                  55                  60

Val Ser Ala Gln Ala Ala Ala Ile His Glu Met Phe Val Asn Thr Leu
65                  70                  75                  80

Val Ala Ser Ser Gly Ser Tyr Ala Ala Thr Glu Ala Ala Asn Ala Ala
                85                  90                  95

Ala Ala Gly
```

(2) INFORMATION FOR SEQ ID NO:33:

(i) SEQUENCE CHARACTERISTICS:
        (A) LENGTH: 99 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:33:

```
Met Ser Phe Val Thr Thr Gln Pro Glu Ala Leu Ala Ala Ala Ala Ala
1               5                   10                  15

Asn Leu Gln Gly Ile Gly Thr Thr Met Asn Ala Gln Asn Ala Ala Ala
                20                  25                  30

Ala Ala Pro Thr Thr Gly Val Val Pro Ala Ala Ala Asp Glu Val Ser
            35                  40                  45

Ala Leu Thr Ala Ala Gln Phe Ala Ala His Ala Gln Met Tyr Gln Thr
        50                  55                  60

Val Ser Ala Gln Ala Ala Ala Ile His Glu Met Phe Val Asn Thr Leu
65                  70                  75                  80

Val Ala Ser Ser Gly Ser Tyr Ala Ala Thr Glu Ala Ala Asn Ala Ala
                85                  90                  95

Ala Ala Gly
```

(2) INFORMATION FOR SEQ ID NO:34:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:34:

```
Asp Pro His Ala Met Arg Asp Met Ala Gly Arg Phe Glu Val His
1               5                   10                  15
```

(2) INFORMATION FOR SEQ ID NO:35:

(i) SEQUENCE CHARACTERISTICS:
        (A) LENGTH: 15 amino acids
        (B) TYPE: amino acid
        (C) STRANDEDNESS: single
        (D) TOPOLOGY: linear

```
    (ii) MOLECULE TYPE: peptide (vi) ORIGINAL SOURCE:
         (A) ORGANISM: Mycobacterium tuberculosis (xi) SEQUENCE DESCRIPTION: SEQ ID NO:35:

Arg Asp Met Ala Gly Arg Phe Glu Val His Ala Gln Thr Val Glu
1               5                   10                  15

(2) INFORMATION FOR SEQ ID NO:36:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
         (A) ORGANISM: Mycobacterium tuberculosis (xi) SEQUENCE DESCRIPTION: SEQ ID NO:36:

Arg Phe Glu Val His Ala Gln Thr Val Glu Asp Glu Ala Arg Arg
1               5                   10                  15

(2) INFORMATION FOR SEQ ID NO:37:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
         (A) ORGANISM: Mycobacterium tuberculosis (xi) SEQUENCE DESCRIPTION: SEQ ID NO:37:

Ala Gln Thr Val Glu Asp Glu Ala Arg Arg Met Trp Ala Ser Ala
1               5                   10                  15

(2) INFORMATION FOR SEQ ID NO:38:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
         (A) ORGANISM: Mycobacterium tuberculosis (xi) SEQUENCE DESCRIPTION: SEQ ID NO:38:

Asp Glu Ala Arg Arg Met Trp Ala Ser Ala Gln Asn Ile Ser Gly
1               5                   10                  15

(2) INFORMATION FOR SEQ ID NO:39:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide
```

```
    (vi) ORIGINAL SOURCE:
         (A) ORGANISM: Mycobacterium tuberculosis (xi) SEQUENCE DESCRIPTION: SEQ ID NO:39:

Met Trp Ala Ser Ala Gln Asn Ile Ser Gly Ala Gly Trp Ser Gly
 1               5                  10                  15

(2) INFORMATION FOR SEQ ID NO:40:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
         (A) ORGANISM: Mycobacterium tuberculosis (xi) SEQUENCE DESCRIPTION: SEQ ID NO:40:

Gln Asn Ile Ser Gly Ala Gly Trp Ser Gly Met Ala Glu Ala Thr
 1               5                  10                  15

(2) INFORMATION FOR SEQ ID NO:41:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (vi) ORIGINAL SOURCE:
         (A) ORGANISM: Mycobacterium tuberculosis (xi) SEQUENCE DESCRIPTION: SEQ ID NO:41:

Ala Gly Trp Ser Gly Met Ala Glu Ala Thr Ser Leu Asp Thr Met Thr
 1               5                  10                  15

(2) INFORMATION FOR SEQ ID NO:42:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
         (A) ORGANISM: Mycobacterium tuberculosis (xi) SEQUENCE DESCRIPTION: SEQ ID NO:42:

Met Ala Glu Ala Thr Ser Leu Asp Thr Met Ala Gln Met Asn Gln
 1               5                  10                  15

(2) INFORMATION FOR SEQ ID NO:43:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
         (A) ORGANISM: Mycobacterium tuberculosis
```

-continued (xi) SEQUENCE DESCRIPTION: SEQ ID NO:43:

Ser Leu Asp Thr Met Ala Gln Met Asn Gln Ala Phe Arg Asn Ile
1               5                   10                  15

(2) INFORMATION FOR SEQ ID NO:44:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:44:

Ala Gln Met Asn Gln Ala Phe Arg Asn Ile Val Asn Met Leu His
1               5                   10                  15

(2) INFORMATION FOR SEQ ID NO:45:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:45:

Ala Phe Arg Asn Ile Val Asn Met Leu His Gly Val Arg Asp Gly
1               5                   10                  15

(2) INFORMATION FOR SEQ ID NO:46:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:46:

Val Asn Met Leu His Gly Val Arg Asp Gly Leu Val Arg Asp Ala
1               5                   10                  15

(2) INFORMATION FOR SEQ ID NO:47:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:47:

Gly Val Arg Asp Gly Leu Val Arg Asp Ala Asn Asn Tyr Glu Gln (2) INFORMATION FOR SEQ ID NO:48:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:48:

```
Leu Val Arg Asp Ala Asn Asn Tyr Glu Gln Gln Glu Gln Ala Ser
1               5                   10                  15
```

(2) INFORMATION FOR SEQ ID NO:49:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:49:

```
Asn Asn Tyr Glu Gln Gln Glu Gln Ala Ser Gln Gln Ile Leu Ser Ser
1               5                   10                  15
```

(2) INFORMATION FOR SEQ ID NO:50:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:50:

```
Met Ala Ser Arg Phe Met Thr Asp Pro His Ala Met Arg Asp Met Ala
1               5                   10                  15
Gly
```

(2) INFORMATION FOR SEQ ID NO:51:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:51:

```
Met Thr Ile Asn Tyr Gln Phe Gly Asp Val Asp Ala His Gly Ala
1               5                   10                  15
```

(2) INFORMATION FOR SEQ ID NO:52:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:52:

```
Gln Phe Gly Asp Val Asp Ala His Gly Ala Met Ile Arg Ala Gln
1               5                   10                  15
```

(2) INFORMATION FOR SEQ ID NO:53:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:53:

```
Asp Ala His Gly Ala Met Ile Arg Ala Gln Ala Ala Ser Leu Glu
1               5                   10                  15
```

(2) INFORMATION FOR SEQ ID NO:54:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:54:

```
Met Ile Arg Ala Gln Ala Ala Ser Leu Glu Ala Glu His Gln Ala
1               5                   10                  15
```

(2) INFORMATION FOR SEQ ID NO:55:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:55:

```
Ala Ala Ser Leu Glu Ala Glu His Gln Ala Ile Val Arg Asp Val
1               5                   10                  15
```

(2) INFORMATION FOR SEQ ID NO:56:

(i) SEQUENCE CHARACTERISTICS:
    (A) LENGTH: 15 amino acids
    (B) TYPE: amino acid
    (C) STRANDEDNESS: single
    (D) TOPOLOGY: linear (ii) MOLECULE TYPE: peptide (vi) ORIGINAL SOURCE:
    (A) ORGANISM: Mycobacterium tuberculosis (xi) SEQUENCE DESCRIPTION: SEQ ID NO:56:

```
Ala Glu His Gln Ala Ile Val Arg Asp Val Leu Ala Ala Gly Asp
1               5                  10                  15
```

(2) INFORMATION FOR SEQ ID NO:57:

(i) SEQUENCE CHARACTERISTICS:
    (A) LENGTH: 15 amino acids
    (B) TYPE: amino acid
    (C) STRANDEDNESS: single
    (D) TOPOLOGY: linear (ii) MOLECULE TYPE: peptide (vi) ORIGINAL SOURCE:
    (A) ORGANISM: Mycobacterium tuberculosis (xi) SEQUENCE DESCRIPTION: SEQ ID NO:57:

```
Ile Val Arg Asp Val Leu Ala Ala Gly Asp Phe Trp Gly Gly Ala
1               5                  10                  15
```

(2) INFORMATION FOR SEQ ID NO:58:

(i) SEQUENCE CHARACTERISTICS:
    (A) LENGTH: 16 amino acids
    (B) TYPE: amino acid
    (C) STRANDEDNESS: single
    (D) TOPOLOGY: linear (ii) MOLECULE TYPE: peptide (vi) ORIGINAL SOURCE:
    (A) ORGANISM: Mycobacterium tuberculosis (xi) SEQUENCE DESCRIPTION: SEQ ID NO:58:

```
Leu Ala Ala Gly Asp Phe Trp Gly Gly Ala Gly Ser Val Ala Cys Gln
1               5                  10                  15
```

(2) INFORMATION FOR SEQ ID NO:59:

(i) SEQUENCE CHARACTERISTICS:
    (A) LENGTH: 15 amino acids
    (B) TYPE: amino acid
    (C) STRANDEDNESS: single
    (D) TOPOLOGY: linear (ii) MOLECULE TYPE: peptide (vi) ORIGINAL SOURCE:
    (A) ORGANISM: Mycobacterium tuberculosis (xi) SEQUENCE DESCRIPTION: SEQ ID NO:59:

```
Phe Trp Gly Gly Ala Gly Ser Val Ala Cys Gln Glu Phe Ile Thr
1               5                  10                  15
```

(2) INFORMATION FOR SEQ ID NO:60:

(i) SEQUENCE CHARACTERISTICS:
    (A) LENGTH: 15 amino acids

```
            (B) TYPE: amino acid
            (C) STRANDEDNESS: single
            (D) TOPOLOGY: linear (ii) MOLECULE TYPE: peptide (vi) ORIGINAL SOURCE:
            (A) ORGANISM: Mycobacterium tuberculosis (xi) SEQUENCE DESCRIPTION: SEQ ID NO:60:

Gly Ser Val Ala Cys Gln Glu Phe Ile Thr Gln Leu Gly Arg Asn
1               5                   10                  15

(2) INFORMATION FOR SEQ ID NO:61:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: peptide (vi) ORIGINAL SOURCE:
            (A) ORGANISM: Mycobacterium tuberculosis (xi) SEQUENCE DESCRIPTION: SEQ ID NO:61:

Gln Glu Phe Ile Thr Gln Leu Gly Arg Asn Phe Gln Val Ile Tyr Glu
1               5                   10                  15

Gln Ala (2) INFORMATION FOR SEQ ID NO:62:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (vi) ORIGINAL SOURCE:
            (A) ORGANISM: Mycobacterium tuberculosis (xi) SEQUENCE DESCRIPTION: SEQ ID NO:62:

Arg Asn Phe Gln Val Ile Tyr Glu Gln Ala Asn Ala His Gly Gln
1               5                   10                  15

(2) INFORMATION FOR SEQ ID NO:63:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (vi) ORIGINAL SOURCE:
            (A) ORGANISM: Mycobacterium tuberculosis (xi) SEQUENCE DESCRIPTION: SEQ ID NO:63:

Ile Tyr Glu Gln Ala Asn Ala His Gly Gln Lys Val Gln Ala Ala
1               5                   10                  15

(2) INFORMATION FOR SEQ ID NO:64:

(i) SEQUENCE CHARACTERISTICS:
            (A) LENGTH: 15 amino acids
            (B) TYPE: amino acid
```

(C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:64:

Asn Ala His Gly Gln Lys Val Gln Ala Ala Gly Asn Asn Met Ala
1               5                  10                  15

(2) INFORMATION FOR SEQ ID NO:65:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:65:

Lys Val Gln Ala Ala Gly Asn Asn Met Ala Gln Thr Asp Ser Ala
1               5                  10                  15

(2) INFORMATION FOR SEQ ID NO:66:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:66:

Gly Asn Asn Met Ala Gln Thr Asp Ser Ala Val Gly Ser Ser Trp Ala
1               5                  10                  15

(2) INFORMATION FOR SEQ ID NO:67:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:67:

Asp Ala His Gly Ala Met Ile Arg Ala Leu Ala Gly Leu Leu Glu
1               5                  10                  15

(2) INFORMATION FOR SEQ ID NO:68:

(i) SEQUENCE CHARACTERISTICS:
        (A) LENGTH: 15 amino acids
        (B) TYPE: amino acid
        (C) STRANDEDNESS: single
        (D) TOPOLOGY: linear

```
        (ii) MOLECULE TYPE: peptide (vi) ORIGINAL SOURCE:
             (A) ORGANISM: Mycobacterium tuberculosis (xi) SEQUENCE DESCRIPTION: SEQ ID NO:68:

Asp Ala His Gly Ala Met Ile Arg Ala Gln Ala Gly Leu Leu Glu
1               5                  10                  15

(2) INFORMATION FOR SEQ ID NO:69:

(i) SEQUENCE CHARACTERISTICS:
             (A) LENGTH: 15 amino acids
             (B) TYPE: amino acid
             (C) STRANDEDNESS: single
             (D) TOPOLOGY: linear (ii) MOLECULE TYPE: peptide (vi) ORIGINAL SOURCE:
             (A) ORGANISM: Mycobacterium tuberculosis (xi) SEQUENCE DESCRIPTION: SEQ ID NO:69:

Met Ile Arg Ala Leu Ala Gly Leu Leu Glu Ala Glu His Gln Ala
1               5                  10                  15

(2) INFORMATION FOR SEQ ID NO:70:

(i) SEQUENCE CHARACTERISTICS:
             (A) LENGTH: 15 amino acids
             (B) TYPE: amino acid
             (C) STRANDEDNESS: single
             (D) TOPOLOGY: linear (ii) MOLECULE TYPE: peptide (vi) ORIGINAL SOURCE:
             (A) ORGANISM: Mycobacterium tuberculosis (xi) SEQUENCE DESCRIPTION: SEQ ID NO:70:

Met Ile Arg Ala Gln Ala Gly Leu Leu Glu Ala Glu His Gln Ala
1               5                  10                  15

(2) INFORMATION FOR SEQ ID NO:71:

(i) SEQUENCE CHARACTERISTICS:
             (A) LENGTH: 15 amino acids
             (B) TYPE: amino acid
             (C) STRANDEDNESS: single
             (D) TOPOLOGY: linear (ii) MOLECULE TYPE: peptide (vi) ORIGINAL SOURCE:
             (A) ORGANISM: Mycobacterium tuberculosis (xi) SEQUENCE DESCRIPTION: SEQ ID NO:71:

Ala Gly Leu Leu Glu Ala Glu His Gln Ala Ile Ile Ser Asp Val
1               5                  10                  15

(2) INFORMATION FOR SEQ ID NO:72:

(i) SEQUENCE CHARACTERISTICS:
             (A) LENGTH: 15 amino acids
             (B) TYPE: amino acid
             (C) STRANDEDNESS: single
             (D) TOPOLOGY: linear (ii) MOLECULE TYPE: peptide (vi) ORIGINAL SOURCE:
```

(A) ORGANISM: Mycobacterium tuberculosis (xi) SEQUENCE DESCRIPTION: SEQ ID NO:72:

Ala Gly Leu Leu Glu Ala Gl

```
Ile Ile Arg Asp Val Leu Thr Ala Ser Asp Phe Trp Gly Gly Ala
1               5                   10                  15
```

(2) INFORMATION FOR SEQ ID NO:77:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:77:

```
Leu Thr Ala Ser Asp Phe Trp Gly Gly Ala Gly Ser Ala Ala Cys Gln
1               5                   10                  15
```

(2) INFORMATION FOR SEQ ID NO:78:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:78:

```
Phe Trp Gly Gly Ala Gly Ser Ala Ala Cys Gln Gly Phe Ile Thr
1               5                   10                  15
```

(2) INFORMATION FOR SEQ ID NO:79:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:79:

```
Gly Ser Ala Ala Cys Gln Gly Phe Ile Thr Gln Leu Gly Arg Asn
1               5                   10                  15
```

(2) INFORMATION FOR SEQ ID NO:80:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:80:

```
Gln Gly Phe Ile Thr Gln Leu Gly Arg Asn Phe Gln Val Ile Tyr
1               5                   10                  15
```

(2) INFORMATION FOR SEQ ID NO:81:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:81:

```
Val Thr Thr Asn Phe Phe Gly Val Asn Thr Ile Pro Ile Ala Leu Asn
1               5                   10                  15

Glu Ala Asp Tyr Leu Arg Met Trp Ile
            20                  25
```

(2) INFORMATION FOR SEQ ID NO:82:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:82:

```
Asn Glu Ala Asp Tyr Leu Arg Met Trp Ile Gln Ala Ala Thr Val Met
1               5                   10                  15

Ser His Tyr Gln Ala Val Ala His Glu
            20                  25
```

(2) INFORMATION FOR SEQ ID NO:83:

(i) SEQUENCE CHARACTERISTICS:
        (A) LENGTH: 967 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:83:

```
TGAGCGCCAA CCCTACCGTC GGTTCGTCAC ACGGACCGCA TGGCCTGCTC CGCGGACTGC      60

CGCTAGGGTC GCGGATCACT CGGCGTAGCG GCGCCTTTGC CCACCGATAT GGGTTCCGTC     120

ACAGTGTGGT TGCCCGCCCG CCATCGGCCG GATAACGCCA TGACCTCAGC TCGGCAGAAA     180

TGACAATGCT CCCAAAGGCG TGAGCACCCG AAGACAACTA AGCAGGAGAT CGCATGCCGT     240

TTGTGACTAC CCAACCAGAA GCACTGGCGG CGGCGGCCGG CAGTCTGCAG GGAATCGGCT     300

CCGCATTGAA CGCCCAGAAT GCGGCTGCGG CGACTCCCAC GACGGGGTG GTCCGGCGGC      360

CGCCGATGAA NTGTCGGCGC TGACGGCGGC TCAGTTCGCG GCACACGCCC AGATCTATCA     420

GGCCGTCAGC GCCCAGGCCG CGGCGATTCA CGAGATGTTC GTCAACACTC TACAGATGAG     480

CTCAGGGTCG TATGCTGCTA CCGAGGCCGC CAACGCGGCC GCGGCCGGNT AGAGGAGTCA     540

CTGCGATGGA TTTTGGGGCG TTGCCGCCGG AGGTCAATTC GGTGCGGATG TATGCCGTTC     600

CTGGCTCGGC ACCAATGGTC GCTGCGGCGT CGGCCTGGAA CGGGTTGGCC GCGGAGCTGA     660
```

-continued

```
GTTCGGCGGC CACCGGTTAT GAGACGGTGA TCACTCAGCT CAGCAGTGAG GGGTGGCTAG      720

GTCCGGCGTC AGCGGCGATG GCCGAGGCAG TTGCGCCGTA TGTGGCGTGG ATGAGTGCCG      780

CTGCGGCGCA AGCCGAGCAG GCGGCCACAC AGGCCAGGGC CGCCGCGGCC GCTTTTGAGG      840

CGGCGTTTGC CGCGACGGTG CCTCCGCCGT TGATCGCGGC CAACCGGGCT TCGTTGATGC      900

AGCTGATCTC GACGAATGTC TTTGGTCAGA CACCTCGGC GATCGCGGCC GCCGAAGCTC       960

AGTACGG                                                               967
```

(2) INFORMATION FOR SEQ ID NO:84:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:84:

```
Met Ser Phe Val Thr Thr Gln Pro Glu Ala Leu Ala Ala Ala Ala
1               5                  10                  15
```

(2) INFORMATION FOR SEQ ID NO:85:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:85:

```
Thr Gln Pro Glu Ala Leu Ala Ala Ala Ala Asn Leu Gln Gly
1               5                  10                  15
```

(2) INFORMATION FOR SEQ ID NO:86:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:86:

```
Leu Ala Ala Ala Ala Ala Asn Leu Gln Gly Ile Gly Thr Thr Met
1               5                  10                  15
```

(2) INFORMATION FOR SEQ ID NO:87:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:87:

```
Ala Asn Leu Gln Gly Ile Gly Thr Thr Met Asn Ala Gln Asn Ala
1               5                  10                  15
```

(2) INFORMATION FOR SEQ ID NO:88:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:88:

Ile Gly Thr Thr Met Asn Ala Gln Asn Ala Ala Ala Ala Ala Pro
 1               5                  10                  15

(2) INFORMATION FOR SEQ ID NO:89:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:89:

Asn Ala Gln Asn Ala Ala Ala Ala Ala Pro Thr Thr Gly Val Val
 1               5                  10                  15

(2) INFORMATION FOR SEQ ID NO:90:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:90:

Ala Ala Ala Ala Pro Thr Thr Gly Val Val Pro Ala Ala Ala Asp
 1               5                  10                  15

(2) INFORMATION FOR SEQ ID NO:91:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:91:

Thr Thr Gly Val Val Pro Ala Ala Ala Asp Glu Val Ser Ala Leu
 1               5                  10                  15

(2) INFORMATION FOR SEQ ID NO:92:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:92:

Pro Ala Ala Ala Asp Glu Val Ser Ala Leu Thr Ala Ala Gln Phe
 1               5                  10                  15

(2) INFORMATION FOR SEQ ID NO:93:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:93:

Glu Val Ser Ala Leu Thr Ala Ala Gln Phe Ala Ala His Ala Gln
 1               5                  10                  15

(2) INFORMATION FOR SEQ ID NO:94:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:94:

Thr Ala Ala Gln Phe Ala Ala His Ala Gln Met Tyr Gln Thr Val
 1               5                  10                  15

(2) INFORMATION FOR SEQ ID NO:95:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:95:

Ala Ala His Ala Gln Met Tyr Gln Thr Val Ser Ala Gln Ala Ala
 1               5                  10                  15

(2) INFORMATION FOR SEQ ID NO:96:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:96:

Met Tyr Gln Thr Val Ser Ala Gln Ala Ala Ala Ile His Glu Met Phe
 1               5                  10                  15

(2) INFORMATION FOR SEQ ID NO:97:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:97:

Ser Ala Gln Ala Ala Ala Ile His Glu Met Phe Val Asn Thr Leu
 1               5                  10                  15

(2) INFORMATION FOR SEQ ID NO:98:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:98:

```
Ala Ile His Glu Met Phe Val Asn Thr Leu Val Ala Ser Ser Gly
 1               5                  10                  15
```

(2) INFORMATION FOR SEQ ID NO:99:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:99:

```
Phe Val Asn Thr Leu Val Ala Ser Ser Gly Ser Tyr Ala Ala Thr
 1               5                  10                  15
```

(2) INFORMATION FOR SEQ ID NO:100:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:100:

```
Val Ala Ser Ser Gly Ser Tyr Ala Ala Thr Glu Ala Ala Asn Ala
 1               5                  10                  15
```

(2) INFORMATION FOR SEQ ID NO:101:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:101:

```
Ser Tyr Ala Ala Thr Glu Ala Ala Asn Ala Ala Ala Ala Gly
 1               5                  10
```

(2) INFORMATION FOR SEQ ID NO:102:

(i) SEQUENCE CHARACTERISTICS:
        (A) LENGTH: 1784 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:102:

```
ATTCGTTCCT GCCGCAGCTA AATCCCGGGG ACATCGTCGC CGGCCAGTAC GAGGTCAAAG    60
```

```
GCTGCATCGC GCACGGCGGA CTGGGCTGGA TCTACCTCGC TCTCGACCGC AATGTCAACG      120

GCCGTCCGGT GGTGCTCAAG GGCCTGGTGC ATTCCGGTGA TGCCGAAGCG CAGGCAATGG      180

CGATGGCCGA ACGCCAGTTC CTGGCCGAGG TGGTGCACCC GTCGATCGTG CAGATCTTCA      240

ACTTTGTCGA GCACACCGAC AGGCACGGGG ATCCGGTCGG CTACATCGTG ATGGAATACG      300

TCGGCGGGCA ATCGCTCAAA CGCAGCAAGG GTCANAAACT GCCCGTCGCG GAGGCCATCG      360

CCTACCTGCT GGAGATCCTG CCGGCGCTGA GCTACCTGCA TTCCATCGGC TTGGTCTACA      420

ACGACCTGAA GCCGGAAAAC ATCATGCTGA CCGAGGAACA GCTCAAGCTG ATCGACCTGG      480

GCGCGGTATC GCGGATCAAC TCGTTCGGCT ACCTCTACGG GACCCCAGGC TTCCAGGCGC      540

CCGAGATCGT GCGGACCGGT CCGACGGTGG CCACCGACAT CTACACCGTG GGACGCACGC      600

TCGCGGCGCT CACGCTGGAC CTGCCCACCC GCAATGGCCG TTATGTGGAT GGGCTACCCG      660

AAGACGACCC GGTGCTGAAA ACCTACGACT CTTACGGCCG GTTGCTGCGC AGGGCCATCG      720

ACCCCGATCC GCGGCAACGG TTCACCACCG CCGAAGAGAT GTCCGCGCAA TTGACGGGCG      780

TGTTGCGGGA GGTGGTCGCC CAGACACCGG GGTGCCGCGG CCAGGCTATC AACGATCTTC      840

AGTCCCAGTC GGTCGACATT TGGAGTGGAC TGCTGGTGGC GCACACCGAC GTGTATCTGG      900

ACGGGCAGGT GCACGCGGAG AAGCTGACCG CCAACGAGAT CGTGACCGCG CTGTCGGTGC      960

CGCTGGTCGA TCCGACCGAC GTCGCAGCTT CGGTCCTGCA GGCCACGGTG CTCTCCCAGC     1020

CGGTGCAGAC CCTAGACTCG NTGCGCGCGG CCCGCCACGG TGCGCTGGAC GCCGACGGCG     1080

TCGATTNTCC GAGTCAGTGG AGCTGCCGCT AATGGAAGTC CGCGCGCTGC TGGATCTCGG     1140

CGATGTGGCC AAGGCCACCC GAAAACTCGA CGATCTGGCC GAACGCGTTG GCTGGCGATG     1200

GCGATTGGTC TGGTACCGGG CCGTCGCCGA GCTGCTCACC GGCGACTATG ACTCGGCCAC     1260

CAAACATTTC ACCGAGGTGC TGGATACCTT TCCCGGCGAG CTGGCGCCCA AGCTCGCCCT     1320

GGCCGCCACC GCCGAACTAG CCGGCAACAC CGACGAACAC AAGTTCTATC AGACGGTGTG     1380

GAGCACCAAC GACGGCGTGA TCTCGGCGGC TTTCGGACTG GCCAGAGCCC GGTCGGCCGA     1440

AGGTGATCGG GTCGGCGCCG TGCGCACGCT CGACGAGGTA CCGCCCACTT CTCGGCATTT     1500

CACCACGGCA CGGCTGACCA GCGCGGTGAC TCTGTTGTCC GGCCGGTCAA CGAGTGAAGT     1560

CACCGAGGAA CAGATCCGCG ACGCCGCCCG AAGAGTGGAG GCGCTGCCCC CGACCGAACC     1620

ACGCGTGCTG CAGATCCGCG CCCTGGTGCT GGGTGGCGCG CTGGACTGGC TGAAGGACAA     1680

CAAGGCCAGC ACCAACCACA TCCTCGGTTT CCCGTTCACC AGTCACGGGC TGCGGCTGGG     1740

TGTCGAGGCG TCACTGCGCA GCCTGGCCCG GGTAGCTCCC ACTC                      1784

(2) INFORMATION FOR SEQ ID NO:103:

(i) SEQUENCE CHARACTERISTICS:
        (A) LENGTH: 766 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:103:

ACAARACACT CGGYGGCKGC CGMTCCGGCC TGATCGTCGG TGATCAGCYT CGTGCCAAAY       60

TCGGCACAAG GTGCGCGCTR CCCAANGAGT TCTTCGCCGC RGTGCGMGCM KAACTGGCCT      120

ATCNTGGTTG GGTGCCGTCC CGCANAACCC GCGAACTTAA ACCCATTTTA ACCGGGCAGG      180

AAGTTTCCTA CATYTACCCN RGSMANCCAA CCGGGCCGCC NANAAMTCCG TCCTGGANTC      240
```

```
CGANCGGTTC CCGGTGTTCG CCGCACTGCT GACCGGCACG GARTATCCGC AGGCGGCGTT      300

GGCCAACGCG TGGGTGCAAC TGGCCTACGG TGCGCACCAS GACGCCATCA CCGGCTCGGA      360

GTCCGACCAG GTACTCAATG CTGGCGACCA CACCAGCCAG CAGACCAAAC TGGTGCACGC      420

CGATCTCCAG GCGCGCCGGC CCGGTGGCAT ACGGATTGGT CGAAACCAAT CCGAAGGAAT      480

TCATCACGGA CGGTCACGGA AAACGATCGC CCCAATGGGN GGACNACCCN AGCCAGGCGN      540

ATTNACCGTT NAACAAGTTG GNGTAGGTTC TTTGATATCG AKCAACCGAT ACGGAKCGGM      600

CCGCGGAATG GTAGACCACC ACCAGTGCCC NCAMGTMGTG CACCAGTTTG GTCATCGCCC      660

GCAGATCGGT GACCCCGCCA AGCGTTCCGG ATGCGGAGAT GASGGTGACC AGCCYGGTTG      720

ACCTGTTGAT CAGGTTNTCC CAGTGCCACG TCGGCAGCTG GCCGGT                    766
```

(2) INFORMATION FOR SEQ ID NO:104:

(i) SEQUENCE CHARACTERISTICS:
        (A) LENGTH: 1231 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:104:

```
CGGCACGAGA ATGTCGCCTG TGCCTCGATA GCCACTTGCG TGTGGTCGCG CTGCCAGCGG       60

GTCAGCCAGG TCGCCTGGTC CAGGCCATCG GGCCGGCGCA GGAGCGCGAT GTTGGCCAGA      120

CCCGGTGTAC GAGAACCGGA CTCGACNAAG TGTCGGCGCT GACGGCGGCT CAGTTCGCGG      180

CACACGCCCA GATCTATCAG GCCGTCAGCG CCCAGGCCGC GGCGATTCAC GAGATGTTCG      240

TCAACACTCT ACAGATNANC TCAGGGTCGT ATGCTGCTAC CGAGGCCGCC AACGCGGCCG      300

CGGCCGGCTA GAGGAGTCAC TGCGATGGAT TTTGGGGCGT TGCCGCCGGA GGTCAATTCG      360

GTGCGGATGT ATGCCGGTCC TGGCTCGGCA CCAATGGTCG CTGCGGCGTC GGCCTGGAAC      420

GGGTTGGCCG CGGAGCTGAG TTCGGCGGCC ACCGGTTATG AGACGGTGAT CACTCAGCTC      480

AGCAGTGAGG GGTGGCTAGG TCCGGCGTCA GCGGCGATGG CCGAGGCAGT TGCGCCGTAT      540

GTGGCGTGGA TGAGTGCCGC TGCGGCGCAA GCCGAGCAGG CGGCCACACA GGCCAGGGCC      600

GCCGCGGCCG CTTTTGAGGC GGCGTTTGCC GCGACGGTGC CTCCGCCGTT GATCGCGGCC      660

AACCGGGCTT CGTTGATGCA GCTGATCTCG ACGAATGTCT TTGGTCAGAA CACCTCGGCG      720

ATCGCGGCCG CCGAAGCTCA GTACGGCGAG ATGTGGGCCC AAGACTCCGC GGCGATGTAT      780

GCCTACGCGG GCAGTTCGGC GAGCGCCTCG GCGGTCACGC CGTTTAGCAC GCCGCCGCAG      840

ATTGCCAACC CGACCGCTCA GGGTACGCAG GCCGCGGCCG TGGCCACCGC CGCCGGTACC      900

GCCCAGTCGA CGCTGACGGA GATGATCACC GGGCTACCCA ACGCGCTGCA AAGCCTCACC      960

TCACNTCTGT TGCAGTCGTC TAACGGTCCG CTGTCGTGGC TGTGGCAGAT CTTGTTCGGC     1020

ACGCCCAATT TCCCCACCTC AATTTCGGCA CTGCTGACCG ACCTGCAGCC CTACGCGAGC     1080

TTNTTNTATA ACACCGAGGG CCTGCCGTAC TTCAGCATCG GCATGGGCAA CAACTTCATT     1140

CAGTCGGCCA AGACCCTGGG ATTGATCGGC TAGGCGGCAC CGGCTGCGGT CGCGGNTGCT     1200

GGGGATNCCG CCAAGGGCTT GCCTCGTGCC G                                    1231
```

(2) INFORMATION FOR SEQ ID NO:105:

(i) SEQUENCE CHARACTERISTICS:
        (A) LENGTH: 2041 base pairs
        (B) TYPE: nucleic acid (C) STRANDEDNESS: single
(D) TOPOLOGY: linear (ii) MOLECULE TYPE: cDNA (xi) SEQUENCE DESCRIPTION: SEQ ID NO:105:

| | | | | | |
|---|---|---|---|---|---|
| CGGCACGAGC | TCGTGCCGAT | CAGTGCCATT | GACGGCTTGT | ACGACCTTCT | GGGGATTGGA | 60 |
| ATACCCAACC | AAGGGGGTAT | CCTTTACTCC | TCACTAGAGT | ACTTCGAAAA | AGCCCTGGAG | 120 |
| GAGCTGGCAG | CAGCGTTTCC | GGGTGATGGC | TGGTTAGGTT | CGGCCGCGGA | CAAATACGCC | 180 |
| GGCAAAAACC | GCAACCACGT | GAATTTTTTC | CAGGAACTGG | CAGACCTCGA | TCGTCAGCTC | 240 |
| ATCAGCCTGA | TCCACGACCA | GGCCAACGCG | GTCCAGACGA | CCCGCGACAT | CCTGGAGGGC | 300 |
| GCCAAGAAAG | GTCTCGAGTT | CGTGCGCCCG | GTGGCTGTGG | ACCTGACCTA | CATCCCGGTC | 360 |
| GTCGGGCACG | CCCTATCGGC | CGCCTTCCAN | GCGCCGTTTT | GCGCGGGCGC | GATGGCCGTA | 420 |
| GTGGGCGGCG | CGCTTGCCTA | CTTGGTCGTG | AAAACGCTGA | TCAACGCGAC | TCAACTCCTC | 480 |
| AAATTGCTTG | CCAAATTGGC | GGAGTTGGTC | GCGGCCGCCA | TTGCGGACAT | CATTTCGGAT | 540 |
| GTGGCGGACA | TCATCAAGGG | CATCCTCGGA | GAAGTGTGGG | AGTTCATCAC | AAACGCGCTC | 600 |
| AACGGCCTGA | AGAGCTTTG | GACAAGCTC | ACGGGTGGG | TGACCGGACT | GTTCTCTCGA | 660 |
| GGGTGGTCGA | ACCTGGAGTC | CTTCTTTGCG | GGCGTCCCCG | GCTTGACCGG | CGCGACCAGC | 720 |
| GGCTTGTCGC | AAGTGACTGG | CTTGTTCGGT | GCGGCCGGTC | TGTCCGCATC | GTCGGGCTTG | 780 |
| GCTCACGCGG | ATAGCCTGGC | GAGCTCAGCC | AGCTTGCCCG | CCCTGGCCGG | CATTGGGGGC | 840 |
| GGGTCCGGTT | TTGGGGGCTT | GCCGAGCCTG | GCTCAGGTCC | ATGCCGCCTC | AACTCGGCAG | 900 |
| GCGCTACGGC | CCCGAGCTGA | TGGCCCGGTC | GGCGCCGCTG | CCGAGCAGGT | CGGCGGGCAG | 960 |
| TCGCAGCTGG | TCTCCGCGCA | GGGTTCCCAA | GGTATGGGCG | GACCCGTAGG | CATGGGCGGC | 1020 |
| ATGCACCCCT | CTTCGGGGGC | GTCGAAAGGG | ACGACGACGA | AGAAGTACTC | GGAAGGCGCG | 1080 |
| GCGGCGGGCA | CTGAAGACGC | CGAGCGCGCG | CCAGTCGAAG | CTGACGCGGG | CGGTGGGCAA | 1140 |
| AAGGTGCTGG | TACGAAACGT | CGTCTAACGG | CATGGCGAGC | CAAATCCATT | GCTAGCCAGC | 1200 |
| GCCTAACAAC | GCGCAATGCT | AAACGGAAGG | GACACGATCA | ATGACGGAAA | ACTTGACCGT | 1260 |
| CCAGCCCGAG | CGTCTCGGTG | TACTGGCGTC | GCACCATGAC | AACGCGGCGG | TCGATGCNTC | 1320 |
| CTCGGGCGTC | GAAGCTGCCG | CTGGCCTAGG | CGAATCTGTG | GCGATCACTC | ACGGTCCGTA | 1380 |
| CTGCTCACAG | TTCAACGACA | CGTTAAATGT | GTACTTGACT | GCCCACAATG | CCCTGGGCTC | 1440 |
| GTCCTTGCAT | ACGGCCGGTG | TCGATCTCGC | CAAAAGTCTT | CGAATTGCGG | CGAAGATATA | 1500 |
| TAGCGAGGCC | GACGAAGCGT | GGCGCAAGGC | TATCGACGGG | TTGTTTACCT | GACCACGTTT | 1560 |
| GCTGCCCGCA | GTGCAGGCCA | CGACGTAGCG | CAGGTCGTGT | CCCTCGTAGG | CGTGGATGCG | 1620 |
| ACCGGCCAGC | ACCAGCACCC | GGTGCGCACC | GATGGGCACG | GACAGTAGCT | CGCCCGCATG | 1680 |
| CCCGGCTGCG | GTTGGCGGCA | CAAACCCGGG | CAGTTCGGCC | TGCGGCAGCA | CGGTGGTNGG | 1740 |
| GGAGCCCAAC | GCCGCAACGG | CCGGTAACCA | TCCCGACCCG | AGCACGACCG | AGACGTCATG | 1800 |
| TTCGCCGATC | CCGGTGCGGT | CAGCGATGAC | CTGCGCCGCC | CGCGGGGCCA | GTTTGTCGGG | 1860 |
| ATCGGGCGC | GGGTCAGCCA | CACTGGGCGA | GCTTAACTGA | GCCGCTCGCC | GGGGAGCGGG | 1920 |
| TGCTNGTCGA | TGAGATACTG | CGAGCATGCC | AGCAGCCAGC | GCATCCGACC | GCGTCGAGGA | 1980 |
| ATTGGTGCGG | CGCCGTGGTG | GCGAGCTGGT | CGAGCTGTCC | CATGCCATCC | ACCTCGTGCC | 2040 |
| G | | | | | | 2041 |

(2) INFORMATION FOR SEQ ID NO:106:

(i) SEQUENCE CHARACTERISTICS:
        (A) LENGTH: 1202 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:106:

| | | | | | |
|---|---|---|---|---|---|
| GAGCTCACCG | CTATCAACCA | ATACTTTCTG | CACTCCAAGA | TGCAGGACAA | CTGGGGTTTT | 60 |
| ACCGAGCTGG | CGGCCCACAC | CCGCGCGGAG | TCGTTCGACG | AAATGCGGCA | CGCCGAGGAA | 120 |
| ATCACCGATC | GCATCTTGTT | GCTGGATGGT | TTGCCGAACT | ACCAGCGCAT | CGGTTCGTTG | 180 |
| CGTATCGGCC | AGACGCTCCG | CGAGCAATTT | GAGGCCGATC | TGGCGATCGA | ATACGACGTG | 240 |
| TTGAATCGTC | TCAAGCCAGG | AATCGTCATG | TGCCGGGAGA | AACAGGACAC | CACCAGCGCC | 300 |
| GTACTGCTGG | AGAAAATCGT | TGCCGACGAG | GAAGAACACA | TCGACTACTT | GGAAACGCAG | 360 |
| CTGGAGCTGA | TGGACAAGCT | AGGAGAGGAG | CTTTACTCGG | CGCAGTGCGT | CTCTCGCCCA | 420 |
| CCGACCTGAT | GCCCGCTTGA | GGATTCTCCG | ATACCACTCC | GGGCGCCGCT | GACAAGCTCT | 480 |
| AGCATCGACT | CGAACAGCGA | TGGGAGGGCG | GATATGGCGG | CCCCACAGC  | ACCGACCACT | 540 |
| GCCCCCACCG | CAATCCGAGC | CGGTGGCCCG | CTGCTCAGTC | CGGTGCGACG | CAACATTATT | 600 |
| TTCACCGCAC | TTGTGTTCGG | GGTGCTGGTC | GCTGCGACCG | GCCAAACCAT | CGTTGTGCCC | 660 |
| GCATTGCCGA | CGATCGTCGC | CGAGCTGGGC | AGCACCGTTG | ACCAGTCGTG | GGCGGTCACC | 720 |
| AGCTATCTGC | TGGGGGGAAC | ACTSKYGKKK | KTGKKGKSKS | KSRMRMKCTC | GGTGATCTGC | 780 |
| TCGGCCGCAA | CAGGGTGCTG | CTAGGCTCCG | TCGTGGTCTT | CGTCGTTGGC | TCTGTGCTGT | 840 |
| GCGGGTTATC | GCAGACGATG | ACCATGCTGG | CGATCTCTCG | CGCACTGCAG | GGCGTCGGTG | 900 |
| CCGGTGCGAT | TTCCGTCACC | GCCTACGCGC | TGGCCGCTGA | GGTGGTCCCA | CTGCGGGACC | 960 |
| GTGGCCGCTA | CCAGGGCGTC | TTANGTGCGG | TGTTCGGTGT | CAACACGGTC | ACCGGTCCGC | 1020 |
| TGCTGGGGGG | CTGGCTCACC | GACTATCTGA | GCTGGCGGTG | GGCGTTCCGA | CCACCAGCCC | 1080 |
| CATCACCGAC | CCGATCGCGG | TCATCGCGGC | GAACACCGCC | CTCGCGGCGT | TGCGGGCAGG | 1140 |
| TCCCTTGGGG | AACGTGGTCC | CACAGCGCCA | GAACGGTCGG | AAATGCGATG | GCCGACCCAC | 1200 |
| AC | | | | | | 1202 |

(2) INFORMATION FOR SEQ ID NO:107:

(i) SEQUENCE CHARACTERISTICS:
        (A) LENGTH: 496 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:107:

| | | | | | |
|---|---|---|---|---|---|
| GGCGGCGGCA | GTTGGCCAGC | AGTTNGGGCG | GGGGAGCCGG | TTCGGNGACC | AAGAAATCGG | 60 |
| CCTGGGCAAG | CAGCCGGGAC | CGCGNACCGT | GATCAGTTNG | GATCGCCGGG | ACCGCCGCCG | 120 |
| ACCAANGCCA | TTCCGCCGNT | GAGGAAGTCG | GAANTNTGCG | CAGTGATGAC | GCCCTGCTGC | 180 |
| AACGCNTCCC | GGATTGCCGA | GCGGATCGCC | GCCGAACGGC | GGTGCTCACC | ACCGGCGAGC | 240 |
| ACCCCTACNG | ACAGGCCCGC | ATAGCTGAAT | GACGCCGGGT | NACCGCCGTC | CCNTCCACCG | 300 |
| NGANATCGGC | CCGGANGCAA | AAGATCCGTC | GGCGCTCCGC | CTCGGCGACG | ACAGCCACGT | 360 |
| TCACCCGCGC | GTTATCGGTG | GCCGCGATCG | CATACCAGGC | GCCGTCAAGG | TNGCCGTYGC | 420 |

```
GGTAGTCACG CACCGACAAG GTGATYTGGT CCATCGCCTN GACGGCGGGG GTGACGCTGG    480

GGGCGATCAM GTGCAC                                                    496
```

(2) INFORMATION FOR SEQ ID NO:108:

(i) SEQUENCE CHARACTERISTICS:
        (A) LENGTH: 849 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:108:

```
TGGATTCCGA TAGCGGTTTC GGCCCCTCGA CGGGCGACCA CGGCGCGCAG GCCTCCGAAC     60

GGGGGGCCGG GACGCTGGGA TTCGCCGGGA CCGCAACCAA AGAACGCCGG GTCCGGGCGG    120

TCGGGCTGAC CGCACTGGCC GGTGATGAGT TCGGCAACGG CCCCCGGATG CCGATGGTGC    180

CGGGGACCTG GGAGCAGGGC AGCAACGAGC CCGAGGCGCC CGACGGATCG GGAGAGGGG     240

GAGGCGACGG CTTACCGCAC GACAGCAAGT AACCGAATTC CGAATCACGT GGACCCGTAC    300

GGGTCGAAAG GAGAGATGTT ATGAGCCTTT TGGATGCTCA TATCCCACAG TTGGTGGCCT    360

CCCAGTCGGC GTTTGCCGCC AAGGCGGGGC TGATGCGGCA CACGATCGGT CAGGCCGAGC    420

AGGCGGCGAT GTCGGCTCAG GCGTTTCACC AGGGGGAGTC GTCGGCGGCG TTTCAGGCCG    480

CCCATGCCCG GTTTGTGGCG GCGGCCGCCA AGTCAACAC CTTGTTGGAT GTCGCGCAGG    540

CGAATCTGGG TGAGGCCGCC GGTACCTATG TGGCCGCCGA TGCTGCGGCC GCGTCGACCT    600

ATACCGGGTT CTGATCGAAC CCTGCTGACC GAGAGGACTT GTGATGTCGC AAATCATGTA    660

CAACTACCCC GCGATGTTGG GTCACGCCGG GGATATGGCC GGATATGCCG GCACGCTGCA    720

GAGCTTGGGT GCCGAGATCG CCGTGGAGCA GGCCGCGTTG CAGAGTGCGT GGCAGGGCGA    780

TACCGGGATC ACGTATCAGG CGTGGCAGGC ACANTGGTAA CCANGCCANG GAAGATTTGG    840

TGCGGGCCT                                                            849
```

(2) INFORMATION FOR SEQ ID NO:109:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:109:

```
Met Ser Leu Leu Asp Ala His Ile Pro Gln Leu Val Ala Ser Gln Ser
 1               5                  10                  15

Ala Phe Ala Ala Lys Ala Gly Leu Met Arg His Thr Ile Gly Gln Ala
            20                  25                  30

Glu Gln Ala Ala Met Ser Ala Gln Ala Phe His Gln Gly Glu Ser Ser
        35                  40                  45

Ala Ala Phe Gln Ala Ala His Ala Arg Phe Val Ala Ala Ala Lys
    50                  55                  60

Val Asn Thr Leu Leu Asp Val Ala Gln Ala Asn Leu Gly Glu Ala Ala
65                  70                  75                  80

Gly Thr Tyr Val Ala Ala Asp Ala Ala Ala Ser Thr Tyr Thr Gly
                85                  90                  95
```

Phe (2) INFORMATION FOR SEQ ID NO:110:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:110:

```
Met Ser Leu Leu Asp Ala His Ile Pro Gln Leu Val Ala Ser Gln
 1               5                  10                  15
```

(2) INFORMATION FOR SEQ ID NO:111:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:111:

```
Ala His Ile Pro Gln Leu Val Ala Ser Gln Ser Ala Phe Ala Ala
 1               5                  10                  15
```

(2) INFORMATION FOR SEQ ID NO:112:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:112:

```
Leu Val Ala Ser Gln Ser Ala Phe Ala Ala Lys Ala Gly Leu Met
 1               5                  10                  15
```

(2) INFORMATION FOR SEQ ID NO:113:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:113:

```
Ser Ala Phe Ala Ala Lys Ala Gly Leu Met Arg His Thr Ile Gly
 1               5                  10                  15
```

(2) INFORMATION FOR SEQ ID NO:114:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:114:

```
Lys Ala Gly Leu Met Arg His Thr Ile Gly Gln Ala Glu Gln Ala
1               5                   10                  15
```

(2) INFORMATION FOR SEQ ID NO:115:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:115:

```
Arg His Thr Ile Gly Gln Ala Glu Gln Ala Ala Met Ser Ala Gln
1               5                   10                  15
```

(2) INFORMATION FOR SEQ ID NO:116:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:116:

```
Gln Ala Glu Gln Ala Ala Met Ser Ala Gln Ala Phe His Gln Gly
1               5                   10                  15
```

(2) INFORMATION FOR SEQ ID NO:117:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:117:

```
Ala Met Ser Ala Gln Ala Phe His Gln Gly Glu Ser Ser Ala Ala
1               5                   10                  15
```

(2) INFORMATION FOR SEQ ID NO:118:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:118:

```
Ala Phe His Gln Gly Glu Ser Ser Ala Ala Phe Gln Ala Ala His
1               5                   10                  15
```

(2) INFORMATION FOR SEQ ID NO:119:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:119:

```
Glu Ser Ser Ala Ala Phe Gln Ala Ala His Ala Arg Phe Val Ala
1               5                   10                  15
```

(2) INFORMATION FOR SEQ ID NO:120:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:120:

```
Phe Gln Ala Ala His Ala Arg Phe Val Ala Ala Ala Ala Lys Val
1               5                   10                  15
```

(2) INFORMATION FOR SEQ ID NO:121:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:121:

```
Ala Arg Phe Val Ala Ala Ala Ala Lys Val Asn Thr Leu Leu Asp
1               5                   10                  15
```

(2) INFORMATION FOR SEQ ID NO:122:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:122:

```
Ala Ala Ala Lys Val Asn Thr Leu Leu Asp Val Ala Gln Ala Asn
1               5                   10                  15
```

(2) INFORMATION FOR SEQ ID NO:123:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:123:

```
Asn Thr Leu Leu Asp Val Ala Gln Ala Asn Leu Gly Glu Ala Ala
1               5                   10                  15
```

(2) INFORMATION FOR SEQ ID NO:124:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:124:

Val Ala Gln Ala Asn Leu Gly Glu Ala Ala Gly Thr Tyr Val Ala Ala
1               5                   10                  15

Asp Ala (2) INFORMATION FOR SEQ ID NO:125:

(i) SEQUENCE CHARACTERISTICS:
        (A) LENGTH: 1752 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:125:

```
CGGCACGAGA ATGTCGCCTG TGCCTCGATA GCCACTTGCG TGTGGTCGCG CTGCCAGCGG      60
GTCAGCCAGG TCGCCTGGTC CAGGCCATCG GGCCGGCGCA GGAGCGCGAT GTTGGCCAGA     120
CCCGGTGTAC GAGAACCGGA CTCGACNAAG TGTCGGCGCT GACGGCGGCT CAGTTCGCGG     180
CACACGCCCA GATCTATCAG GCCGTCAGCG CCCAGGCCGC GGCGATTCAC GAGATGTTCG     240
TCAACACTCT ACAGATNANC TCAGGGTCGT ATGCTGCTAC CGAGGCCGCC AACGCGGCCG     300
CGGCCGGCTA GAGGAGTCAC TGCGATGGAT TTTGGGGCGT TGCCGCCGGA GGTCAATTCG     360
GTGCGGATGT ATGCCGGTCC TGGCTCGGCA CCAATGGTCG CTGCGGCGTC GGCCTGGAAC     420
GGGTTGGCCG CGGAGCTGAG TTCGGCGGCC ACCGGTTATG AGACGGTGAT CACTCAGCTC     480
AGCAGTGAGG GGTGGCTAGG TCCGCGTCA GCGGCGATGG CCGAGGCAGT TGCGCCGTAT      540
GTGGCGTGGA TGAGTGCCGC TGCGGCGCAA GCCGAGCAGG CGGCCACACA GGCCAGGGCC     600
GCCGCGGCCG CTTTTGAGGC GGCGTTTGCC GCGACGGTGC CTCCGCCGTT GATCGCGGCC     660
AACCGGGCTT CGTTGATGCA GCTGATCTCG ACGAATGTCT TTGGTCAGAA CACCTCGGCG     720
ATCGCGGCCG CCGAAGCTCA GTACGGCGAG ATGTGGGCCC AAGACTCCGC GGCGATGTAT     780
GCCTACGCGG GCAGTTCGGC GAGCGCCTCG GCGGTCACGC CGTTTAGCAC GCCGCCGCAG     840
ATTGCCAACC CGACCGCTCA GGGTACGCAG GCCGCGGCCG TGGCCACCGC CGCCGGTACC     900
GCCCAGTCGA CGCTGACGGA GATGATCACC GGGCTACCCA ACGCGCTGCA AAGCCTCACC     960
TCACNTCTGT TGCAGTCGTC TAACGGTCCG CTGTCGTGGC TGTGGCAGAT CTTGTTCGGC    1020
ACGCCCAATT TCCCCACCTC AATTTCGGCA CTGCTGACCG ACCTGCAGCC CTACGCGAGC    1080
TTNTTNTATA ACACCGAGGG CCTGCCGTAC TTCAGCATCG GCATGGGCAA CAACTTCATT    1140
CAGTCGGCCA AGACCCTGGG ATTGATCGGC TAGGCGGCAC CGGCTGCGGT CGCGGCTGCT    1200
GGGGATGCCG CCAAGGGCTT GCCTGGACTG GGCGGGATGC TCGGTGGCGG GCCGGTGGCG    1260
GCGGGTCTGG GCAATGCGGC TTCGGTTGGC AAGCTGTCGG TGCCGCCGGT GTGGANTGGA    1320
CCGTTGCCCG GGTCGGTGAC TCCGGGGGCT GCTCCGCTAC CGGTGAGTAC GGTCAGTGCC    1380
GCCCCGGAGG CGGCGCCCGG AAGCCTGTTG GGCGGCCTGC CGCTANCTGG TGCGGGCGGG    1440
GCCGGCGCGG GTCCACGCTA CGGATTCCRT CCCACCGTCA TGGCTCGCCC ACCCTTCGMC    1500
GGGATAGTCG CTGCCGCAAC GTATTAACGC GCCGGCCTCG GCTGGTGTGG TCCGCTGCGG    1560
GTGGCAATTG GTCNGCGCCG AAATCTCSGT GGGTTATTTR CGGTGGGATT TTTTCCCGAA    1620
GCCGGGTTCA RCACCGGATT TCCTAACGGT CCCGCKACTC TCGTGCCGAA TTCSGCACTA    1680
AGTGACGTCC GGCGGAAACC CGTTGGGTNT GAAAGCTTCA GAAAGGCCCG CTCCCAGGGG    1740
TTCGGCAAAC GG                                                       1752
```

(2) INFORMATION FOR SEQ ID NO:126:

(i) SEQUENCE CHARACTERISTICS:
        (A) LENGTH: 400 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:126:

```
Met Asp Phe Gly Ala Leu Pro Pro Glu Val Asn Ser Val Arg Met Tyr
  1               5                  10                  15

Ala Gly Pro Gly Ser Ala Pro Met Val Ala Ala Ser Ala Trp Asn
             20                  25                  30

Gly Leu Ala Ala Glu Leu Ser Ser Ala Ala Thr Gly Tyr Glu Thr Val
             35                  40                  45

Ile Thr Gln Leu Ser Ser Glu Gly Trp Leu Gly Pro Ala Ser Ala Ala
 50                  55                  60

Met Ala Glu Ala Val Ala Pro Tyr Val Ala Trp Met Ser Ala Ala Ala
 65                  70                  75                  80

Ala Gln Ala Glu Gln Ala Ala Thr Gln Ala Arg Ala Ala Ala Ala Ala
             85                  90                  95

Phe Glu Ala Ala Phe Ala Ala Thr Val Pro Pro Leu Ile Ala Ala
            100                 105                 110

Asn Arg Ala Ser Leu Met Gln Leu Ile Ser Thr Asn Val Phe Gly Gln
            115                 120                 125

Asn Thr Ser Ala Ile Ala Ala Glu Ala Gln Tyr Gly Glu Met Trp
            130                 135                 140

Ala Gln Asp Ser Ala Ala Met Tyr Ala Tyr Ala Gly Ser Ser Ala Ser
145                 150                 155                 160

Ala Ser Ala Val Thr Pro Phe Ser Thr Pro Pro Gln Ile Ala Asn Pro
                165                 170                 175

Thr Ala Gln Gly Thr Gln Ala Ala Val Ala Thr Ala Ala Gly Thr
            180                 185                 190

Ala Gln Ser Thr Leu Thr Glu Met Ile Thr Gly Leu Pro Asn Ala Leu
            195                 200                 205

Gln Ser Leu Thr Ser Xaa Leu Leu Gln Ser Ser Asn Gly Pro Leu Ser
            210                 215                 220

Trp Leu Trp Gln Ile Leu Phe Gly Thr Pro Asn Phe Pro Thr Ser Ile
225                 230                 235                 240

Ser Ala Leu Leu Thr Asp Leu Gln Pro Tyr Ala Ser Xaa Xaa Tyr Asn
                245                 250                 255

Thr Glu Gly Leu Pro Tyr Phe Ser Ile Gly Met Gly Asn Asn Phe Ile
            260                 265                 270

Gln Ser Ala Lys Thr Leu Gly Leu Ile Gly Ser Ala Ala Pro Ala Ala
            275                 280                 285

Val Ala Ala Gly Asp Ala Lys Gly Leu Pro Gly Leu Gly
            290                 295                 300

Met Leu Gly Gly Gly Pro Val Ala Ala Gly Leu Gly Asn Ala Ala Ser
305                 310                 315                 320

Val Gly Lys Leu Ser Val Pro Pro Val Trp Xaa Gly Pro Leu Pro Gly
                325                 330                 335

Ser Val Thr Pro Gly Ala Ala Pro Leu Pro Val Ser Thr Val Ser Ala
            340                 345                 350
```

```
Ala Pro Glu Ala Ala Pro Gly Ser Leu Leu Gly Leu Pro Leu Xaa
        355                 360                 365

Gly Ala Gly Gly Ala Gly Ala Gly Pro Arg Tyr Gly Phe Xaa Pro Thr
    370                 375                 380

Val Met Ala Arg Pro Pro Phe Xaa Gly Ile Val Ala Ala Ala Thr Tyr
385                 390                 395                 400

(2) INFORMATION FOR SEQ ID NO:127:

(i) SEQUENCE CHARACTERISTICS:
        (A) LENGTH: 474 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:127:

GGCACGAGCA CCAGTTGACC CGCGAAGAAC CTGACCGCGC CACCCAGCGC CGCCCGCATC      60

ACCGGCCCCG TCCCACGAAC CTTTTCGGTA AACGAGCCAC TCCAGCGGAG ATCGGTACCG     120

CCCGACGCAT TTGGTGTAAG GACCACCTCG CCGAAGTAGT CCTGGACGGG TGTCCTCGCG     180

CCAACCAGCT TGTAGACGTG GCGACGGTCC TGCTCATACT CGACGGTCTC TTCCTGCACG     240

AACACCGGCC ACATGCCTAG TTTGCGGATG GCCCCGATGC CGCCGGGCGC GGGATCACCG     300

CGTCGCGCCC AACTCGATTG AGCAACGATG GGCTTGGCCC AGGTCGCCCA GTTGCCACCG     360

TCTGTCACGA GCCGAAACAA GGTTGCAGCC GGCGCGCTGC TGGTCTTGGT GACCTCGAAC     420

GAAAATTTCC GACCCGACAT GCGCGACTCC CGAAACGACA ACTGAAGCTC GTGC           474

(2) INFORMATION FOR SEQ ID NO:128:

(i) SEQUENCE CHARACTERISTICS:
        (A) LENGTH: 1431 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:128:

CTGCGCGCCG GAAAAAANTA TTACTGGCAG GACCGGCAGA ATGCATGGTG ATATTCCGGT      60

GATGAGGCCG CCGAGGAACC GACTAGTGCG AGGGTCAACA CATCGGTTAT TCGTTGCCGT     120

TTAGGTCTTG GATCTGCCGG GACGGCAACG AGTTGGCAGG ACCGCTCACG CGAGCGCTGT     180

TGACAGAGTC GGTTCACGTC GAACTCGCCA CCCGTCAGAT GCGAATGATA GCCACATCGG     240

CCACACCATC GACGGCGTCG AAGTCGCCGT CGTGGGTCAC GACCGGCACC CCTTGCGACG     300

TGGCAACGGC AGCGGCCCTC ACCGGACGGG ACCGAGATCG TCGGTGGTGT CGCCAGTGAG     360

CGTTGCGAGG TCGCGGGTGC AATCCCGCAT CTGCTTGCGT ATGCCGAAGC CGCCGCAGCA     420

GCTCGTCTCG ACTCAACCAT CGGCGCCGTG CGGGCTGCCT GCGGTCAGCA GCGCAACGGG     480

TTTGCCGTTG GCAGTGATGG TGATGTCTTC GCCGGCCTGC ACGCGCCGTA GCAGCCCGGC     540

GGTGTTGTTG CGCAGTTCGC GAGACGCGAC TTCAGCAGGC ATGCTGCGGG GATCGGCTTG     600

CGCTGGGCGC GGTGTCACCG TCATGCGCTT GGGATATCAC GTGATCTATC GGCACGAAGC     660

CGCCGGATGA GCGAGGCAAA CCGCCTACAC GGGCTGCCTC GCCTTGACCG CGCCGAACGT     720

TACTGTGCCG GGGGCATCAG CACCGTATCG ATCATGTACA CCGTCGCGTG GCGGTGTGA     780

CTCCGCCACA TACCAAACGG GCGTTGTTGA CCATGAGTCG TCGCGGGCGC CTATCACCGT     840
```

```
CAGGTCGGCA CCTTGCAGGT CTGATGGGTG CCGTCGATCC TGCTCGGACT CGCCTGGCCG      900

GCTATCACGT GGTAGGTCAG GATGCTGCTG AGCAGCTTGG CGTCAGTCTT GAGTTGATCG      960

ATAGTGGCCG CCGGCAGCTT GTCGAATGCG GCGTTGGTGG GGGCGAAAAC GGTGTACTCG     1020

CCGCCGTTGA GGGTGTCGAC CAGATTCACA TCCGGGTTCA GCTTGCCCGA CAGAGCCGAG     1080

GTCAGGGTAC TGAGCATCGG GTTGTTGGAA GCCGCGGTAG CGACCGGGTC TTGCGCCATT     1140

CCGGCCACCG ATCCGGGACC GGTGGGATTT TGCGCCGCGT ATTGCGCGCA CCCACGACCA     1200

ATCAGGTCCG CTGCGGTCAG CCATTGCCGC CGTGGTAACG GCGCCGCCG  GGCTGGTCGC     1260

CGGTTTCGGG CTGGTGTCTT GCGACACGGG TTTGGTGCTC GAACAACCCG CTAAGAACGC     1320

AATCGCGATG GCTGCGAGGC TCGCTGCTGC GGCCGGTTTG GCCTGAACGT TGATCATCGC     1380

TTCGATTCCT TTGCTTCTGC GGCGGCGTTG AACGCCGTCC TCCTGGGTGG A              1431

(2) INFORMATION FOR SEQ ID NO:129:

(i) SEQUENCE CHARACTERISTICS:
        (A) LENGTH: 279 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:129:

GCACGAGAGT CGTATCTTTG CACCCAGCGC CCGTAGGAAA CCGCTGGCCT GGCTAACTCA       60

GATGCGGGCG GCCGTCGATT CGAGAGGTAA CCGATCGCCC GCCGACAATG GGTTACCCAC      120

CGAGACTGAT TGCCGCGCAG CCGCCTTCGA CGTGTAAGCG CCGGTTCGTG CATGCCCGGA      180

ACGGCTGCAC TCACGGACCT TCTACGTAGT ACGTGACGGA CTTTTACGCA TTATCGCTGA      240

CGATCTTTGC CTCCCAGGAC TCCAGAATCT ACTCGTGCC                            279

(2) INFORMATION FOR SEQ ID NO:130:

(i) SEQUENCE CHARACTERISTICS:
        (A) LENGTH: 1470 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:130:

ACCGCCACCC GCAGCCCGGA ATCACCGTCG GTAACCTGCG AATACAATTT CTTCATCGAC       60

GACTTCGCGA ACAGCGAACC CGAGCCCACC GCCTGATAGC CTTCTTCCTC GATGTTCCAA      120

CCGCCGGCGG CGTCGAACGA AACGATACGA CCCGCGCTCT GCGGGTCAGA CGCATGAATG      180

TCGTAGCCCG CCAGCAACGG CAACGCCAGC AGACCCTGCA TCGCGGCCGC CAGATTGCCA      240

CGCACCATAA TCGCCAGCCG GTTGATTTTG CCGGCAAACG TCAGCGGCAC ACCCTCGAGC      300

TTCTCGTAGT GCTCAAGTTC CACGGCATAC AGCCGGGCAA ACTCAACCGC GACCGCAGCC      360

GTGCCAGCGA TGCCGGTAGC GGTGTAGTCA TCGGTGATAT ACACCTTGCG CACATCACGC      420

CCAGAAATCA TGTTGCCCTG CGTCGAACGC CGGTCACCCG CCATGACAAC ACCGCCGGGG      480

TATTTCAGCG CGACAATGGT GGTGCCGTGC GGCAGTTGCG CATCGCCGCC TGCGAGTGGC      540

GCACCGCCGC TGATGCTTGC CGGCAGCAAC TCCGGCGCCT GGCGGCGCAG GAAGTCAAGT      600

GAAAGAAGAT AGGTCTACAG CGGGTGTTCC AGAGAGTGAA TTAATGGACA GGCGATCGGG      660
```

-continued

```
CAACGGCCAG GTCACTGTCC GCCCTTTTGG ACGTATGCGC GGACGAAGTC CTCGGCGTTC      720

TCCTCGAGGA CGTCGTCGAT TTCGTCGAGC AGATCGTCGG TCTCCTCGGT CAGCTTTTCG      780

CGACGCTCCT GGCCCGCGGC GGTGCTGCCG GCGATGTCGT CATCATCGCC GCCGCCACCG      840

CCACGCTTGG TCTGCTCTTG CGCCATCGCC GCCTCCTGCT TCCTCATGGC CTTTCAAAAG      900

GCCGCGGGTG CGCGTCACAC GCCCGCTGTC TTTCTCTCAC CTACCGGTCA ACACCAACGT      960

TTCCCGGCCT AACCAGGCTT AGCGAGGCTC AGCGGTCAGT TGCTCTACCA GCTCCACGGC     1020

ACTGTCCACC GAATCCAGCA ACGCACCAAC ATGCGCCTTA CTACCCCGCA ACGGCTCCAG     1080

CGTCGGGATG CGAACCAGCG AGTCGCCGCC AGGTCGAAGA TCACCGAGTC CCAGCTAGCC     1140

GCGGCGATAT CAGCCCCGAA CCGGCGCAGG CATTTCGCCG CGGAAATACG CGCGGGTGTC     1200

GGTCGGCGGT TCTCCACCGC ACTCAGCACC TGGTGTTTCG GTGACTAAAC GCTTTATCGA     1260

GCCGCGCGCG ACCAGCCGGT TGTACAGGCC CTTGTCCAGC CGGACATCGG AGTACTGCAG     1320

GTTGACGAGG TGCAGCCGGG GCGCCGACCA GCTCAGGTTC TCCCGCTGCC GGAAACCGTC     1380

GAGCAGCCGC AGTTTGGCCG GCCAGTCCAG CAGCTCCGCG CAATCCATCG GGTCACGCTC     1440

GAGCTGATCC AGCACGTGTG CCCAGGTTTC                                     1470

(2) INFORMATION FOR SEQ ID NO:131:

(i) SEQUENCE CHARACTERISTICS:
        (A) LENGTH: 1059 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:131:

ATTCCCATCG CTCCGGCACC TATCACCAGG TAGTCGGTTT CGATGGTTTT CGCCGGCCCT       60

TGCGTTGGCC TGGGCCACGG GTCGTTCATG GGCCCTCCTG TGCGGATTGG AATTTGTGAC      120

AACGAAATCG GGCGATCGGT GAGCAATCGT CGCCGATGCA AGACACGCTT TCGCTGCCGC      180

GGCGTCAGGT GGAGTTTAGG CCAGCGTAAC AACGTAGACC GGCCACTGAC CAAACCCCAA      240

ACCCACAAAC CCTGGACGCA TGCGGGTCTC GGGCGTCAAA TTCCGGGTAG ATATCGTATA      300

CCGATATCGG ATGCCGTAGC CTTATCGAGG CATGAGACGC CCGCTAGACC CACGCGATAT      360

TCCAGATGAG CTGCGGCGAC GGCTGGGGCT CTTGGATGCG GTGGTGATCG GGCTTGGGTC      420

CATGATCGGT GCCGGAATCT TTGCTCGTGC CGAATTCGGC ACGAGCTCGT GCCGAATTCG      480

GCACGAGATT CCAATCCCCA GAAGGTCGTA CAAGCCGTCA ATGGCACTTG ATCGTTGGAT      540

CGATGATGAA CGCTCTGCTC ATGCCTGCCG CCTATCTCAA CGGTCGTCGA TTCCATGCAT      600

TAGCCTTGGT TCTGCATTGC ACGCGTAGGG CCTACAGTCT GGCTGTCATG CTTGGCCGAT      660

GTCAACAGTT TTTTTCATGC TAAGCAGATC GTCAGTTTTG AGTTCGTGAA GACGGCATGT      720

TCACTTGTTG TCGACTACAT CGTCTGCGCA CATTTGCCCT CCTGCAACTG CGCTGCGACA      780

ATGCGCCAAC CGCCGTGTAG CTCGTGCCGA ATTCGGCACG AGGATCCACC GGAGATGGCC      840

GACGACTACG ACGAGGCCTG GATGCTCAAC ACCGTGTTCG ACTATCACAA CGAGAACGCA      900

AAAGAAGAGG TCATCCATCT CGTGCCCGAC GTGAACAAGG AGAGGGGCC CATCGAACTC      960

GTAACCAAGG TAGACAAAGA GGGACATCAG ACTCGTCTAC GATGGGAGC CACGTTTTCA     1020

TACAAGGAAC ATCCTAAGTT TTGATTCGGG AACATCCTA                           1059

(2) INFORMATION FOR SEQ ID NO:132:
```

(i) SEQUENCE CHARACTERISTICS:
    (A) LENGTH: 153 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:132:

```
GCACGAGGCA TTGGCGGGCA TCTGCATAAA CGGTGACGTA TCAGCACAAA ACAGCGGAGA      60
GAACAACATG CGATCAGAAC GTCTCCGGTG GCTGGTAGCC GCAGAAGGTC CGTTCGCCTC     120
GGTGTATTTC GACGACTCGC ACGACTCGTG CCG                                  153
```

(2) INFORMATION FOR SEQ ID NO:133:

(i) SEQUENCE CHARACTERISTICS:
        (A) LENGTH: 387 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:133:

```
CCGCGCGGTC GATCAGCGAG CCAGGCAAAA ACTCCGTCGA GCCCGAGTCG ATGATGGTCA      60
CCCGGCGCAG CATCTGGCGA ACGATCACCT CGATGTGCTT GTCGTGGATC GACACACCTT     120
GGGCGCGGTA GACCTCCTGG ACCTCGCGAA CCAGGTGTAT CTGCACCTCG CGGGGGCCCT     180
GCACCCGCAG CACCTCATGC GGGTCGGCCG AGCCTTCCAT CAGCTGCTGG CCCACCTCGA     240
CGTGGTCGCC ATCGGAGAGC ACCCGTTCGG AACCGTCTTC GTGCTTGAAC ACCCGCAGCC     300
GCTGCCGCTT GGAGATCTTG TCGTAGACCA CTTCCTCACC GCCGTCGTCA GGAACGATGG     360
TGATCTTGTA GAACCGCTCG CCGTCCT                                        387
```

(2) INFORMATION FOR SEQ ID NO:134:

(i) SEQUENCE CHARACTERISTICS:
        (A) LENGTH: 389 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:134:

```
GTTCAGCACG GCTATCCGAT TGTGCCGTTC GCTTCGGTGG GTGCTGAACA CGGCATCGAC      60
ATCGTGCTCG ACAACGAATC CCCACTGCTG GCACCGGTCC AGTTCCTCGC CGAGAAGCTG     120
CTCGGCACCA AGACGGTCC GGCGCTGGTC CGTGGTGTCG GACTGACACC GGTACCGCGC      180
CCCGAACGGC AGTATTACTG GTTCGGCGAG CCAACCGACA CCACAGAGTT TATGGGGCAG     240
CAAGCCGACG ATAACGCCGC ACGCAGGGTG CGCGAGCGTG CCGCCGCCGC TATCGAACAC     300
GGCATCGAGC TGATGCTGGC CGAGCGCGCA GCCGATCCAA ATCGATCCCT GGTCGGACGG     360
CTCTTGCGCT CGGACGCCTA AGGCGCCCC                                      389
```

(2) INFORMATION FOR SEQ ID NO:135:

(i) SEQUENCE CHARACTERISTICS:
        (A) LENGTH: 480 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:135:

| | | | | | |
|---|---|---|---|---|---|
| CCCGCGGTCG | GAATGATCCC | CGTCTCGTCG | CGCGCCCATT | TGATGCTGTT | GATGAGCTGT | 60 |
| TTGGAGAAGC | CCGGTTGGCG | TACCGGTGAG | CCGGAATATC | TGTTGGAAGC | GTCACCGGAT | 120 |
| GTNCACATGA | ANTNCNTTGN | CCCNGTNGCG | GTNTTGGNTG | NGGNAAACAC | GTGTTGTNTA | 180 |
| AGCCTTGNTG | GNCTCGNAAG | NGCCGTNGAC | GCCTGTGTCG | CCGAAGATAA | TGAGCACCTG | 240 |
| ACGGTTGGCG | GGATCGCCGT | TATCCCAAGG | AATTCCGAGG | TCGGTCCCGG | AGATGCCGAA | 300 |
| GCGTTCCAGG | GTCTTGTTGG | GGCTGTCCGG | TCCGGTCACC | CACTCGGCGA | GGGATGTGGN | 360 |
| AGCCCCGGCG | AGCGTGGCAC | CAGGATCCGG | CGCCGCCGCC | GGAGCAGGGT | CGGNNGCTGN | 420 |
| NCTGNNTTCC | TNNNGCCNAA | TTNNACTCCN | NCNACAANCT | TGNNNCCGAC | TCNNACCCGN | 480 |

(2) INFORMATION FOR SEQ ID NO:136:

(i) SEQUENCE CHARACTERISTICS:
        (A) LENGTH: 587 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:136:

| | | | | | |
|---|---|---|---|---|---|
| GCACGAGGCT | ACCGGCGCGT | CGCCCGCCAT | GCCCTGGATG | CACGCGTAGC | CACCCGTNCA | 60 |
| TNCAGCGGGT | CAGCCGCCGC | GTCCGGGCTT | AACGCTATAG | CAGCTGCAAA | CAACCCAGCG | 120 |
| CCGGCAATTA | CTTTGATGTT | GAACCGATGA | CCATNGCCTN | CGNGTNCAAT | CTCNTCTCTT | 180 |
| NGCGCGCCNC | TATTTNNGCC | ATANATTTGG | TTNNANNCGN | AACGCTAGAC | GTATCGAGTT | 240 |
| CCTTTTCGAC | CACCGGCTCA | ATTGTCAGCA | TCCTATGGGG | AACATGAGCC | CCGCCGCACC | 300 |
| GGGCCGTTTC | CAAATGGTGA | CGTCACAACG | GTGTCACAAG | CCAGCGCAAT | GTCCGCGGTA | 360 |
| GGGACGCGGC | GGCTGGGATC | GGTGGGGTGA | GCGCCCGGCT | TCTCAAAGCG | AGGGGAGCCC | 420 |
| CGGGACTCTT | ACCGGCCGAA | GGCGGCGGGT | GTCACTGATC | TAGGCTGACG | GCCAGTGGTT | 480 |
| GNTNAGCCAA | CAAGGATGAC | NACAAATAAN | CCGAGGANAG | ACANGNGACG | GNCCGANANG | 540 |
| CTNANCCGGN | NTTGNNCNAA | NNNNACNCAC | TTNTACCGNN | CTTATGN | | 587 |

(2) INFORMATION FOR SEQ ID NO:137:

(i) SEQUENCE CHARACTERISTICS:
        (A) LENGTH: 1200 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:137:

| | | | | | |
|---|---|---|---|---|---|
| CAGGCATGAG | CAGAGCGTTC | ATCATCGATC | CAACGATCAG | TGCCATTGAC | GGCTTGTACG | 60 |
| ACCTTCTGGG | GATTGGAATA | CCCAACCAAG | GGGGTATCCT | TTACTCCTCA | CTAGAGTACT | 120 |
| TCGAAAAAGC | CCTGGAGGAG | CTGGCAGCAG | CGTTTCCGGG | TGATGGCTGG | TTAGGTTCGG | 180 |
| CCGCGGACAA | ATACGCCGGC | AAAAACCGCA | ACCACGTGAA | TTTTTTCCAG | GAACTGGCAG | 240 |
| ACCTCGATCG | TCAGCTCATC | AGCCTGATCC | ACGACCAGGC | CAACGCGGTC | CAGACGACCC | 300 |
| GCGACATCCT | GGAGGGCGCC | AAGAAAGGTC | TCGAGTTCGT | GCGCCCGGTG | GCTGTGGACC | 360 |

```
TGACCTACAT CCCGGTCGTC GGGCACGCCC TATCGGCCGC CTTCCAGGCG CCGTTTTGCG      420

CGGGCGCGAT GGCCGTAGTG GGCGGCGCGC TTGCCTACTT GGTCGTGAAA ACGCTGATCA      480

ACGCGACTCA ACTCCTCAAA TTGCTTGCCA AATTGGCGGA GTTGGTCGCG GCCGCCATTG      540

CGGACATCAT TTCGGATGTG GCGGACATCA TCAAGGGCAC CCTCGGAGAA GTGTGGGAGT      600

TCATCACAAA CGCGCTCAAC GGCCTGAAAG AGCTTTGGGA CAAGCTCACG GGGTGGGTGA      660

CCGGACTGTT CTCTCGAGGG TGGTCGAACC TGGAGTCCTT CTTTGCGGGC GTCCCCGGCT      720

TGACCGGCGC GACCAGCGGC TTGTCGCAAG TGACTGGCTT GTTCGGTGCG GCCGGTCTGT      780

CCGCATCGTC GGGCTTGGCT CACGCGGATA GCCTGGCGAG CTCAGCCAGC TTGCCCGCCC      840

TGGCCGGCAT TGGGGGCGGG TCCGGTTTTG GGGGCTTGCC GAGCCTGGCT CAGGTCCATG      900

CCGCCTCAAC TCGGCAGGCG CTACGGCCCC GAGCTGATGG CCCGGTCGGC GCCGCTGCCG      960

AGCAGGTCGG CGGGCAGTCG CAGCTGGTCT CCGCGCAGGG TTCCCAAGGT ATGGGCGGAC     1020

CCGTAGGCAT GGGCGGCATG CACCCCTCTT CGGGGGCGTC GAAAGGGACG ACGACGAAGA     1080

AGTACTCGGA AGGCGCGGCG GCGGGCACTG AAGACGCCGA GCGCGCGCCA GTCGAAGCTG     1140

ACGCGGGCGG TGGGCAAAAG GTGCTGGTAC GAAACGTCGT CTAACGGCAT GGCGAGCCAA     1200
```

(2) INFORMATION FOR SEQ ID NO:138:

(i) SEQUENCE CHARACTERISTICS:
        (A) LENGTH: 392 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:138:

```
Met Ser Arg Ala Phe Ile Ile Asp Pro Thr Ile Ser Ala Ile Asp Gly
 1               5                  10                  15

Leu Tyr Asp Leu Leu Gly Ile Gly Ile Pro Asn Gln Gly Gly Ile Leu
             20                  25                  30

Tyr Ser Ser Leu Glu Tyr Phe Glu Lys Ala Leu Glu Glu Leu Ala Ala
         35                  40                  45

Ala Phe Pro Gly Asp Gly Trp Leu Gly Ser Ala Ala Asp Lys Tyr Ala
     50                  55                  60

Gly Lys Asn Arg Asn His Val Asn Phe Phe Gln Glu Leu Ala Asp Leu
65                  70                  75                  80

Asp Arg Gln Leu Ile Ser Leu Ile His Asp Gln Ala Asn Ala Val Gln
                 85                  90                  95

Thr Thr Arg Asp Ile Leu Glu Gly Ala Lys Lys Gly Leu Glu Phe Val
            100                 105                 110

Arg Pro Val Ala Val Asp Leu Thr Tyr Ile Pro Val Val Gly His Ala
        115                 120                 125

Leu Ser Ala Ala Phe Gln Ala Pro Phe Cys Ala Gly Ala Met Ala Val
    130                 135                 140

Val Gly Gly Ala Leu Ala Tyr Leu Val Val Lys Thr Leu Ile Asn Ala
145                 150                 155                 160

Thr Gln Leu Leu Lys Leu Leu Ala Lys Leu Ala Glu Leu Val Ala Ala
                165                 170                 175

Ala Ile Ala Asp Ile Ile Ser Asp Val Ala Asp Ile Ile Lys Gly Thr
            180                 185                 190

Leu Gly Glu Val Trp Glu Phe Ile Thr Asn Ala Leu Asn Gly Leu Lys
        195                 200                 205
```

Glu Leu Trp Asp Lys Leu Thr Gly Trp Val Thr Gly Leu Phe Ser Arg
    210                 215                 220

Gly Trp Ser Asn Leu Glu Ser Phe Phe Ala Gly Val Pro Gly Leu Thr
225                 230                 235                 240

Gly Ala Thr Ser Gly Leu Ser Gln Val Thr Gly Leu Phe Gly Ala Ala
                245                 250                 255

Gly Leu Ser Ala Ser Ser Gly Leu Ala His Ala Asp Ser Leu Ala Ser
                260                 265                 270

Ser Ala Ser Leu Pro Ala Leu Ala Gly Ile Gly Gly Ser Gly Phe
            275                 280                 285

Gly Gly Leu Pro Ser Leu Ala Gln Val His Ala Ser Thr Arg Gln
    290                 295                 300

Ala Leu Arg Pro Arg Ala Asp Gly Pro Val Gly Ala Ala Glu Gln
305                 310                 315                 320

Val Gly Gly Gln Ser Gln Leu Val Ser Ala Gln Gly Ser Gln Gly Met
                325                 330                 335

Gly Gly Pro Val Gly Met Gly Gly Met His Pro Ser Ser Gly Ala Ser
                340                 345                 350

Lys Gly Thr Thr Thr Lys Lys Tyr Ser Glu Gly Ala Ala Ala Gly Thr
            355                 360                 365

Glu Asp Ala Glu Arg Ala Pro Val Glu Ala Asp Ala Gly Gly Gly Gln
    370                 375                 380

Lys Val Leu Val Arg Asn Val Val
385                 390

(2) INFORMATION FOR SEQ ID NO:139:

(i) SEQUENCE CHARACTERISTICS:
        (A) LENGTH: 439 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:139:

ACGTTTACCC ATGCCGTCGG TGCAGAGCAA CGCCAGACAA CACAAAGTAG TCTAATTCCG      60

TTATAAAGCA GACATTTCCG TGGTTATGTA GAAGATGTCG ACCGATCAGA TGAAGCGATC     120

CGCGTCAGGT GGTATCCGAT GTCTTTTGTG ACCATCCAGC CGGTGGTCTT GGCAGCCGCG     180

ACGGGGACT TGCCGACGAT CGGTACCGCC GTGAGTGCTC GGAACACAGC CGTCTGTGCC      240

CCGACGACGG GGGTGTTACC CCCTGCTGCC AATGACGTGT CGGTCCTGAC GGCGGCCCGG     300

TTCACCGCGC ACACCAAGCA CTACCGAGTG GTGAGTAAGC CGGCCGCGCT GGTCCATGGC     360

ATGTTCGTGG CCCTCCCGGC GGCCACCGCC GATGCGTATG CGACCACCGA GGCCGTCAAT     420

GTGGTCGCGA CCGGTTAAG                                                  439

(2) INFORMATION FOR SEQ ID NO:140:

(i) SEQUENCE CHARACTERISTICS:
        (A) LENGTH: 1441 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:140:

-continued

```
GAGGTTGCTG GCAATGGATT TCGGGCTTTT ACCTCCGGAA GTGAATTCAA GCCGAATGTA      60

TTCCGGTCCG GGGCCGGAGT CGATGCTAGC CGCCGCGGCC GCCTGGGACG GTGTGGCCGC     120

GGAGTTGACT TCCGCCGCGG TCTCGTATGG ATCGGTGGTG TCGACGCTGA TCGTTGAGCC     180

GTGGATGGGG CCGGCGGCGG CCGCGATGGC GGCCGCGGCA ACGCCGTATG TGGGGTGGCT     240

GGCCGCCACG GCGGCGCTGG CGAAGGAGAC GGCCACACAG GCGAGGGCAG CGGCGGAAGC     300

GTTTGGGACG GCGTTCGCGA TGACGGTGCC ACCATCCCTC GTCGCGGCCA ACCGCAGCCG     360

GTTGATGTCG CTGGTCGCGG CGAACATTCT GGGGCAAAAC AGTGCGGCGA TCGCGGCTAC     420

CCAGGCCGAG TATGCCGAAA TGTGGGCCCA AGACGCTGCC GTGATGTACA GCTATGAGGG     480

GGCATCTGCG GCCGCGTCGG CGTTGCCGCC GTTCACTCCA CCCGTGCAAG CACCGGCCC     540

GGCCGGGCCC GCGGCCGCAG CCGCGGCGAC CCAAGCCGCC GGTGCGGGCG CCGTTGCGGA     600

TGCACAGGCG ACACTGGCCC AGCTGCCCCC GGGGATCCTG AGCGACATTC TGTCCGCATT     660

GGCCGCCAAC GCTGATCCGC TGACATCGGG ACTGTTGGGG ATCGCGTCGA CCCTCAACCC     720

GCAAGTCGGA TCCGCTCAGC CGATAGTGAT CCCCACCCCG ATAGGGGAAT TGGACGTGAT     780

CGCGCTCTAC ATTGCATCCA TCGCGACCGG CAGCATTGCG CTCGCGATCA CGAACACGGC     840

CAGACCCTGG CACATCGGCC TATACGGGAA CGCCGGCGGG CTGGGACCGA CGCAGGGCCA     900

TCCACTGAGT TCGGCGACCG ACGAGCCGGA GCCGCACTGG GGCCCCTTCG GGGCGCGGC     960

GCCGGTGTCC GCGGGCGTCG GCCACGCAGC ATTAGTCGGA GCGTTGTCGG TGCCGCACAG    1020

CTGGACCACG GCCGCCCCGG AGATCCAGCT CGCCGTTCAG GCAACACCCA CCTTCAGCTC    1080

CAGCGCCGGC GCCGACCCGA CGGCCCTAAA CGGGATGCCG GCAGGCCTGC TCAGCGGGAT    1140

GGCTTTGGCG AGCCTGGCCG CACGCGGCAC GACGGGCGGT GGCGGCACCC GTAGCGGCAC    1200

CAGCACTGAC GGCCAAGAGG ACGGCCGCAA ACCCCGGTA GTTGTGATTA GAGAGCAGCC    1260

GCCGCCCGGA AACCCCCCGC GGTAAAAGTC CGGCAACCGT TCGTCGCCGC GCGGAAAATG    1320

CCTGGTGAGC GTGGCTATCC GACGGGCCGT TCACACCGCT TGTAGTAGCG TACGGCTATG    1380

GACGACGGTG TCTGGATTCT CGGCGGCTAT CAGAGCGATT TTGCTCGCAA CCTCAGCAAA    1440

G                                                                   1441
```

(2) INFORMATION FOR SEQ ID NO:141:

(i) SEQUENCE CHARACTERISTICS:
        (A) LENGTH: 99 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:141:

```
Met Ser Phe Val Thr Ile Gln Pro Val Val Leu Ala Ala Ala Thr Gly
 1               5                  10                  15

Asp Leu Pro Thr Ile Gly Thr Ala Val Ser Ala Arg Asn Thr Ala Val
            20                  25                  30

Cys Ala Pro Thr Thr Gly Val Leu Pro Pro Ala Ala Asn Asp Val Ser
        35                  40                  45

Val Leu Thr Ala Ala Arg Phe Thr Ala His Thr Lys His Tyr Arg Val
    50                  55                  60

Val Ser Lys Pro Ala Ala Leu Val His Gly Met Phe Val Ala Leu Pro
65                  70                  75                  80

Ala Ala Thr Ala Asp Ala Tyr Ala Thr Thr Glu Ala Val Asn Val Val
```

85                  90                  95

Ala Thr Gly (2) INFORMATION FOR SEQ ID NO:142:

(i) SEQUENCE CHARACTERISTICS:
      (A) LENGTH: 423 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:142:

Met Asp Phe Gly Leu Leu Pro Pro Glu Val Asn Ser Ser Arg Met Tyr
1               5                   10                  15

Ser Gly Pro Gly Pro Glu Ser Met Leu Ala Ala Ala Ala Trp Asp
            20                  25                  30

Gly Val Ala Ala Glu Leu Thr Ser Ala Ala Val Ser Tyr Gly Ser Val
            35                  40                  45

Val Ser Thr Leu Ile Val Glu Pro Trp Met Gly Pro Ala Ala Ala Ala
50                  55                  60

Met Ala Ala Ala Ala Thr Pro Tyr Val Gly Trp Leu Ala Ala Thr Ala
65                  70                  75                  80

Ala Leu Ala Lys Glu Thr Ala Thr Gln Ala Arg Ala Ala Glu Ala
                85                  90                  95

Phe Gly Thr Ala Phe Ala Met Thr Val Pro Pro Ser Leu Val Ala Ala
            100                 105                 110

Asn Arg Ser Arg Leu Met Ser Leu Val Ala Ala Asn Ile Leu Gly Gln
            115                 120                 125

Asn Ser Ala Ala Ile Ala Ala Thr Gln Ala Glu Tyr Ala Glu Met Trp
130                 135                 140

Ala Gln Asp Ala Ala Val Met Tyr Ser Tyr Glu Gly Ala Ser Ala Ala
145                 150                 155                 160

Ala Ser Ala Leu Pro Pro Phe Thr Pro Pro Val Gln Gly Thr Gly Pro
                165                 170                 175

Ala Gly Pro Ala Ala Ala Ala Ala Thr Gln Ala Ala Gly Ala Gly
            180                 185                 190

Ala Val Ala Asp Ala Gln Ala Thr Leu Ala Gln Leu Pro Pro Gly Ile
            195                 200                 205

Leu Ser Asp Ile Leu Ser Ala Leu Ala Asn Ala Asp Pro Leu Thr
210                 215                 220

Ser Gly Leu Leu Gly Ile Ala Ser Thr Leu Asn Pro Gln Val Gly Ser
225                 230                 235                 240

Ala Gln Pro Ile Val Ile Pro Thr Pro Ile Gly Glu Leu Asp Val Ile
                245                 250                 255

Ala Leu Tyr Ile Ala Ser Ile Ala Thr Gly Ser Ile Ala Leu Ala Ile
            260                 265                 270

Thr Asn Thr Ala Arg Pro Trp His Ile Gly Leu Tyr Gly Asn Ala Gly
            275                 280                 285

Gly Leu Gly Pro Thr Gln Gly His Pro Leu Ser Ser Ala Thr Asp Glu
290                 295                 300

Pro Glu Pro His Trp Gly Pro Phe Gly Gly Ala Ala Pro Val Ser Ala
305                 310                 315                 320

Gly Val Gly His Ala Ala Leu Val Gly Ala Leu Ser Val Pro His Ser
            325                 330                 335

```
Trp Thr Thr Ala Ala Pro Glu Ile Gln Leu Ala Val Gln Ala Thr Pro
            340                 345                 350

Thr Phe Ser Ser Ser Ala Gly Ala Asp Pro Thr Ala Leu Asn Gly Met
            355                 360                 365

Pro Ala Gly Leu Leu Ser Gly Met Ala Leu Ala Ser Leu Ala Ala Arg
            370                 375                 380

Gly Thr Thr Gly Gly Gly Thr Arg Ser Gly Thr Ser Thr Asp Gly
385                 390                 395                 400

Gln Glu Asp Gly Arg Lys Pro Pro Val Val Ile Arg Glu Gln Pro
                405                 410                 415

Pro Pro Gly Asn Pro Pro Arg
            420
```

(2) INFORMATION FOR SEQ ID NO:143:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:143:

```
Met Ser Leu Leu Asp Ala His Ile Pro Gln Leu Val Ala Ser Gln Ser
1               5                   10                  15

Ala Phe Ala Ala Lys Ala Gly Leu Met Arg His Thr Ile Gly Gln Ala
            20                  25                  30

Glu Gln Ala Ala Met Ser Ala Gln Ala Phe His Gln Gly Glu Ser Ser
            35                  40                  45

Ala Ala Phe Gln Ala Ala His Ala Arg Phe Val Ala Ala Ala Ala Lys
    50                  55                  60

Val Asn Thr Leu Leu Asp Val Ala Gln Ala Asn Leu Gly Glu Ala Ala
65                  70                  75                  80

Gly Thr Tyr Val Ala Ala Asp Ala Ala Ala Ser Thr Tyr Thr Gly
                85                  90                  95

Phe
```

(2) INFORMATION FOR SEQ ID NO:144:

(i) SEQUENCE CHARACTERISTICS:
        (A) LENGTH: 99 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:144:

```
Cys Arg Leu Cys Leu Asp Ser His Leu Arg Val Val Ala Leu Pro Ala
1               5                   10                  15

Gly Gln Pro Gly Arg Leu Val Gln Ala Ile Gly Pro Ala Gln Glu Arg
            20                  25                  30

Asp Val Gly Gln Thr Arg Cys Thr Arg Thr Gly Leu Asp Xaa Val Ser
            35                  40                  45

Ala Leu Thr Ala Ala Gln Phe Ala Ala His Ala Gln Ile Tyr Gln Ala
    50                  55                  60

Val Ser Ala Gln Ala Ala Ala Ile His Glu Met Phe Val Asn Thr Leu
65                  70                  75                  80
```

-continued

```
Gln Xaa Xaa Ser Gly Ser Tyr Ala Ala Thr Glu Ala Ala Asn Ala Ala
            85                  90                  95

Ala Ala Gly
```